(12) United States Patent
Mann et al.

(10) Patent No.: US 10,947,595 B2
(45) Date of Patent: *Mar. 16, 2021

(54) NUCLEIC ACIDS AND METHODS FOR DETECTING CHROMOSOMAL ABNORMALITIES

(71) Applicant: Progenity, Inc., San Diego, CA (US)

(72) Inventors: Tobias Mann, Ann Arbor, MI (US); Heng Wang, Walnut Creek, CA (US); Jung H. Kim, Northville, MI (US); Matthew Sekedat, Ann Arbor, MI (US)

(73) Assignee: Progenity, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/943,870

(22) Filed: Jul. 30, 2020

(65) Prior Publication Data

US 2020/0354792 A1   Nov. 12, 2020

Related U.S. Application Data

(60) Continuation of application No. 16/596,118, filed on Oct. 8, 2019, which is a division of application No. 15/224,463, filed on Jul. 29, 2016, now Pat. No. 10,465,245.

(60) Provisional application No. 62/198,654, filed on Jul. 29, 2015.

(51) Int. Cl.
| | |
|---|---|
| *C12Q 1/6883* | (2018.01) |
| *G16B 25/00* | (2019.01) |
| *G16B 30/00* | (2019.01) |
| *C12Q 1/6811* | (2018.01) |
| *C12Q 1/6827* | (2018.01) |
| *G16H 50/20* | (2018.01) |
| *C12Q 1/6816* | (2018.01) |

(52) U.S. Cl.
CPC .......... *C12Q 1/6883* (2013.01); *C12Q 1/6811* (2013.01); *C12Q 1/6816* (2013.01); *C12Q 1/6827* (2013.01); *G16B 25/00* (2019.02); *G16B 30/00* (2019.02); *G16H 50/20* (2018.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | |
|---|---|---|
| 5,817,921 A | 10/1998 | Tom et al. |
| 5,866,337 A | 2/1999 | Schon |
| 6,027,889 A | 2/2000 | Barany et al. |
| 6,210,891 B1 | 4/2001 | Nyren et al. |
| 6,306,597 B1 | 10/2001 | Macevicz |
| 6,558,928 B1 | 5/2003 | Landegren |
| 6,828,100 B1 | 12/2004 | Ronaghi |
| 6,833,246 B2 | 12/2004 | Balasubramanian |
| 6,852,487 B1 | 2/2005 | Barany et al. |
| 6,858,412 B2 | 2/2005 | Willis et al. |
| 6,911,345 B2 | 6/2005 | Quake et al. |
| 7,232,656 B2 | 6/2007 | Balasubramanian et al. |
| 7,320,860 B2 | 1/2008 | Landegren et al. |
| 7,351,528 B2 | 4/2008 | Landegren |
| 7,598,035 B2 | 10/2009 | Macevicz |
| 7,835,871 B2 | 11/2010 | Kain et al. |
| 7,960,120 B2 | 6/2011 | Rigatti et al. |
| 9,090,934 B2 | 7/2015 | Lucero et al. |
| 9,228,234 B2 | 1/2016 | Rabinowitz et al. |
| 9,424,392 B2 | 8/2016 | Rabinowitz et al. |
| 10,227,652 B2 | 2/2019 | Rabinowitz et al. |
| 10,240,202 B2 | 3/2019 | Rabinowitz et al. |
| 10,266,893 B2 | 4/2019 | Rabinowitz et al. |
| 10,465,245 B2 * | 11/2019 | Mann .................. G16B 30/00 |
| 10,522,242 B2 | 12/2019 | Rabinowitz et al. |
| 2006/0024681 A1 | 2/2006 | Smith et al. |
| 2006/0292611 A1 | 12/2006 | Berka et al. |
| 2007/0114362 A1 | 5/2007 | Feng et al. |
| 2008/0269068 A1 | 10/2008 | Church et al. |
| 2011/0009278 A1 | 1/2011 | Kain et al. |
| 2013/0022973 A1 * | 1/2013 | Hansen ................ C12Q 1/6883 435/6.11 |
| 2013/0072390 A1 | 3/2013 | Wang et al. |
| 2014/0342354 A1 | 11/2014 | Evans et al. |
| 2015/0141257 A1 | 5/2015 | Albert et al. |
| 2017/0183731 A1 | 6/2017 | Mann et al. |
| 2020/0032344 A1 | 1/2020 | Mann et al. |

FOREIGN PATENT DOCUMENTS

| | | | | |
|---|---|---|---|---|
| WO | WO 2005/014846 | * | 2/2005 | ............... C12Q 1/68 |
| WO | WO2007/147076 | | 12/2007 | |
| WO | WO2010/126614 | | 11/2010 | |
| WO | WO2011/066476 | | 3/2011 | |
| WO | WO2014/039556 | | 3/2014 | |
| WO | WO 2014/145232 | * | 9/2014 | ............... C12Q 1/68 |

(Continued)

OTHER PUBLICATIONS

Thiyagarajan et al. BMC Bioinformatics vol. 7, article 500 (Year: 2006).*

(Continued)

*Primary Examiner* — John S Brusca

(74) *Attorney, Agent, or Firm* — Casimir Jones, S.C.; Mary Ann D. Brow

(57) ABSTRACT

Methods and nucleic acid molecules for detecting chromosomal abnormalities such as aneuploidy. Methods for selecting nucleic acid molecules for use in the methods of the disclosure.

15 Claims, 10 Drawing Sheets

Specification includes a Sequence Listing.

(56) References Cited

FOREIGN PATENT DOCUMENTS

| WO | WO2017/020023 | 2/2017 |
|----|---------------|--------|
| WO | WO2017/020024 | 2/2017 |

OTHER PUBLICATIONS

Porreca et al. Multiplex amplification of large sets of human exons Nature Methods vol. 4, pp. 931-936 (Year: 2007).*
Agarwal et al. Commercial landscape of noninvasive prenatal testing in the United States Prenatal Diagnosis vol. 33, pp. 521-531 (Year: 2013).*
Brewster et al., Copy number imbalances between screen- and symptom-detected breast cancers and impact on disease-free survival. Cancer Prev Res (Phila). Oct. 2011;4(10):1609-16.
Burmester et al., DMET microarray technology for pharmacogenomics-based personalized medicine. Methods Mol Biol. 2010;632:99-124.
Caldwell et al., CYP4F2 genetic variant alters required warfarin dose. Blood. Apr. 15, 2008;111(8):4106-12.
Chiu et al., Noninvasive prenatal diagnosis of fetal chromosomal aneuploidy by massively parallel genomic sequencing of DNA in maternal plasma. Proc Natl Acad Sci U S A. Dec. 23, 2008;105(51):20458-6.
Daly et al., Multiplex assay for comprehensive genotyping of genes involved in drug metabolism, excretion, and transport. Clin Chem. Jul. 2007;53(7):1222-30.
Deeken et al., A pharmacogenetic study of docetaxel and thalidomide in patients with castration-resistant prostate cancer using the DMET genotyping platform. Pharmacogenomics J. Jun. 2010;10(3):191-9.
Deeken, The Affymetrix DMET platform and pharmacogenetics in drug development. Curr Opin Mol Ther. Jun. 2009;11(3):260-8.
Dumaual et al., Comprehensive assessment of metabolic enzyme and transporter genes using the Affymetrix Targeted Genotyping System. Pharmacogenomics. Mar. 2007;8(3):293-305.
Eason et al., Characterization of synthetic DNA bar codes in *Saccharomyces cerevisiae* gene-deletion strains. Proc Natl Acad Sci U S A. Jul. 27, 2004;101(30):11046-51.
Ericsson et al., A dual-tag microarray platform for high-performance nucleic acid and protein analyses. Nucleic Acids Res. May 2008; 36(8): e45. 9 pages.
Fan et al., Noninvasive diagnosis of fetal aneuploidy by shotgun sequencing DNA from maternal blood. Proc Natl Acad Sci U S A. Oct. 21, 2008;105(42):16266-71.
Fu et al. Counting individual DNA molecules by the stochastic attachment of diverse labels. Proc Natl Acad Sci U S A. May 31, 2011;108(22):9026-31.
Geiersbach et al., Unknown partner for USP6 and unusual SS18 rearrangement detected by fluorescence in situ hybridization in a solid aneurysmal bone cyst. Cancer Genet. Apr. 2011;204(4):195-202.

Hardenbol et al., Highly multiplexed molecular inversion probe genotyping: over 10,000 targeted SNPs genotyped in a single tube assay. Genome Res. Feb. 2005;15(2):269-75.
Hardenbol et al., Multiplexed genotyping with sequence-tagged molecular inversion probes. Nat Biotechnol. Jun. 2003;21(6):673-8.
Johnson et al., Identification of copy number alterations associated with the progression of DCIS to invasive ductal carcinoma. Breast Cancer Res Treat. Jun. 2012;133(3):889-98.
Ji et al., Molecular inversion probe analysis of gene copy alterations reveals distinct categories of colorectal carcinoma. Cancer Res. Aug. 15, 2006;66(16):7910-9.
Mamanova et al., Target-enrichment strategies for next-generation sequencing. Nat Methods. Feb. 2010;7(2):111-8.
Man et al., Genetic variation in metabolizing enzyme and transporter genes: comprehensive assessment in 3 major East Asian subpopulations with comparison to Caucasians and Africans. J Clin Pharmacol. Aug. 2010;50(8):929-40.
McDonald et al., CYP4F2 is a vitamin K1 oxidase: An explanation for altered warfarin dose in carriers of the V433M variant. Mol Pharmacol. Jun. 2009;75(6):1337-46.
Mega et al., Cytochrome p-450 polymorphisms and response to clopidogrel. N Engl J Med. Jan. 22, 2009;360(4):354-62.
Press et al., Ovarian carcinomas with genetic and epigenetic BRCA1 loss have distinct molecular abnormalities. BMC Cancer. Jan. 22, 2008;8:17.
Schiffman et al., Molecular inversion probes reveal patterns of 9p21 deletion and copy number aberrations in childhood leukemia. Cancer Genet Cytogenet. 2009;193(1):9-18.
Schiffman et al., Oncogenic BRAF mutation with CDKN2A inactivation is characteristic of a subset of pediatric malignant astrocytomas. Cancer Res. Jan. 15, 2010;70(2):512-9.
Sissung et al., Clinical pharmacology and pharmacogenetics in a genomics era: the DMET platform. Pharmacogenomics. Jan. 2010;11(1):89-103.
Turner et al., Massively parallel exon capture and library-free resequencing across 16 genomes. Nat Methods. May 2009;6(5):315-6.
Wang et al., Allele quantification using molecular inversion probes (MIP). Nucleic Acids Res. Nov. 28, 2005;33(21):e183.
Wang et al., Analysis of molecular inversion probe performance for allele copy number determination. Genome Biol. 2007;8(11):R246.
Wang et al., High quality copy number and genotype data from FFPE samples using Molecular Inversion Probe (MIP) microarrays. BMC Med Genomics. Feb. 19, 2009;2:8.
Wang et al., Molecular inversion probes: a novel microarray technology and its application in cancer research. Cancer Genet. Jul.-Aug. 2012;205(7-8):341-55.
International Search Report and Written Opinion for PCT/US2016/044914, dated Jan. 27, 2017, 20 pages.
International Search Report and Written Opinion for PCT/US2016/044915, dated Jan. 23, 2017, 23 pages.

* cited by examiner

Healthy

Alu element

SEQUENCE LISTING

```
<160> NUMBER OF SEQ ID NOS: 27

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1
cttcagcttc ccgattacgg                                                     20

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 2
gcacgatccg acggtagtgt                                                     20

<210> SEQ ID NO 3
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 3
cttcagcttc ccgattacgg gcacgatccg acggtagtgt                               40

<210> SEQ ID NO 4
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 4
cactgcactc cagcctgg                                                       18

<210> SEQ ID NO 5
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 5
gaggctgagg caggagaa                                                       18

<210> SEQ ID NO 6
<211> LENGTH: 88
<212> TYPE: DNA
```

```
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (19)..(24)
<223> OTHER INFORMATION: a, c, t, g, unknown or other
<220> FEATURE:
<221> NAME/KEY: modified_base
<222> LOCATION: (65)..(70)
<223> OTHER INFORMATION: a, c, t, g, unknown or other
<220> FEATURE:
<223> OTHER INFORMATION: See specification as filed for detailed
      description of substitutions and preferred embodiments

<400> SEQUENCE: 6
cactgcactc cagcctggnn nnnncttcag cttcccgatt acgggcacga tccgacggta      60
gtgtnnnnnn gaggctgagg caggagaa                                        88

<210> SEQ ID NO 7
<211> LENGTH: 88
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (19)..(24)
<223> OTHER INFORMATION: a, c, t, g, unknown or other
<220> FEATURE:
<221> NAME/KEY: modified_base
<222> LOCATION: (65)..(70)
<223> OTHER INFORMATION: a, c, t, g, unknown or other

<400> SEQUENCE: 7
ccactgcact ccagcctgnn nnnncttcag cttcccgatt acgggcacga tccgacggta      60
gtgtnnnnnn gaggctgagg caggagaa                                        88

<210> SEQ ID NO 8
<211> LENGTH: 88
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (19)..(24)
<223> OTHER INFORMATION: a, c, t, g, unknown or other
<220> FEATURE:
<221> NAME/KEY: modified_base
<222> LOCATION: (65)..(70)
<223> OTHER INFORMATION: a, c, t, g, unknown or other

<400> SEQUENCE: 8
tctcctgcct cagcctccnn nnnncttcag cttcccgatt acgggcacga tccgacggta      60
gtgtnnnnnn aggctggagt gcagtggc                                        88

<210> SEQ ID NO 9
<211> LENGTH: 88
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (19)..(24)
<223> OTHER INFORMATION: a, c, t, g, unknown or other
<220> FEATURE:
<221> NAME/KEY: modified_base
<222> LOCATION: (65)..(70)
```

<223> OTHER INFORMATION: a, c, t, g, unknown or other

<400> SEQUENCE: 9

```
cactgcactc cagcctggnn nnnncttcag cttcccgatt acgggcacga tccgacggta    60
gtgtnnnnnn gaggctgagg caggagaa                                       88
```

<210> SEQ ID NO 10
<211> LENGTH: 88
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (19)..(24)
<223> OTHER INFORMATION: a, c, t, g, unknown or other
<220> FEATURE:
<221> NAME/KEY: modified_base
<222> LOCATION: (65)..(70)
<223> OTHER INFORMATION: a, c, t, g, unknown or other

<400> SEQUENCE: 10

```
ccactgcact ccagcctgnn nnnncttcag cttcccgatt acgggcacga tccgacggta    60
gtgtnnnnnn ggaggctgag gcaggaga                                       88
```

<210> SEQ ID NO 11
<211> LENGTH: 88
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (19)..(24)
<223> OTHER INFORMATION: a, c, t, g, unknown or other
<220> FEATURE:
<221> NAME/KEY: modified_base
<222> LOCATION: (65)..(70)
<223> OTHER INFORMATION: a, c, t, g, unknown or other

<400> SEQUENCE: 11

```
cactgcactc cagcctggnn nnnncttcag cttcccgatt acgggcacga tccgacggta    60
gtgtnnnnnn caggaggctg aggcagga                                       88
```

<210> SEQ ID NO 12
<211> LENGTH: 86
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (18)..(23)
<223> OTHER INFORMATION: a, c, t, g, unknown or other
<220> FEATURE:
<221> NAME/KEY: modified_base
<222> LOCATION: (64)..(69)
<223> OTHER INFORMATION: a, c, t, g, unknown or other

<400> SEQUENCE: 12

```
actgcactcc agcctggnnn nnncttcagc ttcccgatta cgggcacgat ccgacggtag    60
tgtnnnnnng gaggctgagg caggag                                         86
```

<210> SEQ ID NO 13
<211> LENGTH: 88
<212> TYPE: DNA
<213> ORGANISM: Artificial Sequence

```
<220> FEATURE:
<223> OTHER INFORMATION: Synthetic oligonucleotide
<220> FEATURE:
<221> NAME/KEY: modified_base
<222> LOCATION: (19)..(24)
<223> OTHER INFORMATION: a, c, t, g, unknown or other
<220> FEATURE:
<221> NAME/KEY: modified_base
<222> LOCATION: (65)..(70)
<223> OTHER INFORMATION: a, c, t, g, unknown or other

<400> SEQUENCE: 13
tgcactccag cctgggcann nnnncttcag ctttcccgatt acgggcacga tccgacggta     60
gtgtnnnnnn gaggctgagg caggagaa                                         88

<210> SEQ ID NO 14
<211> LENGTH: 88
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (19)..(24)
<223> OTHER INFORMATION: a, c, t, g, unknown or other
<220> FEATURE:
<221> NAME/KEY: modified_base
<222> LOCATION: (65)..(70)
<223> OTHER INFORMATION: a, c, t, g, unknown or other

<400> SEQUENCE: 14
ctgcactcca gcctgggcnn nnnncttcag cttcccgatt acgggcacga tccgacggta     60
gtgtnnnnnn gaggctgagg caggagaa                                        88

<210> SEQ ID NO 15
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 15
tgcactccag cctg                                                       14

<210> SEQ ID NO 16
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 16
gaggctgagg cagga                                                      15

<210> SEQ ID NO 17
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 17
tcctgcctca gcctc                                                      15

<210> SEQ ID NO 18
<211> LENGTH: 12
<212> TYPE: DNA
```

```
<213> ORGANISM: Artificial Sequence
<220> FEATURE:
<223> OTHER INFORMATION: Synthetic oligonucleotide

<400> SEQUENCE: 18
aggctggagt gc                                                              12

<210> SEQ ID NO 19
<211> LENGTH: 88
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (19)..(24)
<223> OTHER INFORMATION: a, c, t, g, unknown or other
<220> FEATURE:
<221> NAME/KEY: modified_base
<222> LOCATION: (65)..(70)
<223> OTHER INFORMATION: a, c, t, g, unknown or other

<400> SEQUENCE: 19
ccactgcact ccagcctgnn nnnncttcag cttcccgatt acgggcacga tccgacggta          60
gtgtnnnnnn gaggctgagg caggagaa                                            88

<210> SEQ ID NO 20
<211> LENGTH: 88
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (19)..(24)
<223> OTHER INFORMATION: a, c, t, g, unknown or other
<220> FEATURE:
<221> NAME/KEY: modified_base
<222> LOCATION: (65)..(70)
<223> OTHER INFORMATION: a, c, t, g, unknown or other

<400> SEQUENCE: 20
tctcctgcct cagcctccnn nnnncttcag cttcccgatt acgggcacga tccgacggta          60
gtgtnnnnnn aggctggagt gcagtggc                                            88

<210> SEQ ID NO 21
<211> LENGTH: 88
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (19)..(24)
<223> OTHER INFORMATION: a, c, t, g, unknown or other
<220> FEATURE:
<221> NAME/KEY: modified_base
<222> LOCATION: (65)..(70)
<223> OTHER INFORMATION: a, c, t, g, unknown or other

<400> SEQUENCE: 21
cactgcactc cagcctggnn nnnncttcag cttcccgatt acgggcacga tccgacggta          60
gtgtnnnnnn gaggctgagg caggagaa                                            88

<210> SEQ ID NO 22
<211> LENGTH: 88
<212> TYPE: DNA
<213> ORGANISM: Artificial Sequence
```

```
<220> FEATURE:
<223> OTHER INFORMATION: Synthetic oligonucleotide
<220> FEATURE:
<221> NAME/KEY: modified_base
<222> LOCATION: (19)..(24)
<223> OTHER INFORMATION: a, c, t, g, unknown or other
<220> FEATURE:
<221> NAME/KEY: modified_base
<222> LOCATION: (65)..(70)
<223> OTHER INFORMATION: a, c, t, g, unknown or other

<400> SEQUENCE: 22
cactgcactc cagcctggnn nnnncttcag cttcccgatt acgggcacga tccgacggta    60
gtgtnnnnnn gaggctgagg caggagaa                                      88

<210> SEQ ID NO 23
<211> LENGTH: 88
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (19)..(24)
<223> OTHER INFORMATION: a, c, t, g, unknown or other
<220> FEATURE:
<221> NAME/KEY: modified_base
<222> LOCATION: (65)..(70)
<223> OTHER INFORMATION: a, c, t, g, unknown or other

<400> SEQUENCE: 23
ccactgcact ccagcctgnn nnnncttcag cttcccgatt acgggcacga tccgacggta    60
gtgtnnnnnn ggaggctgag gcaggaga                                      88

<210> SEQ ID NO 24
<211> LENGTH: 88
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (19)..(24)
<223> OTHER INFORMATION: a, c, t, g, unknown or other
<220> FEATURE:
<221> NAME/KEY: modified_base
<222> LOCATION: (65)..(70)
<223> OTHER INFORMATION: a, c, t, g, unknown or other

<400> SEQUENCE: 24
cactgcactc cagcctggnn nnnncttcag cttcccgatt acgggcacga tccgacggta    60
gtgtnnnnnn caggaggctg aggcagga                                      88

<210> SEQ ID NO 25
<211> LENGTH: 86
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (18)..(23)
<223> OTHER INFORMATION: a, c, t, g, unknown or other
<220> FEATURE:
<221> NAME/KEY: modified_base
<222> LOCATION: (64)..(69)
<223> OTHER INFORMATION: a, c, t, g, unknown or other

<400> SEQUENCE: 25
```

```
actgcactcc agcctggnnn nnncttcagc ttcccgatta cgggcacgat ccgacggtag    60
tgtnnnnnng gaggctgagg caggag                                         86

<210> SEQ ID NO 26
<211> LENGTH: 88
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (19)..(24)
<223> OTHER INFORMATION: a, c, t, g, unknown or other
<220> FEATURE:
<221> NAME/KEY: modified_base
<222> LOCATION: (65)..(70)
<223> OTHER INFORMATION: a, c, t, g, unknown or other

<400> SEQUENCE: 26
tgcactccag cctgggcann nnnncttcag cttcccgatt acgggcacga tccgacggta    60
gtgtnnnnnn gaggctgagg caggagaa                                       88

<210> SEQ ID NO 27
<211> LENGTH: 88
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (19)..(24)
<223> OTHER INFORMATION: a, c, t, g, unknown or other
<220> FEATURE:
<221> NAME/KEY: modified_base
<222> LOCATION: (65)..(70)
<223> OTHER INFORMATION: a, c, t, g, unknown or other

<400> SEQUENCE: 27
ctgcactcca gcctgggcnn nnnncttcag cttcccgatt acgggcacga tccgacggta    60
gtgtnnnnnn gaggctgagg caggagaa                                       88
```

NUCLEIC ACIDS AND METHODS FOR DETECTING CHROMOSOMAL ABNORMALITIES

CROSS REFERENCE TO RELATED APPLICATION

This application is a continuation of U.S. patent application Ser. No. 16/596,118, filed Oct. 8, 2019, which a divisional of U.S. patent application Ser. No. 15/224,463, filed Jul. 29, 2016, now U.S. Pat. No. 10,465,245, which claims the benefit of U.S. Provisional Application No. 62/198,654, filed on Jul. 29, 2015, each of which is hereby incorporated herein by reference in its entirety.

FIELD OF THE INVENTION

This invention relates to systems and methods for determining, inter alia, aneuploidies and chromosomal abnormalities in a subject in need thereof.

BACKGROUND OF THE INVENTION

Major chromosomal abnormalities are detected in nearly 1 of 140 live births and in a much higher fraction of fetuses that do not reach term or are still-born. Hsu (1998) Prenatal diagnosis of chromosomal abnormalities through amniocentesis. In: Milunsky A, editor. Genetic Disorders and the Fetus. 4 ed. Baltimore: The Johns Hopkins University Press. 179-180; Staebler et al. (2005) Should determination of the karyotype be systematic for all malformations detected by obstetrical ultrasound? Prenat Diagn 25: 567-573. The most common aneuploidy is trisomy 21 (Down syndrome), which currently occurs in 1 of 730 births. Hsu; Staebler et al. Though less common than trisomy 21, trisomy 18 (Edwards Syndrome) and trisomy 13 (Patau syndrome) occur in 1 in 5,500 and 1 in 17,200 live births, respectively. Hsu. A large variety of congenital defects, growth deficiencies, and intellectual disabilities are found in children with chromosomal aneuploidies, and these present life-long challenges to families and societies. Jones (2006) Smith's recognizable patterns of human malformation. Philadelphia: Elsevier Saunders. There are a variety of prenatal tests that can indicate increased risk for fetal aneuploidy, including invasive diagnostic tests such as amniocentesis or chorionic villus sampling, which are the current gold standard but are associated with a non-negligible risk of fetal loss. *American College of Obstetricians and Gynecologists* (2007) ACOG Practice Bulletin No. 88, December 2007. Invasive prenatal testing for aneuploidy. Obstet Gynecol 110: 1459-1467. More reliable, non-invasive tests for fetal aneuploidy have therefore long been sought. The most promising of these are based on the detection of fetal DNA in maternal plasma. It has been demonstrated that massively parallel sequencing of libraries generated from maternal plasma can reliably detect chromosome 21 abnormalities. Chiu et al., (2008) Noninvasive prenatal diagnosis of fetal chromosomal aneuploidy by massively parallel genomic sequencing of DNA in maternal plasma. Proc Natl Acad Sci USA 105:20458-20463; Fan et al., (2008) Noninvasive diagnosis of fetal aneuploidy by shotgun sequencing DNA from maternal blood. Proc Natl Acad Sci USA 105: 16266-16271.

Current methods for aneuploidy screening, such as massively parallel shot gun sequencing, are time-consuming or expensive, or require extensive bioinformatics analysis.

Therefore, there is a need for developing cost-effective and efficient tests that have high sensitivities and specificities.

SUMMARY OF THE INVENTION

Some embodiments of the disclosure are:
1. A method of detecting aneuploidy in a fetus comprising:
   a) obtaining a nucleic acid sample isolated from a maternal blood sample;
   b) capturing a plurality of target sequences of interest in the nucleic acid sample obtained in step a) by using one or more populations of molecular inversion probes (MIPs) to produce a plurality of replicons,
   wherein each of the MIPs in the population of MIPs comprises in sequence the following components:
      first targeting polynucleotide arm-first unique molecular tag-polynucleotide linker-second unique molecular tag-second targeting polynucleotide arm;
   wherein the pair of first and second targeting polynucleotide arms in each of the MIPs are identical, and are substantially complementary to first and second regions in the nucleic acid that, respectively, flank each sequence in the plurality of target sequences of interest;
   wherein the first and second unique targeting molecular tags in each of the MIPs in combination are distinct in each of the MIPs;
   c) sequencing a plurality of MIPs amplicons that are amplified from the replicons obtained in step b);
   d) determining the number of capture events of each of a first population of amplicons of the plurality of amplicons provided in step c) based on the number of the unique molecular tags of each MIP that amplified a replicon, wherein the first population of amplicons is determined by the sequence of the target sequence of interest;
   e) determining the number of capture events of each of a second population of amplicons of the plurality of amplicons provided in step c) based on the number of the unique molecular tags of each MIP that amplified a replicon, wherein the second population of amplicons is determined by the sequence of the target sequence of interest;
   f) determining, for each target sequence of interest from which the first population of amplicons was produced, a site capture metric based at least in part on the number of capture events determined in step d);
   g) identifying a first subset of the site capture metrics determined in step f) that satisfy at least one criterion;
   h) determining, for each target sequence of interest from which the second population of amplicons was produced, a site capture metric based at least in part on the number of capture events determined in step e);
   i) identifying a second subset of the site capture metrics determined in step h) that satisfy the at least one criterion;
   j) normalizing a first measure determined from the first subset of site capture metrics identified in step g) by a second measure determined from the second subset of site capture metrics identified in step i) to obtain a test ratio;
   k) comparing the test ratio to a plurality of reference ratios that are computed based on reference nucleic acid samples isolated from reference subjects known to exhibit euploidy or aneuploidy; and
   l) determining, based on the comparing in step k), whether aneuploidy is detected in the fetus.
2. The method of embodiment 1, wherein the nucleic acid sample is DNA or RNA.
3. The method of embodiment 2, wherein the nucleic acid sample is genomic DNA.

4. The method of any one of embodiments 1-3, wherein the blood sample is a whole blood sample, a plasma sample, or a serum sample.

5. The method of embodiment 4, wherein the blood sample is a plasma sample.

6. The method of any one of embodiments 1-5, wherein the length of the first targeting polynucleotide arm is between 14 and 30 base pairs.

7. The method of any one of embodiments 1-6, wherein the length of the second targeting polynucleotide arm is between 14 and 30 base pairs.

8. The method of any one of embodiments 1-7, wherein each of the targeting polynucleotide arms has a melting temperature between 45° C. and 80° C.

9. The method of any one of embodiments 1-8, wherein each of the targeting polynucleotide arms has a GC content between 30% and 80%, or between 30% and 70%.

10. The method of any one of embodiments 1-9, wherein the length of the first unique molecular tag is between 4 and 15 base pairs.

11. The method of any one of embodiments 1-10, wherein the length of the second unique molecular tag is between 4 and 15 base pairs.

12. The method of any one of embodiments 1-11, wherein each of the unique molecular tags has a melting temperature between 45° C. and 80° C.

13. The method of any one of embodiments 1-12, wherein each of the unique molecular tags have a GC content between 30% and 80%, or between 30% and 70%.

14. The method of any one of embodiments 1-13, wherein the polynucleotide linker is not substantially complementary to any genomic region of the subject.

15. The method of any one of embodiments 1-14, wherein the polynucleotide linker has a length of between 14 and 30 base pairs.

16. The method of any one of embodiments 1-15, wherein the polynucleotide linker has a melting temperature of between 45° C. and 80° C.

17. The method of any one of embodiments 1-16, wherein the polynucleotide linker has a GC content between 30% and 80%, or between 30% and 70%.

18. The method of any one of embodiments 1-17, wherein the polynucleotide linker comprises at least one amplification primer.

19. The method of embodiment 18, wherein the polynucleotide linker comprises a forward amplification primer and a reverse amplification primer.

20. The method of embodiment 19, wherein the sequence of the forward amplification primer comprises the nucleotide sequence of

5'-CTTCAGCTTCCCGATTACGG-3'.   (SEQ ID NO: 1)

21. The method of embodiments 19, wherein the sequence of the reverse amplification primer comprises the nucleotide sequence of

5'-GCACGATCCGACGGTAGTGT-3'.   (SEQ ID NO: 2)

22. The method of any one of embodiments 1-21, wherein the polynucleotide linker comprises the nucleotide sequence of (SEQ ID NO: 3)
5'-CTTCAGCTTCCCGATTACGGGCACGATCCGACGGTAGTGT-3'.

23. The method of any one of embodiments 1-22, wherein the first targeting polynucleotide arm comprises the nucleotide sequence of

5'-CACTGCACTCCAGCCTGG-3'.   (SEQ ID NO: 4)

24. The method of any one of embodiments 1-23, wherein the second targeting polynucleotide arm comprises the nucleotide sequence of

5'-GAGGCTGAGGCAGGAGAA-3'.   (SEQ ID NO: 5)

25. The method of any one of embodiments 1-24, wherein the MIP comprises the nucleotide sequence of 5'-CACTGCACTCCAGCCTGG($N_{1-6}$) CTTCAGCTTCCCGATTACGGGCAC-GATCCGACGGTAGTGT($N_{7-12}$) GAGGCTGAGGCAG-GAGAA-3' (SEQ ID NO: 6), wherein ($N_{1-6}$) represents the first unique molecular tag and ($N_{7-12}$) represents the second unique molecular tag.

26. The method of any one of embodiments 1-24, wherein the MIP comprises the nucleotide sequence of any one of MIP 001-008 (SEQ ID NOS: 7-14).

27. The method of any one of embodiments 1-26, wherein the population of MIPs has a concentration between 10 fM and 100 nM.

28. The method of any one of embodiments 1-27, wherein each of the MIPs replicons is a single-stranded circular nucleic acid molecule.

29. The method of any one of embodiments 1-28, wherein the site capture metric is a site capture efficiency index (SCE).

30. The method of any one of embodiments 1-29, wherein the site capture metric is a site capture consistency measure (SCC).

31. The method of any one of embodiments 1-30, wherein each of the MIPs replicons provided in step b) is produced by:
i) the first and second targeting polynucleotide arms, respectively, hybridizing to the first and second regions in the nucleic acid sample, respectively, wherein the first and second regions flank a target sequence of interest; and
ii) after the hybridization, using a ligation/extension mixture to extend and ligate the gap region between the two targeting polynucleotide arms to form single-stranded circular nucleic acid molecules.

32. The method of any one of embodiments 1-31, wherein each of the MIPs replicons is a single-stranded circular nucleic acid molecule.

33. The method of any one of embodiments 1-32, wherein the sequencing step of c) comprises a next generation sequencing method.

34. The method of embodiment 33, wherein the next generation sequencing method comprises a massive parallel sequencing method, or a massive parallel short-read sequencing method.

35. The method of any one of embodiments 1-34, wherein the method comprises, before the sequencing step of c), a PCR reaction to amplify the MIPs replicons for sequencing.

36. The method of embodiment 35, wherein the PCR reaction is an indexing PCR reaction.

37. The method of embodiment 36, wherein the indexing PCR reaction introduces into each of the MIPs amplicons the following components: a pair of indexing primers, a unique sample barcode and a pair of sequencing adaptors.

38. The method of embodiment 37, wherein the barcoded MIPs amplicons comprise in sequence the following components:

a first sequencing adaptor-a first sequencing primer-the first unique targeting molecular tag-the first targeting polynucleotide arm-captured nucleic acid-the second targeting polynucleotide arm-the second unique targeting molecular tag-a unique sample barcode-a second sequencing primer-a second sequencing adaptor.

39. The method of any one of embodiments 1-38, wherein the first plurality of target sequences of interest is on a single chromosome.

40. The method of any one of embodiments 1-39, wherein the second plurality of target sequences of interest are on multiple chromosomes.

41. The method of any one of embodiments 1-40, wherein the site capture metric determined at step f) is the number of capture events determined at step d), and the site capture metric determined at step h) is the number of capture events determined at step e).

42. The method of any one of embodiments 1-41, further comprising computing a variability coefficient for a plurality of site capture metrics for a particular site, wherein each site capture metric in the plurality of site capture metrics is evaluated from a nucleic acid sample from a different subject, and wherein the at least one criterion used at steps g) and h) includes a requirement that the variability coefficient for the particular site is below a threshold value.

43. The method of any one of embodiments 1-42, wherein the first measure determined at step j) is a sum of the first subset of site capture metric and corresponds to a chromosome of interest, and the second measure determined at step j) is a sum of the second subset of site capture metric and corresponds to chromosomes other than the chromosome of interest.

44. The method of any one of embodiments 1-43, wherein the determining at step l) comprises performing a statistical test to evaluate whether the test ratio obtained at step j) is statistically different from the plurality of reference ratios.

45. The method of any one of embodiments 1-44, wherein the first population of amplicons corresponds to a chromosome of interest.

46. The method of embodiment 45, wherein the second population of amplicons corresponds to chromosomes other than the chromosome of interest.

47. The method of any one of embodiments 1-46, wherein the test ratio and the reference ratios are chromosomal fractions.

48. The method of embodiment 47, wherein the chromosomal fractions are defined by a ratio between a sum of all unique capture events from a chromosome of interest (S1) and a sum of all unique capture events from all chromosomes (S1+S2).

49. The method of any one of embodiments 1-48, wherein the size of the MIP replicon is between 80-90 base pairs.

50. The method of any one of embodiments 1-49, wherein the sequencing step has a read depth of between 6-8 million reads.

51. The method of any one of embodiments 1-50, wherein the target sequence of interest is located in an Alu element.

52. The method of embodiment 51, wherein the target sequence of interest is located in the right arm of an Alu element.

53. The method of any one of embodiments 1-52, wherein the aneuploidy is an autosomal aneuploidy, and the numbers of capture events determined in steps d) and e) exclude any capture events from sex chromosomes.

54. The method of any one of embodiments 1-52, wherein the aneuploidy is a sex chromosome aneuploidy, and the numbers of capture events determined in steps d) and e) include capture events from at least one sex chromosome.

55. A method of detecting aneuploidy in a fetus comprising:

a) obtaining a genomic DNA sample from a maternal blood sample;

b) adding the genomic DNA sample into each well of a multi-well plate, wherein each well of the multi-well plate comprises a probe mixture, wherein the probe mixture comprises a population of molecular inversion probes (MIPs) and a buffer;

wherein each MIP in the population of MIPs comprises in sequence the following components:

first targeting polynucleotide arm-first unique molecular tag-polynucleotide linker-second unique molecular tag-second targeting polynucleotide arm;

wherein the pair of first and second targeting polynucleotide arms in each of the MIPs are identical, and are substantially complementary to first and second regions in the nucleic acid that, respectively, flank each sequence in a plurality of target sequences of interest;

wherein the first and second unique targeting molecular tags in each of the MIPs in combination are distinct in each of the MIPs;

c) incubating the genomic DNA sample with the probe mixture for the MIPs to capture the plurality of target sequences of interest;

d) adding an extension/ligation mixture to the sample of c) for the MIPs and the plurality of target sequences of interest to form a plurality of MIPs amplicons, wherein the extension/ligation mixture comprises a polymerase, a plurality of dNTPs, a ligase, and buffer;

e) adding an exonuclease mixture to the targeting and control MIPs amplicons to remove excess probes or excess genomic DNA;

f) adding an indexing PCR mixture to the sample of e) to add a pair of indexing primers, a unique sample barcode and a pair of sequencing adaptors to the plurality of amplicons;

g) using a massively parallel sequencing method to determine the number of sequencing reads of a first population of barcoded amplicons provided in step f) based on the number of the unique targeting molecular tags, wherein the first population of barcoded amplicons is identified by the sequence of the target sequence of interest;

h) using a massively parallel sequencing method to determine the number of sequencing reads of a second population of barcoded amplicons provided in step f) based on the number of the unique targeting molecular tags, wherein the second population of barcoded amplicons is identified by the sequence of the target sequence of interest;

i) computing a site capture metric based at least in part on the number of first sequencing reads determined in step g) and a plurality of control probe capture metrics based at least in part on the numbers of second sequencing reads determined in step h);

j) identifying a subset of site capture metrics of the population of the MIPs amplicons that have control probe capture metrics satisfying at least one criterion;

k) normalizing the site capture metric by a factor computed from the subset of control probe capture metrics satisfying the at least one criterion, to obtain a test normalized site capture metric;

l) comparing the test normalized site capture metric to a plurality of reference normalized site capture metrics that are computed based on reference genomic DNA samples obtained from reference subjects exhibiting known genotypes using the same target and control sites, target population, subset of control populations in steps b)-h); and m) determining, based on the comparing in step l) and the known genotypes of reference subjects, whether aneuploidy is detected in the fetus.

56. The method of embodiment 55, wherein the blood sample is a whole blood sample, a plasma sample, or a serum sample.

57. The method of embodiment 56, wherein the blood sample is a plasma sample.

58. The method of any one of embodiments 55-57, wherein the length of the first targeting polynucleotide arm is between 14 and 30 base pairs.

59. The method of any one of embodiments 55-58, wherein the length of the second targeting polynucleotide arm is between 14 and 30 base pairs.

60. The method of any one of embodiments 55-59, wherein each of the targeting polynucleotide arms has a melting temperature between 45° C. and 80° C.

61. The method of any one of embodiments 55-60, wherein each of the targeting polynucleotide arms has a GC content between 30% and 80%, or between 30% and 70%.

62. The method of any one of embodiments 55-61, wherein the length of the first unique molecular tag is between 4 and 15 base pairs.

63. The method of any one of embodiments 55-62, wherein the length of the second unique molecular tag is between 4 and 15 base pairs.

64. The method of any one of embodiments 55-63, wherein each of the unique molecular tags has a melting temperature between 45° C. and 80° C.

65. The method of any one of embodiments 55-64, wherein each of the unique molecular tags have a GC content between 30% and 80%, or between 30% and 70%.

66. The method of any one of embodiments 55-65, wherein the polynucleotide linker is not substantially complementary to any genomic region of the subject.

67. The method of any one of embodiments 55-66, wherein the polynucleotide linker has a length of between 20 and 1,000 base pairs.

68. The method of any one of embodiments 55-67, wherein the polynucleotide linker has a melting temperature of between 45° C. and 80° C.

69. The method of any one of embodiments 55-68, wherein the polynucleotide linker has a GC content between 30% and 80%, or between 30% and 70%.

70. The method of any one of embodiments 55-69, wherein the polynucleotide linker comprises at least one amplification primer.

71. The method of embodiment 70, wherein the polynucleotide linker comprises a forward amplification primer and a reverse amplification primer.

72. The method of embodiment 71, wherein the sequence of the forward amplification primer comprises the nucleotide sequence of

5'-CTTCAGCTTCCCGATTACGG-3'.    (SEQ ID NO: 1)

73. The method of embodiment 72, wherein the sequence of the reverse amplification primer comprises the nucleotide sequence of

5'-GCACGATCCGACGGTAGTGT-3'.    (SEQ ID NO: 2)

74. The method of any one of embodiments 55-73, wherein the polynucleotide linker comprises the nucleotide sequence of (SEQ ID NO: 3)
5'-CTTCAGCTTCCCGATTACGGGCACGATCCGACGGTAGTGT-3'.

75. The method of any one of embodiments 55-74, wherein the first targeting polynucleotide arm comprises the nucleotide sequence of

5'-CACTGCACTCCAGCCTGG-3'.    (SEQ ID NO: 4)

76. The method of any one of embodiments 55-75, wherein the second targeting polynucleotide arm comprises the nucleotide sequence of

5'-GAGGCTGAGGCAGGAGAA-3'.    (SEQ ID NO: 5)

77. The method of any one of embodiments 55-76, wherein the MIP comprises the nucleotide sequence of 5'-CACTGCACTCCAGCCTGG($N_{1-6}$)CTTCAGCTTCCC-GATTACGGGCACGATCCGACGGTAGTGT($N_{7-12}$) GAGGCTGAGGCAGGAGAA-3' (SEQ ID NO: 6), wherein ($N_{1-6}$) represents the first unique molecular tag and ($N_{7-12}$) represents the second unique molecular tag.

78. The method of any one of embodiments 55-77, wherein the population of MIPs has a concentration between 10 fM and 100 nM.

79. The method of any one of embodiments 55-78, wherein the size of the MIP replicon is between 80-90 base pairs.

80. The method of any one of embodiments 55-79, wherein the sequencing step has a read depth of between 6-8 million reads.

81. A method of selecting a molecular inversion probe (MIP) from a plurality of candidate MIPs for using to detect aneuploidy in a subject, the method comprising:
a) receiving nucleic acid sequences of the plurality of candidate MIPs;
b) for each respective MIP in the plurality of candidate MIPs,
  i) computing a first number (A) of unique sites predicted, with no mismatch, to be captured by the respective MIP on a chromosome of interest;
  ii) computing a second number (C) of unique sites predicted, with one mismatch, to be captured by the respective MIP on the chromosome of interest;
  iii) computing a third number (E) of unique sites predicted, with no mismatch, to be captured by the respective MIP across a genome;
  iv) computing a fourth number (G) of unique sites predicted, with one mismatch, to be captured by the respective MIP across the genome;
  v) computing a fifth number (F) of non-unique sites predicted, with no mismatch, to be captured by the respective MIP across the genome;
  vi) computing a sixth number (H) of non-unique sites predicted, with one mismatch, to be captured by the respective MIP across the genome;

vii) computing a performance metric for the respective MIP based at least in part on the first, second, third, fourth, fifth, and sixth numbers;

c) selecting a MIP, based at least in part on the performance metric computed in step b)vii) for each MIP in the plurality of candidate MIPs.

82. The method of embodiment 81, wherein a unique site corresponds to a site that is captured by the respective MIP only once.

83. The method of any of embodiments 81-82, wherein a non-unique site corresponds to a site that is captured by the respective MIP more than once.

84. The method of embodiment 83, wherein the non-unique site is captured by the respective MIP more than once on the same chromosome, on different chromosomes, or both.

85. The method of any of embodiments 81-84, wherein the genome includes all autosomes, the X chromosome, and the Y chromosome.

86. The method of any of embodiments 81-85, wherein the MIP at step c) is selected such that a first ratio between the first number (A) and the fifth number (F) is larger than an equivalent ratio for a remaining set of the candidate MIPs.

87. The method of any of embodiments 81-86, wherein the MIP at step c) is selected such that a second ratio between the first number (A) and the third number (E) is larger than an equivalent ratio for a remaining set of the candidate MIPs.

88. The method of any of embodiments 81-87, wherein the MIP at step c) is selected such that a third ratio between the first number (A) and the second number (C) is larger than an equivalent ratio for a remaining set of the candidate MIPs.

89. The method of any of embodiments 81-88, wherein the MIP at step c) is selected such that a fourth ratio between a first sum of the first number (A) and the second number (C) and a second sum of the third, fourth, fifth, and six numbers (E, F, G, H) is larger than an equivalent ratio for a remaining set of the candidate MIPs.

90. The method of any of embodiments 81-89, wherein the MIP at step c) is selected such that a fifth ratio between a first weighted sum of the first number (A) and the second number (C) and a second weighted sum of the third, fourth, fifth, and six numbers (E, F, G, H) is larger than an equivalent ratio for a remaining set of the candidate MIPs.

91. The method of any of embodiments 81-90, wherein the fifth ratio (P1) between the first weighted sum and the second weighted sum is.

$$P1 = \frac{A + K_e C}{(E+F) + K_e(G+H)}$$

92. The method of any of embodiments 81-91, wherein the fifth ratio (P) between the first weighted sum and the second weighted sum is:

$$P = \frac{(A + K_e C)^2}{(E+F) + K_e(G+H)}$$

93. The method of any of embodiments 81-92, wherein selecting the MIP at step c) includes comparing the performance metric to a predetermined threshold.

94. The method of embodiment 93, wherein the MIP that is selected at step c) has a fifth ratio (P) that exceeds 6.

95. The method of any of embodiments 81-94, wherein the MIP at step c) is selected such that a third weighted sum between the first number (A) and the second number (C) is larger than an equivalently weighted sum for a remaining set of the candidate MIPs.

96. The method of embodiments 81-95, wherein the third weighted sum is:

$$P2 = A + K_e C$$

97. The method of any of embodiments 81-96, wherein the MIP at step c) is selected such that a product between the fifth ratio (P1) and the third weighted sum (P2) is larger than an equivalent product for a remaining set of the candidate MIPs.

98. The method of any of embodiments 81-97, wherein the performance metric is calculated based on a total number of useful reads from the chromosome of interest.

99. The method of any of embodiments 81-98, wherein the MIP at step c) is selected based on a ratio ($K_e$) of an average capture coefficient of one mismatch sites ($K_1$) and an average capture coefficient of zero mismatch sites ($K_0$):

$$K_e = \frac{K_1}{K_0}$$

and wherein the ratio ($K_e$) is experimentally estimated.

100. The method of any of embodiments 81-99, wherein the MIP at step c) is selected based on a total molecular tag count (TMTC) defined as:

$$TMTC = K_0(E+F) + K_1(G+H).$$

101. A method of selecting a molecular inversion probe (MIP) from a plurality of candidate MIPs for using to detect aneuploidy in a subject, the method comprising:

a) receiving nucleic acid sequences of the plurality of candidate MIPs;

b) for each respective MIP in the plurality of candidate MIPs, i) computing a first number (A) of unique sites predicted, with no mismatch, to be captured by the respective MIP on a chromosome of interest;

ii) computing a second number (C) of unique sites predicted, with one mismatch, to be captured by the respective MIP on the chromosome of interest;

iii) computing a performance metric for the respective MIP based at least in part on the first and second numbers;

c) selecting a MIP, based at least in part on the performance metric computed in step b) iii) for each MIP in the plurality of candidate MIPs.

102. The method of embodiment 101, wherein a unique site corresponds to a site that is captured by the respective MIP only once.

103. The method of any of embodiments 101-102, wherein a non-unique site corresponds to a site that is captured by the respective MIP more than once.

104. The method of embodiment 103, wherein the non-unique site is captured by the respective MIP more than once on the same chromosome, on different chromosomes, or both.

105. The method of any of embodiments 101-104, wherein the MIP at step c) is selected such that a first ratio between the first number (A) and the second number (C) is larger than an equivalent ratio for a remaining set of the candidate MIPs.

106. A method of selecting a molecular inversion probe (MIP) from a plurality of candidate MIPs for using to detect aneuploidy in a subject, the method comprising:
a) receiving nucleic acid sequences of the plurality of candidate MIPs;
b) for each respective MIP in the plurality of candidate MIPs,
  i) computing a first number (A) of unique sites predicted, with no mismatch, to be captured by the respective MIP on a chromosome of interest;
  ii) computing a second number (F) of non-unique sites predicted, with no mismatch, to be captured by the respective MIP across the genome;
  iii) computing a performance metric for the respective MIP based at least in part on the first and second numbers;
c) selecting a MIP, based at least in part on the performance metric computed in step b) iii) for each MIP in the plurality of candidate MIPs.

107. The method of embodiment 106, wherein a unique site corresponds to a site that is captured by the respective MIP only once.

108. The method of any of embodiments 106-107, wherein a non-unique site corresponds to a site that is captured by the respective MIP more than once.

109. The method of embodiment 108, wherein the non-unique site is captured by the respective MIP more than once on the same chromosome, on different chromosomes, or both.

110. The method of any of embodiments 106-109, wherein the MIP at step c) is selected such that a first ratio between the first number (A) and the second number (F) is larger than an equivalent ratio for a remaining set of the candidate MIPs.

111. The method of any of embodiments 106-110, wherein the genome includes all autosomes, the X chromosome, and the Y chromosome.

112. A method of selecting a molecular inversion probe (MIP) from a plurality of candidate MIPs for using to detect aneuploidy in a subject, the method comprising:
a) receiving nucleic acid sequences of the plurality of candidate MIPs;
b) for each respective MIP in the plurality of candidate MIPs,
  i) computing a first number (A) of unique sites predicted, with no mismatch, to be captured by the respective MIP on a chromosome of interest;
  ii) computing a second number (E) of unique sites predicted, with no mismatch, to be captured by the respective MIP across a genome;
  iii) computing a performance metric for the respective MIP based at least in part on the first and second numbers;
c) selecting a MIP, based at least in part on the performance metric computed in step b) iii) for each MIP in the plurality of candidate MIPs.

113. The method of embodiment 112, wherein a unique site corresponds to a site that is captured by the respective MIP only once.

114. The method of any of embodiments 112-113, wherein a non-unique site corresponds to a site that is captured by the respective MIP more than once.

115. The method of embodiment 114, wherein the non-unique site is captured by the respective MIP more than once on the same chromosome, on different chromosomes, or both.

116. The method of any of embodiments 112-115, wherein the MIP at step c) is selected such that a first ratio between the first number (A) and the second number (E) is larger than an equivalent ratio for a remaining set of the candidate MIPs.

117. The method of any of embodiments 112-116, wherein the genome includes all autosomes, the X chromosome, and the Y chromosome.

118. A nucleic acid molecule comprising a nucleotide sequence of 5'-CACTGCACTCCAGCCTGG($N_{1-6}$)CTTCAGCTTCCCGATTACGGGCAC-GATCCGACGGTAGTGT($N_{7-12}$)GAGGCTGAGGCAG-GAGAA-3' (SEQ ID NO: 6), wherein ($N_{1-6}$) represents a first unique molecular tag and ($N_{7-12}$) represents a second unique molecular tag.

119. The nucleic acid of embodiment 118, wherein the length of the first unique molecular tag is between 4 and 15 base pairs.

120. The nucleic acid of any one of embodiments 118-119, wherein the length of the second unique molecular tag is between 4 and 15 base pairs.

121. The nucleic acid of any one of embodiments 118-120, wherein each of the unique targeting molecular tags has a melting temperature between 45° C. and 80° C.

122. The nucleic acid of any one of embodiments 118-121, wherein each of the unique targeting molecular tags have a GC content between 30% and 80% or between 30% and 70%.

123. A nucleic acid molecule comprising a nucleotide sequence of

5'-A-(N)x-B-(N)y-C-3', wherein (N)x represents a first unique molecular tag and (N)y represents a second unique molecular tag, and wherein X and Y are between 4 and 15 base pairs,
wherein A i) comprises the sequence of 5'-TGCACTCCAGCCTG-3' (SEQ ID NO: 15), or a sequence that is at least 85% similar to the sequence of 5'-TGCACTCCAGCCTG-3'(SEQ ID NO: 15); and ii) has a length of no more than 30 base pairs,
wherein C i) comprises the sequence of 5'-GAGGCT-GAGGCAGGA-3' (SEQ ID NO: 16), or a sequence that is at least 85% similar to the sequence of 5'-GAGGCT-GAGGCAGGA-3' (SEQ ID NO: 16); and ii) has a length of no more than 30 base pairs.

124. A nucleic acid molecule comprising a nucleotide sequence of

5'-A-(N)x-B-(N)y-C-3', wherein (N)x represents a first unique molecular tag and (N)y represents a second unique molecular tag, and wherein X and Y are between 4 and 15 base pairs,
wherein A i) comprises the sequence of 5'-TCCTGCCTCAGCCTC-3' (SEQ ID NO: 17), or a sequence that is at least 85% similar to the sequence of 5'-TCCTGCCTCAGCCTC-3' (SEQ ID NO: 17); and ii) has a length of no more than 30 base pairs, and
wherein C i) comprises the sequence of 5'-AGGCTG-GAGTGC-3' (SEQ ID NO: 18), or a sequence that is at least 85% similar to the sequence of 5'-AGGCTGGAGTGC-3' (SEQ ID NO: 18); and ii) has a length of no more than 30 base pairs.

125. The nucleic acid molecule of embodiment 123 or 124, wherein B comprises the sequence of 5'-CTTCAGCTTCCCGATTACGGGCAC-GATCCGACGGTAGTGT-3' (SEQ ID NO: 3), or a sequence that is at least 85% similar to the sequence of (SEQ ID NO: 3)
5'-CTTCAGCTTCCCGATTACGGGCACGATCCGACGGTAGTGT-3'.

126. The nucleotide acid molecule of any one of embodiments 123-125, wherein A or C has a melting temperature between 45° C. and 80° C.

127. The nucleotide acid molecule of any one of embodiments 123-126, wherein A or C has a GC content between 30% and 80%, or between 30% and 70%.

128. A nucleic acid molecule comprising a nucleotide sequence of (SEQ ID NO: 19)
5'-CCACTGCACTCCAGCCTG($N_{1-6}$)

CTTCAGCTTCCCGATTACGGGCACGATCCGACGGTAGTGT ($N_{1-6}$)

GAGGCTGAGGCAGGAGAA-3', wherein ($N_{1-6}$) represents a first unique molecular tag and ($N_{7-12}$) represents a second unique molecular tag.

129. A nucleic acid molecule comprising a nucleotide sequence of (SEQ ID NO: 20)
5'-TCTCCTGCCTCAGCCTCC($N_{1-6}$)

CTTCAGCTTCCCGATTACGGGCACGATCCGACGGTAGTGT ($N_{7-12}$)

AGGCTGGAGTGCAGTGGC-3', wherein ($N_{1-6}$) represents a first unique molecular tag and ($N_{7-12}$) represents a second unique molecular tag.

130. A nucleic acid molecule comprising a nucleotide sequence of (SEQ ID NO: 21)
5'-CACTGCACTCCAGCCTGG($N_{1-6}$)

CTTCAGCTTCCCGATTACGGGCACGATCCGACGGTAGTGT ($N_{7-12}$)

GAGGCTGAGGCAGGAGAA-3', wherein ($N_{1-6}$) represents a first unique molecular tag and ($N_{7-12}$) represents a second unique molecular tag.

131. A nucleic acid molecule comprising a nucleotide sequence of (SEQ ID NO: 22)
5'-CACTGCACTCCAGCCTGG($N_{1-6}$)

CTTCAGCTTCCCGATTACGGGCACGATCCGACGGTAGTGT ($N_{7-12}$)

GAGGCTGAGGCAGGAGAA-3', wherein ($N_{1-6}$) represents a first unique molecular tag and ($N_{7-12}$) represents a second unique molecular tag.

132. A nucleic acid molecule comprising a nucleotide sequence of (SEQ ID NO: 23)
5'-CCACTGCACTCCAGCCTG($N_{1-6}$)

CTTCAGCTTCCCGATTACGGGCACGATCCGACGGTAGTGT ($N_{7-12}$)

GGAGGCTGAGGCAGGAGA-3', wherein ($N_{1-6}$) represents a first unique molecular tag and ($N_{7-12}$) represents a second unique molecular tag.

133. A nucleic acid molecule comprising a nucleotide sequence of (SEQ ID NO: 24)
5'-CACTGCACTCCAGCCTGG($N_{1-6}$)

CTTCAGCTTCCCGATTACGGGCACGATCCGACGGTAGTGT ($N_{7-12}$)

CAGGAGGCTGAGGCAGGA-3', wherein ($N_{1-6}$) represents a first unique molecular tag and ($N_{7-12}$) represents a second unique molecular tag.

134. A nucleic acid molecule comprising a nucleotide sequence of 5'-ACTGCACTCCAGCCTGG($N_{1-6}$) CTTCAGCTTCCCGATTACGGGCAC-GATCCGACGGTAGTGT($N_{7-12}$) GGAGGCTGAGGCAG-GAG-3'(SEQ ID NO: 25), wherein ($N_{1-6}$) represents a first unique molecular tag and ($N_{7-12}$) represents a second unique molecular tag.

135. A nucleic acid molecule comprising a nucleotide sequence of 5'-TGCACTCCAGCCTGGGCA($N_{1-6}$) CTTCAGCTTCCCGATTACGGGCAC-GATCCGACGGTAGTGT($N_{7-12}$) GAGGCTGAGGCAG-GAGAA-3'(SEQ ID NO: 26), wherein ($N_{1-6}$) represents a first unique molecular tag and ($N_{7-12}$) represents a second unique molecular tag.

136. A nucleic acid molecule comprising a nucleotide sequence of 5'-CTGCACTCCAGCCTGGGC($N_{1-6}$) CTTCAGCTTCCCGATTACGGGCAC-GATCCGACGGTAGTGT($N_{7-12}$) GAGGCTGAGGCAG-GAGAA-3' (SEQ ID NO: 27), wherein ($N_{1-6}$) represents a first unique molecular tag and ($N_{7-12}$) represents a second unique molecular tag.

137. The method of any one of embodiments 1-80, wherein the MIP comprises the nucleic acid molecule of any one of embodiments 123-136.

DETAILED DESCRIPTION OF THE INVENTION

Figure 1:
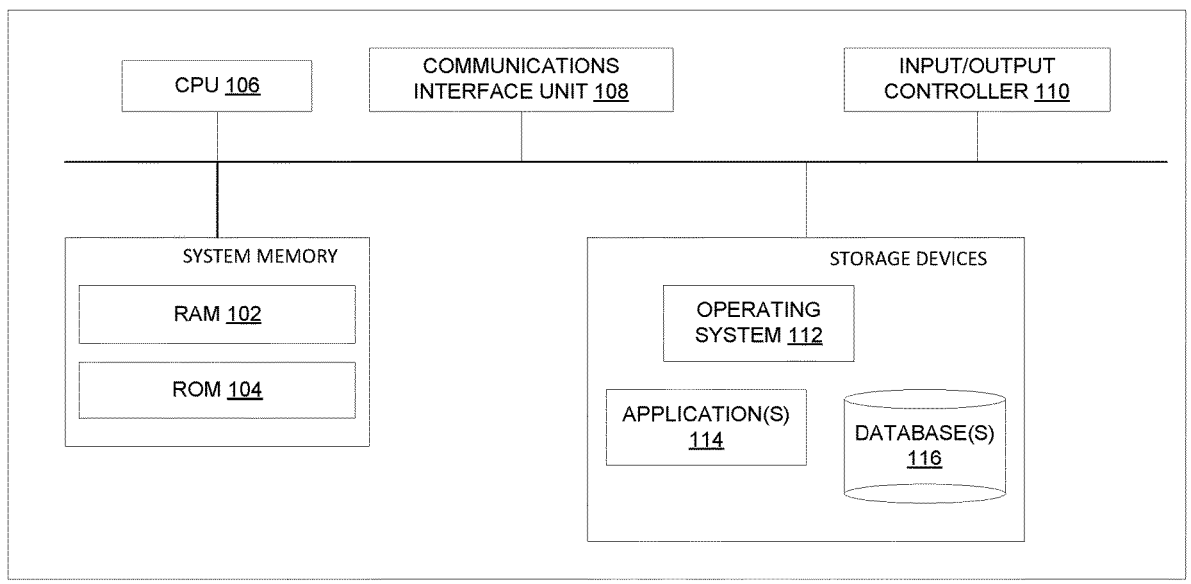
FIG. 1 is an illustrative embodiment of a computing device for performing any of the processes as described in accordance with the methods of the disclosure.

This disclosure provides a system and method for detecting aneuploidy.

In order that the disclosure herein described may be fully understood, the following details description is set forth.

Unless otherwise defined herein, scientific and technical terms used in this application shall have the meanings that are commonly understood by those of ordinary skill in the art to which this disclosure belongs. Generally, nomenclature used in connection with, and techniques of, cell and tissue culture, molecular biology, cell biology, cancer biology, neurobiology, neurochemistry, virology, immunology, microbiology, genetics, protein and nucleic acid chemistry, chemistry, and pharmacology described herein, are those well known and commonly used in the art. Each embodiment of the disclosure described herein may be taken alone or in combination with one or more other embodiments of the disclosure.

The methods and techniques of the present disclosure are generally performed, unless otherwise indicated, according to methods of molecular biology, cell biology, biochemistry, microarray and sequencing technology well known in the art and as described in various general and more specific references that are cited and discussed throughout this specification. See, e.g. Motulsky, "Intuitive Biostatistics", Oxford University Press, Inc. (1995); Lodish et al., "Molecular Cell Biology, 4th ed.", W. H. Freeman & Co., New York (2000); Griffiths et al., "Introduction to Genetic Analysis, 7th ed.", W. H. Freeman & Co., N.Y. (1999); Gilbert et al., "Developmental Biology, 6th ed.", Sinauer Associates, Inc., Sunderland, Mass. (2000).

Chemistry terms used herein are used according to conventional usage in the art, as exemplified by "The McGraw-Hill Dictionary of Chemical Terms", Parker S., Ed., McGraw-Hill, San Francisco, Calif. (1985).

All of the above, and any other publications, patents and published patent applications referred to in this application are specifically incorporated by reference herein. In case of conflict, the present specification, including its specific definitions, will control.

Throughout this specification, the word "comprise" or variations such as "comprises" or "comprising" will be understood to imply the inclusion of a stated integer (or components) or group of integers (or components), but not the exclusion of any other integer (or components) or group of integers (or components).

The singular forms "a," "an," and "the" include the plurals unless the context clearly dictates otherwise.

The term "including" is used to mean "including but not limited to". "Including" and "including but not limited to" are used interchangeably.

In order to further define the disclosure, the following terms and definitions are provided herein.

Definitions

The term "aneuploidy," as used herein, refers to a chromosomal abnormality characterized by an abnormal variation in chromosome number, e.g., a number of chromosomes that is not an exact multiple of the haploid number of chromosomes. For example, a euploid individual will have a number of chromosomes equaling 2n, where n is the number of chromosomes in the haploid individual. In humans, the haploid number is 23. Thus, a diploid individual will have 46 chromosomes. An aneuploid individual may contain an extra copy of a chromosome (trisomy of that chromosome) or lack a copy of the chromosome (monosomy of that chromosome). The abnormal variation is with respect to each individual chromosome. Thus, an individual with both a trisomy and a monosomy is aneuploid despite having 46 chromosomes. Examples of aneuploidy diseases or conditions include, but are not limited to, Down syndrome (trisomy of chromosome 21), Edwards syndrome (trisomy of chromosome 18), Patau syndrome (trisomy of chromosome 13), Turner syndrome (monosomy of the X chromosome in a female), and Klinefelter syndrome (an extra copy of the X chromosome in a male). Other, non-aneuploid chromosomal abnormalities include translocation (wherein a segment of a chromosome has been transferred to another chromosome), deletion (wherein a piece of a chromosome has been lost), and other types of chromosomal damage (e.g., Fragile X syndrome, which is caused by an X chromosome that is abnormally susceptible to damage).

In other embodiments of the disclosure, the methods may be used to detect copy number variations. As used herein a "copy number variation" generally is a class or type of genetic variation or chromosomal aberration. A copy number variation can be a deletion (e.g. micro-deletion), duplication (e.g., a micro-duplication), or insertion (e.g., a micro-insertion). In certain embodiments, the prefix "micro" as used herein may refer to a segment of a nucleic acid less than 5 base pairs in length. A copy number variation can include one or more deletions (e.g. micro-deletion), duplications and/or insertions (e.g., a micro-duplication, micro-insertion) of a segment of a chromosome. In certain embodiments a duplication comprises an insertion. In certain embodiments an insertion is a duplication. In certain embodiments an insertion is not a duplication. For example, a duplication of a sequence in a portion increases the counts for a portion in which the duplication is found. Often a duplication of a sequence in a portion increases the elevation or level. In certain embodiments, a duplication present in portions making up a first elevation or level increases the elevation or level relative to a second elevation or level where a duplication is absent. In certain embodiments an insertion increases the counts of a portion and a sequence representing the insertion is present (i.e., duplicated) at another location within the same portion. In certain embodiments an insertion does not significantly increase the counts of a portion or elevation or level and the sequence that is inserted is not a duplication of a sequence within the same portion. In certain embodiments an insertion is not detected or represented as a duplication and a duplicate sequence representing the insertion is not present in the same portion. In some embodiments a copy number variation is a fetal copy number variation. Often, a fetal copy number variation is a copy number variation in the genome of a fetus. In some embodiments a copy number variation is a maternal and/or fetal copy number variation. In certain embodiments a maternal and/or fetal copy number variation is a copy number variation within the genome of a pregnant female (e.g., a female subject bearing a fetus), a female subject that gave birth or a female capable of bearing a fetus. A copy number variation can be a heterozygous copy number variation where the variation (e.g., a duplication or deletion) is present on one allele of a genome. A copy number variation can be a homozygous copy number variation where the variation is present on both alleles of a genome. In some embodiments a copy number variation is a heterozygous or homozygous fetal copy number variation. In some embodiments a copy number variation is a heterozygous or homozygous maternal and/or fetal copy number variation. A copy number variation sometimes is present in a maternal genome and a fetal genome, a maternal genome and not a fetal genome, or a fetal genome and not a maternal genome.

The terms "subject" and "patient", as used herein, refer to any animal, such as a dog, a cat, a bird, livestock, and particularly a mammal, and preferably a human. The term "reference subject" and "reference patients" refer to any subject or patient that exhibit known genotypes (e.g., known euploidy or aneuploidy).

The terms "polynucleotide", "nucleic acid" and "nucleic acid molecules", as used herein, are used interchangeably and refer to DNA molecules (e.g., cDNA or genomic DNA), RNA molecules (e.g., mRNA), DNA-RNA hybrids, and analogs of the DNA or RNA generated using nucleotide analogs. The nucleic acid molecule can be a nucleotide, oligonucleotide, double-stranded DNA, single-stranded DNA, multi-stranded DNA, complementary DNA, genomic DNA, non-coding DNA, messenger RNA (mRNAs), microRNA (miRNAs), small nucleolar RNA (snoRNAs), ribosomal RNA (rRNA), transfer RNA (tRNA), small interfering RNA (siRNA), heterogeneous nuclear RNAs (hnRNA), or small hairpin RNA (shRNA).

The term "sample", as used herein, refers to a sample typically derived from a biological fluid, cell, tissue, organ, or organism, comprising a nucleic acid or a mixture of nucleic acids comprising at least one nucleic acid sequence that is to be screened for, e.g., aneuploidy or other chromosomal abnormalities. In some embodiments, a sample is a blood sample such as a whole blood sample, a serum sample, or a plasma sample. In some embodiments the sample comprises at least one nucleic acid sequence whose genome is suspected of having undergone variation. Such samples include, but are not limited to sputum/oral fluid, amniotic fluid, blood, a blood fraction, or fine needle biopsy samples (e.g., surgical biopsy, fine needle biopsy, etc.) urine, peritoneal fluid, pleural fluid, and the like. Although the sample is often taken from a human subject (e.g., patient), the assays can be used to detect aneuploidy in samples from any mammal, including, but not limited to dogs, cats, horses, goats, sheep, cattle, pigs, etc. The sample may be used directly as obtained from the biological source or following a pretreatment to modify the character of the sample. For example, such pretreatment may include preparing plasma from blood, diluting viscous fluids and so forth. Methods of pretreatment may also involve, but are not limited to, filtration, precipitation, dilution, distillation, mixing, centrifugation, freezing, lyophilization, concentration, amplification, nucleic acid fragmentation, inactivation of interfering components, the addition of reagents, lysing, etc. If such methods of pretreatment are employed with respect to the sample, such pretreatment methods are typically such that the nucleic acid(s) of interest remain in the test sample, preferably at a concentration proportional to that in an untreated test sample (e.g., namely, a sample that is not subjected to any such pretreatment method(s)). Depending on the type of sample used, additional processing and/or purification steps may be performed to obtain nucleic acid fragments of a desired purity or size, using processing methods including but not limited to sonication, nebulization, gel purification, PCR purification systems, nuclease cleavage, size-specific capture or exclusion, targeted capture or a combination of these methods. Optionally, cell-free DNA may be isolated from the sample prior to further analysis. In some embodiments, the sample is from the subject whose euploidy or aneuploidy is to be determined by the systems and methods of the disclosure, also referred as "a test sample."

The term "MIP," as used herein, refers to a molecular inversion probe (also known as a circular capture probe). As used herein, the term "primer" or "probe" also may refer to a MIP. Molecular inversion probes are nucleic acid molecules that contain two targeting polynucleotide arms, one or more unique molecular tags (also known as unique molecular identifiers), and a polynucleotide linker (e.g., a universal backbone linker). See, for example, FIG. 5. In some embodiments, a MIP may comprise more than one unique molecular tags, such as, two unique molecular tags, three unique molecular tags, or more. In some embodiments, the unique polynucleotide arms in each MIP are located at the 5' and 3' ends of the MIP, while the unique molecular tag(s) and the polynucleotide linker are located in the middle. For example, the MIPs that are used in the disclosure comprise in sequence the following components: first targeting polynucleotide arm-first unique molecular tag-polynucleotide linker-second unique molecular tag-second targeting polynucleotide arm. In some embodiments, the polynucleotide linker (or the backbone linker) in the MIPs are universal in all the MIPs used in a method of the disclosure.

In the MIPs, the unique polynucleotide arms are designed to hybridize immediately upstream and downstream of a specific target sequence (or site) of interest in a genomic nucleic acid sample. As used herein, the terms "target sequence of interest" and "target site of interest" are used interchangeably to refer to a portion of a genomic nucleic acid molecule that a MIP is designed to capture. In some embodiments, the unique polynucleotide arms are complementary to the immediate upstream and downstream of one or more sequences of interest (or sites of interest) in a genomic nucleic acid sample. In some embodiments, these unique polynucleotide arms are complementary to one or more sequences of interest (or sites of interest) in a genomic nucleic acid sample. In some embodiments, the targeting polynucleotide arms comprise a ligation sequence and an extension sequence. A MIP that comprises targeting polynucleotide arms that are complementary to a plurality of sequences of interest in a DNA sample may be referred to as a "repeat offender-MIP" or "RO-MIP." For example, a RO-MIP can target hundreds, thousands, hundreds of thousands, or millions of sequences of interest in a DNA sample (e.g., a sample comprising a human genome). In some embodiments, a RO-MIP targets, for example, greater than 1,000, greater than 10,000, greater than 20,000, greater than 30,000, greater than 40,000, greater than 50,000, greater than 60,000, greater than 70,000, greater than 80,000, greater than 90,000, greater than 100,000, greater than 200,000, greater than 300,000, greater than 400,000, greater than 500,000, greater than 600,000, greater than 700,000, greater than 800,000, greater than 900,000, and/or greater than 1,000,000 sequences of interest. In some embodiments, a RO-MIP targets, for example, greater than 100,000, greater than 110,000, greater than 120,000, greater than 130,000, greater than 140,000, greater than 150,000, greater than 160,000, greater than 170,000, greater than 180,000, greater than 190,000, and/or greater than 200,000 sequences of interest, or any ranges between 100,000 and 200,000 sequences of interest. In some embodiments, a RO-MIP targets 140,000-160,000 sequences of interest. These sequences of interest may be flanked by repeat sequences to which the targeting polynucleotide arms hybridize. In certain embodiments, the repeat sequences have 0, 1, 2, 3, 4, or more mismatches in hybridizing with the targeting polynucleotide arms. In specific embodiments, the repeat sequences have 0 or 1 mismatches in hybridizing with the targeting polynucleotide arms. In some embodiments, a RO-MIP does not bind long interspersed nucleotide elements (LINE) in the genome.

In some embodiments, the unique molecular tags are short nucleotide sequences that are randomly generated. In certain embodiments, the unique molecular tags do not hybridize to any sequence or site located on a genomic nucleic acid fragment or in a genomic nucleic acid sample. In certain embodiments, the unique molecular tag is any tag with a suitable detectable label that can be incorporated into or attached to a nucleic acid (e.g., a polynucleotide) that allows detection and/or identification of nucleic acids that comprise or attach to the tag. In some embodiments the tag is incorporated into or attached to a nucleic acid during a sequencing method (e.g., by a polymerase). Non-limiting examples of tags include nucleic acid tags, nucleic acid indexes or barcodes, a radiolabel (e.g., an isotope), metallic label, a fluorescent label, a chemiluminescent label, a phosphorescent label, a fluorophore quencher, a dye, a protein (e.g., an enzyme, an antibody or part thereof, a linker, a member of a binding pair), the like or combinations thereof. In some embodiments the tag (e.g., a nucleic acid index or barcode) is a unique, known and/or identifiable sequence of nucleotides or nucleotide analogues. In some embodiments tags are six or more contiguous nucleotides. A multitude of fluorophores are available with a variety of different excitation and emission spectra. Any suitable type and/or number of fluorophores can be used as a tag. In some embodiments 1 or more, 2 or more, 3 or more, 4 or more, 5 or more, 6 or more, 7 or more, 8 or more, 9 or more, 10 or more, 20 or more, 30 or more, 50 or more, 100 or more, 500 or more, 1000 or more, 10,000 or more, 100,000 or more different tags are utilized in a method described herein (e.g., a nucleic acid detection and/or sequencing method). In some embodiments, one or two types of tags (e.g., fluorescent labels) are linked to each nucleic acid in a library. In some embodiments, chromosome-specific tags are used to make chromosomal counting faster or easier. Detection and/or quantification of a tag can be performed by a suitable method, machine or apparatus, non-limiting examples of which include flow cytometry, quantitative polymerase chain reaction (qPCR), gel electrophoresis, a luminometer, a fluorometer, a spectrophotometer, a suitable gene-chip or microarray analysis, Western blot, mass spectrometry, chromatography, cytofluorimetric analysis, fluorescence microscopy, a suitable fluorescence or digital imaging method, confocal laser scanning microscopy, laser scanning cytometry, affinity chromatography, manual batch mode separation, electric field suspension, a suitable nucleic acid sequencing method and/or nucleic acid sequencing apparatus, the like and combinations thereof. In particular embodiments, the tag is suitable for use with microarray analysis.

The MIPs are introduced to nucleic acids (e.g., nucleic acid fragments) to perform capture of target sequences or sites located on a nucleic acid sample (e.g., a genomic DNA). In some embodiments, for example, if genomic DNA is present in a sample, fragmenting may aid in capture of target nucleic acid by molecular inversion probes. As described in greater detail herein, after capture of the target sequence (e.g., locus) of interest, the captured target may further be subjected to an enzymatic gap-filling and ligation step, such that a copy of the target sequence is incorporated into a circle. Capture efficiency of the MIP to the target sequence on the nucleic acid fragment can be improved by lengthening the hybridization and gap-filing incubation periods. (See, e.g., Turner E H, et al., Nat Methods. 2009 Apr. 6:1-2).

MIP technology may be used to detect or amplify particular nucleic acid sequences in complex mixtures. One of the advantages of using the MIP technology is in its capacity for a high degree of multiplexing, which allows thousands of target sequences to be captured in a single reaction containing thousands of MIPs. Various aspects of MIP technology are described in, for example, Hardenbol et al., "Multiplexed genotyping with sequence-tagged molecular inversion probes," Nature Biotechnology, 21(6): 673-678 (2003); Hardenbol et al., "Highly multiplexed molecular inversion probe genotyping: Over 10,000 targeted SNPs genotyped in a single tube assay," Genome Research, 15: 269-275 (2005); Burmester et al., "DMET microarray technology for pharmacogenomics-based personalized medicine," Methods in Molecular Biology, 632: 99-124 (2010); Sissung et al., "Clinical pharmacology and pharmacogenetics in a genomics era: the DMET platform," Pharmacogenomics, 11(1): 89-103 (2010); Deeken, "The Affymetrix DMET platform and pharmacogenetics in drug development," Current Opinion in Molecular Therapeutics, 11(3): 260-268 (2009); Wang et al., "High quality copy number and genotype data from FFPE samples using Molecular Inversion Probe (MIP) microarrays," BMC Medical Genomics, 2:8 (2009); Wang et al., "Analysis of molecular inversion probe performance for allele copy number determination," Genome Biology, 8(11): R246 (2007); Ji et al., "Molecular inversion probe analysis of gene copy alternations reveals distinct categories of colorectal carcinoma," Cancer Research, 66(16): 7910-7919 (2006); and Wang et al., "Allele quantification using molecular inversion probes (MIP)," Nucleic Acids Research, 33(21): e183 (2005), each of which is hereby incorporated by reference in its entirety for all purposes. See also in U.S. Pat. Nos. 6,858,412; 5,817,921; 6,558,928; 7,320,860; 7,351,528; 5,866,337; 6,027,889 and 6,852,487, each of which is hereby incorporated by reference in its entirety for all purposes.

MIP technology has previously been successfully applied to other areas of research, including the novel identification and subclassification of biomarkers in cancers. See, e.g., Brewster et al., "Copy number imbalances between screen- and symptom-detected breast cancers and impact on disease-free survival," Cancer Prevention Research, 4(10): 1609-1616 (2011); Geiersbach et al., "Unknown partner for USP6 and unusual SS18 rearrangement detected by fluorescence in situ hybridization in a solid aneurysmal bone cyst," Cancer Genetics, 204(4): 195-202 (2011); Schiffman et al., "Oncogenic BRAF mutation with CDKN2A inactivation is characteristic of a subset of pediatric malignant astrocytomas," Cancer Research, 70(2): 512-519 (2010); Schiffman et al., "Molecular inversion probes reveal patterns of 9p21 deletion and copy number aberrations in childhood leukemia," Cancer Genetics and Cytogenetics, 193(1): 9-18 (2009); Press et al., "Ovarian carcinomas with genetic and epigenetic BRCA1 loss have distinct molecular abnormalities," BMC Cancer, 8:17 (2008); and Deeken et al., "A pharmacogenetic study of docetaxel and thalidomide in patients with castration-resistant prostate cancer using the DMET genotyping platform," Pharmacogenomics, 10(3): 191-199 (2009), each of which is hereby incorporated by reference in its entirety for all purposes.

MIP technology has also been applied to the identification of new drug-related biomarkers. See, e.g., Caldwell et al., "CYP4F2 genetic variant alters required warfarin dose," Blood, 111(8): 4106-4112 (2008); and McDonald et al., "CYP4F2 Is a Vitamin K1 Oxidase: An Explanation for Altered Warfarin Dose in Carriers of the V433M Variant," Molecular Pharmacology, 75: 1337-1346 (2009), each of which is hereby incorporated by reference in its entirety for all purposes. Other MIP applications include drug development and safety research. See, e.g., Mega et al., "Cytochrome P-450 Polymorphisms and Response to Clopidogrel," New England Journal of Medicine, 360(4): 354-362 (2009); Dumaual et al., "Comprehensive assessment of metabolic enzyme and transporter genes using the Affymetrix Targeted Genotyping System," Pharmacogenomics, 8(3): 293-305 (2007); and Daly et al., "Multiplex assay for comprehensive genotyping of genes involved in drug metabolism, excretion, and transport," Clinical Chemistry, 53(7): 1222-1230 (2007), each of which is hereby incorporated by reference in its entirety for all purposes. Further applications of MIP technology include genotype and phenotype databasing. See, e.g., Man et al., "Genetic Variation in Metabolizing Enzyme and Transporter Genes: Comprehensive Assessment in 3 Major East Asian Subpopulations With Comparison to Caucasians and Africans," Journal of Clinical Pharmacology, 50(8): 929-940 (2010), which is hereby incorporated by reference in its entirety for all purposes.

The term "capture" or "capturing", as used herein, refers to the binding or hybridization reaction between a molecular inversion probe and the corresponding targeting site.

The term "sensitivity", as used herein, refers to a statistical measure of performance of an assay (e.g., method, test), calculated by dividing the number of true positives by the sum of the true positives and the false negatives.

The term "specificity", as used herein, refers to a statistical measure of performance of an assay (e.g., method, test), calculated by dividing the number of true negatives by the sum of true negatives and false positives.

The term "MIP replicon" or "circular replicon", as used herein, refers to a circular nucleic acid molecule generated via a capturing reaction (e.g., a binding or hybridization reaction between a MIP and its targeted sequence). In some embodiments, the MIP replicon is a single-stranded circular nucleic acid molecule. In some embodiments, a targeting MIP captures or hybridizes to a target sequence or site. After the capturing reaction or hybridization, a ligation/extension mixture is introduced to extend and ligate the gap region between the two targeting polynucleotide arms to form single-stranded circular nucleotide molecules, i.e., a targeting MIP replicon. MIP replicons may be amplified through a polymerase chain reaction (PCR) to produce a plurality of targeting MIP amplicons, which are double-stranded nucleotide molecules.

The term "amplicon", as used herein, refers to a nucleic acid generated via amplification reaction. In some embodiments, the amplicon is a single-stranded nucleic acid molecule. In some embodiments, the amplicon is a single-stranded circular nucleic acid molecule. In some embodiments, the amplicon is a double-stranded nucleic acid molecule. For example, a MIP (e.g., a RO-MIP) captures or hybridizes to a target sequence or site. After the capturing reaction or hybridization, a ligation/extension mixture is introduced to extend and ligate the gap region between the two targeting polynucleotide arms to form a single-stranded circular nucleotide molecule, i.e., a MIP replicon. The MIP replicon may be amplified through a polymerase chain reaction (PCR) to produce a plurality of MIP amplicons, which are double-stranded nucleotide molecules. MIP replicons and amplicons can be produced from a first plurality of target sequences of interest (e.g., a chromosome being tested for aneuploidy) and a second plurality of target sequences of interest (e.g., target sequences distributed throughout the genome).

The term "sequencing", as used herein, is used in abroad sense and may refer to any technique known in the art that allows the order of at least some consecutive nucleotides in at least part of a nucleic acid to be identified, including without limitation at least part of an extension product or a vector insert. Sequencing also may refer to a technique that allows the detection of differences between nucleotide bases in a nucleic acid sequence. Exemplary sequencing techniques include targeted sequencing, single molecule real-time sequencing, electron microscopy-based sequencing, transistor-mediated sequencing, direct sequencing, random shotgun sequencing, Sanger dideoxy termination sequencing, targeted sequencing, exon sequencing, whole-genome sequencing, sequencing by hybridization (e.g., in an array such as a microarray), pyrosequencing, capillary electrophoresis, gel electrophoresis, duplex sequencing, cycle sequencing, single-base extension sequencing, solid-phase sequencing, high-throughput sequencing, massively parallel signature sequencing, emulsion PCR, co-amplification at lower denaturation temperature-PCR (COLD-PCR), multiplex PCR, sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, ion semiconductor sequencing, nanoball sequencing, nanopore sequencing, 454 sequencing, Solexa Genome Analyzer sequencing, miSeq (Illumina), HiSeq 2000 (Illumina), HiSeq 2500 (Illumina), Illumina Genome Analyzer (Illumina), Ion Torrent PGM™ (Life Technologies), MinION™ (Oxford Nanopore Technologies), real-time SMRT™ technology (Pacific Biosciences), the Probe-Anchor Ligation (cPAL™) (Complete Genomics/BGI), SOLiD® sequencing, MS-PET sequencing, mass spectrometry, and a combination thereof. In some embodiments, sequencing comprises detecting the sequencing product using an instrument, for example but not limited to an ABI PRISM® 377 DNA Sequencer, an ABI PRISM® 310, 3100, 3100-Avant, 3730, or 373OxI Genetic Analyzer, an ABI PRISM® 3700 DNA Analyzer, or an Applied Biosystems SOLiD™ System (all from Applied Biosystems), a Genome Sequencer 20 System (Roche Applied Science), or a mass spectrometer. In certain embodiments, sequencing comprises emulsion PCR. In certain embodiments, sequencing comprises a high throughput sequencing technique, for example but not limited to, massively parallel signature sequencing (MPSS).

The methods and apparatus described herein may alternatively employ microarray technology to quantify RO-MIPs products. "Microarray" or "array" refers to a solid phase support having a surface, preferably but not exclusively a planar or substantially planar surface, which carries an array of sites containing nucleic acids such that each site of the array comprises substantially identical or identical copies of oligonucleotides or polynucleotides and is spatially defined and not overlapping with other member sites of the array; that is, the sites are spatially discrete. The array or microarray can also comprise a non-planar interrogatable structure with a surface such as a bead or a well. The oligonucleotides or polynucleotides of the array may be covalently bound to the solid support, or may be non-covalently bound. Conventional microarray technology is reviewed in, e.g., Schena, Ed., Microarrays: A Practical Approach, IRL Press, Oxford (2000). "Array analysis", "analysis by array" or "analysis by microarray" refers to analysis, such as, e.g., sequence analysis, of one or more biological molecules using a microarray. In some embodiments each sample is hybridized individually to a single microarray. In other embodiments, processing through-put can be enhanced by physically connecting multiple microarrays onto a single multi-microarray plate for convenient high-throughput handling. In certain embodiments, custom DNA microarrays, for example from Affymetrix Inc. (Santa Clara, Calif., USA), can be manufactured to specifically quantify products of the RO-MIPs assay.

It will be understood by one of ordinary skill in the art that the compositions and methods described herein may be adapted and modified as is appropriate for the application being addressed and that the compositions and methods described herein may be employed in other suitable applications, and that such other additions and modifications will not depart from the scope hereof.

This disclosure will be better understood from the Experimental Details which follow. However, one skilled in the art will readily appreciate that the specific methods and results discussed are merely illustrative of the disclosure as described more fully in the embodiments which follow thereafter.

Methods for Detecting Diseases or Conditions

Existing sequencing methods employ laborious sequencing library preparation steps, require tens of millions of reads to achieve useful coefficients of variation, and can lose validity if the fetal fraction in the sample falls below 4%. Non-targeted "shotgun" methods inherently require large numbers of reads to achieve coverage of desired regions in chromosomes relevant to human aneuploidy. Targeted methods require the manipulation of a large number of PCR primers and multiplexing. Methods using a single primer pair in PCR amplification of repeat regions in library preparation may suffer from PCR artifacts producing ambiguities (interference) in product sequences, lowering the proportion of uniquely mapping reads and overall efficiency.

Embodiments of the present disclosure provide a solution to the problems of existing sequencing methods to detect aneuploidy. These embodiments replace previous library preparations with a capture method using a small number of oligonucleotide MIPs comprising targeting polynucleotide arms that hybridize to repeat sequences, said arms being arms attached to high performance universal backbone structures. These MIPs are designed to flank and incorporate uniquely aligning sequences over the entire human genome, but are enriched for targets pertinent to the detection of common aneuploidies (e.g., trisomy of chromosome 21, 18, or 13). Contemplated methods of selecting capture molecules treat the need to select unique sequences in a desired area for quantitation, and not to rely on the presence of some unique sequences in the amplification of convenient repeat sequences.

The use of repeat sequences (i.e., "repeat offenders") in the optimized capture method allows dense tiling of a target area with little or no interference of similar sequences in the creation of barcoded targets for single molecule kinetics during library preparation. Single molecule analysis allows superior quantitation and chromosome counting. Alternative, the number of reads may be counted. However, single molecule analysis is unbiased, and so is less likely to affect the quantitation. By counting the molecular tags, the methods described herein obtain a more accurate picture of the relative abundance of each sequence in the original DNA sample. The present disclosure also provides a method that has economic benefits over previous methods. In particular, the methods provide savings from the use of a small number of capture reagents (primers) that still are capable of surveying genome-wide indices. The methods also provide a rapid analysis with a low read count in an assay that is easily multiplexed. For example, multiple layers of unique molecular tags and/or bar codes can be used within the methods to identify specific primer species as well as to deconvolute multiplex data to trace signals back to individual samples. Moreover, the methods can be used in ultra low coverage applications such as detecting trisomies in a 100% fetal sample, such as a product of conception, or a non-fetal diagnostic sample. A sample can be mixed (e.g., fetal vs. maternal or diseased vs. non-diseased) or not mixed (e.g., a child suspected of having an aneuploidy), in which case the "coverage" or read depth can be quite low (e.g., a read depth of less than 20,000) because the signal will be strong. The methods also are fast as compared to whole genome sequencing, whole exome sequencing, and massively parallel shotgun sequencing.

The methods of the disclosure are related to the field of genetic analysis. In general, these methods can be used as a rapid and economical means to detect and quantitate deletions and duplications of genetic features in a range extending from complete chromosomes and arms of chromosomes to microscopic deletions and duplications, submicroscopic deletions and deletions, and even single nucleotide features including single nucleotide polymorphisms, deletions, and insertions. In certain embodiments, the methods of the disclosure can be used to detect sub-chromosomal genetic lesions, e.g., microdeletions. Exemplary applications of the methods include pediatric diagnosis of aneuploidy, testing for product of conception or risk of premature abortion, noninvasive prenatal testing (both qualitative and quantitative genetic testing, such as detecting Mendelian disorders, insertions/deletions, and chromosomal imbalances), testing preimplantation genetics, tumor characterization, postnatal testing including cytogenetics, and mutagen effect monitoring.

The nucleic acid molecules (e.g., MIPs) provided by the disclosure also have the benefit of increased binding stability as compared to conventional PCR primer pairs that are not part of the same molecule. In certain embodiments, the exact targeting arm sequences are somewhat short for PCR primers, and hence will have very low melting temperatures in a PCR context. However, in a MIPs configuration, the primers will enhance binding specificity by cooperating to stabilize the interaction. If one arm has a high binding efficiency, the capture is enhanced even if the opposite arm has a lower efficiency. The additive length of the pair improves the "on/off" equilibrium for capture because the lower efficiency arm is more often in proximity of its target in a MIP than it would be as a free PCR primer.

The methods provided by the disclosure have several advantages as compared to targeted sequencing. In certain embodiments, the methods described herein use a simultaneous recognition of two sequence elements at the point of capture, and the two arms are limited by proximity. By contrast, a typical targeted sequencing method will allow a polymerase to initiate at a single site. The run on-product created by typical sequencing produces inefficiency, but may also produce internal or "off-target priming" with the second primer. The inherent "dual recognition" of the nucleic acids of the disclosure (e.g., RO-MIPs) increases stringency, an effect which carries over into the quantitation by the molecular identifier element in the MIP structure. A unique molecular tag may be placed at one site in the MIP backbone, but in standard targeted sequencing using a molecular identifier, a random sequence is used in both primers. Also, the methods provided by the disclosure allow for lower reagent costs since genome-wide coverage can be achieved with very few RO-MIPs compared to the hundreds or thousands of multiplexed, PCR primers required for targeted sequencing. Nevertheless, the methods of the disclosure enjoy most, if not all, of the economic and performance advantages that targeted sequencing displays over shotgun methods.

The methods and nucleic acids of the present disclosure offer clear advantages over previously described genetic methods. For example, whole genome sequencing and massively parallel shotgun sequencing generally require costly analysis of large, non-informative portions of the genome; whereas the present methods can produce similar answers using a fraction of the genome, thereby reducing assay costs and time. Other approaches rely on selectively assaying informative portions of the genome. While certain aspects of the present disclosure share some similarity, the present methods use a novel, comprehensive approach for identifying repeat, primer-binding sites that allow for greater assay design parameters (sequence agnostic—for example, not limited to repeat line elements), more candidate primers (e.g., because all potential primers are enumerated), simple, lower cost assays that are specific and sensitive enough for clinical utility, and a greater ability to multiplex.

The methods and nucleic acids described herein have clear advantages over alternative methods for identifying target sites of interest across the genome that comprise repeat regions, for example, methods that use primers for capturing target sites of interest (or target sequences of interest) to detect chromosomal aneuploidies. In certain embodiments, the methods of the disclosure use MIPs for capturing target sites of interest (or target sequences of interest). In certain embodiments, the MIP replicons (or amplicons) generated in the methods described herein have a size of between 50 and 120 bps (e.g., 50, 55, 60, 65, 70, 75, 80, 85, 90, 95, 100, 105, 110, or 115 bps, or any size between 50 and 120 bps, or any range of size between 50 and 120 bps). In some embodiments, the MIP replicons (or amplicons) have a size of between 80 and 90 bps, or between 80 and 100 bps, or between 80 and 110 bps, or between 80 and 120 bps, or between 70 and 90 bps, or between 70 and 100 bps, or between 70 and 110 bps, or between 70 and 120 bps. In some embodiments, the MIP replicons (or amplicons) have a size of between 80 and 90 bps. Primer capturing methods generate replicons (or amplicons) that are longer than the MIP replicons (or amplicons) generated in the methods described herein. Circulating DNA from plasma samples are often fragmented. When using such DNA as templates, shorter replicons (or amplicons) offer clear advantages over longer ones because shorter replicons (or amplicons) increase the likelihood of capturing short fragments. If an amplicon is long, it is less likely for short fragments to have both binding sites of such long amplicon. Moreover, the read depth per sample in known primer capturing methods is higher than that of the methods described herein. This is one disadvantage of the known primer capturing methods. In certain embodiments, the methods described herein provide a read depth of less than 20 million reads per sample, or less than 19 million reads per sample, or less than 18, 17, 16, 15, 14, 13, 12, 11, 10, 9, 8, 7, 6, 5, 4, or 3 million reads per sample, but no less than 2 million reads per sample, or any range between 2 and 20 million reads per sample, or any range between 3 and 20 million reads per sample. In some embodiments, the methods described herein provide a read depth of between 6 and 8 million reads per sample, e.g., 6, 7, or 8 million reads per sample. Furthermore, when compared to primer capturing methods, the methods described herein target more sites of interests (or sequences of interest) genome-wide and/or on the chromosome of interest (e.g., chromosome 21) than primer capturing methods. In certain embodiments, the methods described herein have a total number of binding sites across the genome in a range of 50 k to 250 k (or any number or range between 50 k and 250 k). In some embodiments, the total number of binding sites across the genome is greater than 50 k, 60 k, 70 k, 80 k, 90 k, 100 k, 110 k, 120 k, 130 k, 140 k, 150 k, 160 k, 170 k, 180 k, 190 k, 200 k, 210 k, 220 k, 230 k, or 240 k. In some embodiments the total number of binding sites across the genome is between 125 k-175 k. In certain embodiments, the methods described herein have a total number of binding sites on a chromosome of interest (e.g., chromosome 21) in a range of 500 to 3000 sites (or any number or range between 500 and 3000 sites). In some embodiments, the total number of binding sites on a chromosome of interest is greater than 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, or 3000 sites. In some embodiments, the unique alignment rates are greater than 35%, 36%, 37%, 38%, 39%, 40%, 41%, 42%, 43%, 44%, 45%, 46%, 47%, 48%, 49%, or 50% or more. As used herein, the term "unique alignment rate" refers to the percentage of total sequencing reads that are uniquely aligned to one chromosomal location on a subject genome (e.g., a human genome).

In certain embodiments, the methods described herein use primer pairs that are not MIPs to capture, or bind to, target sites of interest (or target sequences of interest). In some embodiments, the non-MIP primer pairs are arranged linearly or circularly. As used herein, the terms "target sequence of interest" and "target site of interest" are used interchangeably to refer to a portion of a genomic nucleic acid molecule that primer pairs are designed to capture, or bind to. In some embodiments, one or more primer pairs are designed to hybridize immediately upstream and downstream of a specific target sequence (or site) of interest in a genomic nucleic acid sample. In some embodiments, one or more primer pairs comprise sequences that are complementary to one or more sequences of interest (or sites of interest) in a genomic nucleic acid sample.

In some embodiments, the disclosure provides a method for detecting aneuploidy, or the absence of aneuploidy, in an individual or fetus in need thereof.

In some embodiments, the disclosure provides a method for detecting aneuploidy, or the absence of aneuploidy, in an individual or fetus in need thereof. In some embodiments, the disclosure provides a method of detecting aneuploidy in a fetus comprising:

a) obtaining a nucleic acid sample isolated from a maternal blood sample;

b) capturing a plurality of target sequences of interest in the nucleic acid sample obtained in step a) by using one or more populations of molecular inversion probes (MIPs) to produce a plurality of replicons, wherein each of the MIPs in the population of MIPs comprises in sequence the following components:

first targeting polynucleotide arm and a second targeting polynucleotide arm;

wherein the pair of first and second targeting polynucleotide arms in each of the MIPs are identical, and are substantially complementary to first and second regions in the nucleic acid that, respectively, flank each sequence in the first plurality of target sequences of interest;

c) amplifying target sequences of interest;

d) sequencing target sequences of interest;

e) matching target sequences of interest in silico to genomic sequences at genomic loci; and f) counting number of matching amplicons at individual genomic loci; comparing number of amplicons matched to genomic loci on a test chromosome to number of amplicons matched to genomic loci on a reference chromosomes.

In some embodiments, the disclosure provides a method of detecting aneuploidy in a fetus comprising:

a) obtaining a nucleic acid sample isolated from a maternal blood sample;

b) capturing a plurality of target sequences of interest in the nucleic acid sample obtained in step a) by using one or more populations of molecular inversion probes (MIPs) to produce a plurality of replicons, wherein each of the MIPs in the population of MIPs comprises in sequence the following components:

first targeting polynucleotide arm-first unique molecular tag-polynucleotide linker-second unique molecular tag-second targeting polynucleotide arm;

wherein the pair of first and second targeting polynucleotide arms in each of the MIPs are identical, and are substantially complementary to first and second regions in the nucleic acid that, respectively, flank each sequence in the plurality of target sequences of interest;

wherein the first and second unique targeting molecular tags in each of the MIPs in combination are distinct in each of the MIPs;

c) sequencing a plurality of MIPs amplicons that are amplified from the replicons obtained in step b);

d) determining the number of capture events of each of a first population of amplicons of the plurality of amplicons provided in step c) based on the number of the unique molecular tags of each MIP that amplified a replicon, wherein the first population of amplicons is determined by the sequence of the target sequence of interest;

e) determining the number of capture events of each of a second population of amplicons of the plurality of amplicons provided in step c) based on the number of the unique molecular tags of each MIP that amplified a replicon, wherein the second population of amplicons is determined by the sequence of the target sequence of interest;

f) determining, for each target sequence of interest from which the first population of amplicons was produced, a site capture metric based at least in part on the number of sequencing reads determined in step d);

g) identifying a first subset of the site capture metrics determined in step f) that satisfy at least one criterion;

h) determining, for each target sequence of interest from which the second population of amplicons was produced, a site capture metric based at least in part on the number of capture events determined in step e);

i) identifying a second subset of the site capture metrics determined in step h) that satisfy the at least one criterion;

j) normalizing a first measure determined from the first subset of site capture metrics identified in step g) by a second measure determined from the second subset of site capture metrics identified in step i) to obtain a test ratio;

k) comparing the test ratio to a plurality of reference ratios that are computed based on reference nucleic acid samples isolated from reference subjects known to exhibit euploidy or aneuploidy; and l) determining, based on the comparing in step k), whether aneuploidy is detected in the fetus. Alternatively, this method can be used to detect aneuploidy in a non-fetal subject. In certain embodiments, as an alternative to detecting aneuploidy, the methods of the disclosure can be used to detect and quantitate deletions and duplications of genetic features in arms of chromosomes, as well as microscopic deletions and duplications, submicroscopic deletions and deletions, and single nucleotide features including single nucleotide polymorphisms, deletions, and insertions.

In certain embodiments, the methods of the disclosure can be performed on a nucleic acid sample such as DNA or RNA, e.g., genomic DNA. A nucleic acid sample may be isolated in any manner known to a person of ordinary skill in the art (e.g., by centrifugation). The skilled worker will appreciate that the subject can be any human. When the euploidy, aneuploidy, or disease or condition is being detected in a fetus, the subject is a pregnant female.

In some embodiments, the methods of the disclosure use a single species of MIP. In alternative embodiments, the methods are useful with 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more species of MIPs. For example, multiple species of MIPs can be used to detect different diseases or conditions (e.g., chromosomal abnormalities such as aneuploidy) in a single sample. In certain embodiments, a single MIP can be used to detect different diseases or conditions (e.g., chromosomal abnormalities such as aneuploidy) in a single sample.

The skilled worker will appreciate that the lengths of the first and second targeting polynucleotide arms can be varied as appropriate to provide efficient hybridization between the targeting polynucleotide and the nucleic acid sample. For example the first and/or second targeting polynucleotide arms can be between 14 and 30 base pairs, e.g., 18-21 base pairs. In certain embodiments, the length of the first and/or second targeting polynucleotide arms is 14, 15, 16, 17, 18, 19, 20, 21, 22, 23, 24, 25, 26, 27, 28, 29, or 30 base pairs, or any range between 14 and 30 base pairs. In certain embodiments, the targeting polynucleotide arms have a melting temperature ($T_M$) between 45° C. and 80° C. (e.g., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., or 80° C., or any range between 45° C. and 80° C.) and/or a GC content between 30% and 80% (e.g., approximately 30%, 35%, 40%, 45%, 50%, 55%, 60%, 65%, 70%, 75%, or 80%, or any range between 30% and 80%). In certain embodiments, the targeting polynucleotide arms have a melting temperature ($T_M$) between 45° C. and 80° C. (e.g., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., or 80° C., or any range between 45° C. and 80° C.) and/or a GC content between 30% and 70% (e.g., approximately 30%, 35%, 40%, 45%, 50%, 55%, 60%, 65%, or 70%, or any range between 30% and 70%). In certain embodiments, the targeting polynucleotide arms have a $T_M$ between 60° C. and 70° C. and/or a GC content between 30% and 70%. In certain embodiments, the targeting polynucleotide arms have at least one or more of the following: 1) a length of 14-30 nucleotides; 2) a $T_M$ between 45° C. and 80° C.; and 3) a GC content between 30% and 70%. In certain embodiments, the targeting polynucleotide arms have the same backbone sequence (i.e., the same polynucleotide linker) for post-capture amplification. In some embodiments, the sequence of the first targeting polynucleotide arm is CACTGCACTCCAGCCTGG. In some embodiments, the sequence of the second targeting polynucleotide arm is GAGGCTGAGGCAGGAGAA. In some embodiments, the targeting polynucleotide arms target, for example, greater than 1,000, greater than 10,000, greater than 20,000, greater than 30,000, greater than 40,000, greater than 50,000, greater than 60,000, greater than 70,000, greater than 80,000, greater than 90,000, greater than 100,000, greater than 200,000, greater than 300,000, greater than 400,000, greater than 500,000, greater than 600,000, greater than 700,000, greater than 800,000, greater than 900,000, and/or greater than 1,000,000 sequences of interest (or sites of interests). In some embodiments, the target sequences of interest (or sites of interest) have a size of 50-150 bp (such as 50, 55, 60, 65, 70, 75, 80, 85, 90, 95, 100, 105, 110, 115, 120, 125, 130, 135, 140, 145, or 150 bp, or any range between 50-150 bp). In some embodiments, a RO-MIP does not bind long interspersed nucleotide elements (LINE) in the genome.

Figure 9:
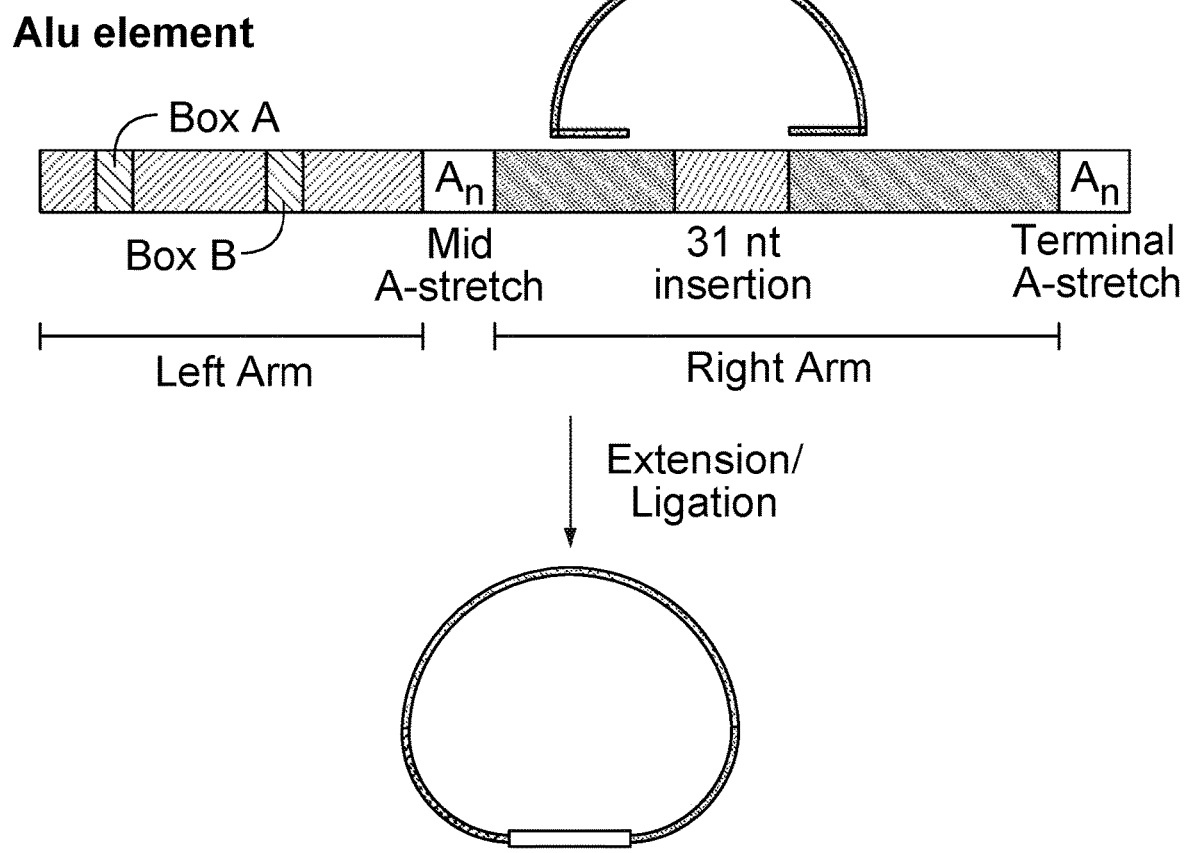
FIG. 9 depicts probe hybridization to an Alu element in an embodiment of the disclosure.

In certain embodiments, the MIPs described herein capture or bind to a plurality of Alu elements in the genome. Alu elements are the most abundant transposable elements in a human subject, having more than one million copies dispersed throughout the genome. Alu elements are repetitive sequences and have a length of about 300 base pairs. See FIG. 9. In some embodiments, the MIPs capture or bind to the right arm of Alu elements. In some embodiments, the MIPs capture or bind to the left arm of Alu elements. In some embodiments, the MIPs capture or bind to the 31-nt insertion region on the right arm of Alu elements (see FIG. 9).

Unique molecular tags provide a way to determine the number of capture events for a given amplicon. A MIP may comprise one or more unique molecular tag, e.g., 1, 2, 3, 4, or 5 unique molecular tags. In certain embodiments, the length of the first and/or second unique molecular tag is between 4 and 15 base pairs, e.g., 4, 5, 6, 7, 8, 9, 10, 11, 12, 13, 14, or 15 base pairs. In certain embodiments, each of the unique molecular tags has a melting temperature between 45° C. and 80° C. (e.g., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., or 65° C.) and/or a GC content between 30% and 80% (e.g., approximately 30%, 35%, 40%, 45%, 50%, 55%, 60%, 65%, 70%, 75%, or 80%, or any range between 30% and 80%, such as 30% to 70%).

A polynucleotide linker bridges the gap between the two targeting polynucleotide arms. In some embodiments, the polynucleotide linker is located directly between the first and second unique molecular tags. In certain embodiments, the polynucleotide linker is not substantially complementary to any genomic region of the subject. In certain embodiments, the polynucleotide linker has a length of between 20 and 1,000 base pairs (e.g., 20, 21, 22, 23, 24, 25, 26, 27, 28, 29, 30, 31, 32, 33, 34, 35, 36, 37, 38, 39, or 40 base pairs) and/or a melting temperature of between 45° C. and 80° C. (e.g., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., or 65° C.) and/or a GC content between 30% and 80% (e.g., approximately 30%, 35%, 40%, 45%, 50%, 55%, 60%, 65%, 70%, 75%, or 80%, or any range between 30% and 80%, such as 30-70%). In certain embodiments, the polynucleotide linker comprises at least one amplification primer, e.g., a forward amplification primer and a reverse amplification primer. For example, the sequence of the forward amplification primer can comprise the nucleotide sequence of 5'-CTTCAGCTTCCCGATTACGG-3' (SEQ ID NO: 1) and/or the sequence of the reverse amplification primer can comprise the nucleotide sequence of 5'-GCACGATCCGACGGTAGTGT-3' (SEQ ID NO: 2). Thus, the nucleotide sequence of the polynucleotide linker can comprise the nucleotide sequence of (SEQ ID NO: 3)
5'-CTTCAGCTTCCCGATTACGGGCACGATCCGACGGTAGTGT-3'.

In certain embodiments, the MIP comprises the nucleotide sequence of 5'-CACTGCACTCCAGCCTGG($N_{1-6}$)CTTCAGCTTCCCGATTACGGGCAC-GATCCGACGGTAGTGT($N_{7-12}$)GAGGCTGAGGCAG-GAGAA-3' (SEQ ID NO: 6), wherein ($N_{1-6}$) represents the first unique molecular tag and ($N_{7-12}$) represents the second unique molecular tag.

In certain embodiments, the disclosure herein provides nucleic acid molecules comprising a nucleotide sequence of 5'-A-(N)x-B-(N)y-C-3', wherein (N)x represents a first unique molecular tag and (N)y represents a second unique molecular tag, and wherein X and Y are between 4 and 15 base pairs, wherein A i) comprises the sequence of 5'-TGCACTCCAGCCTG-3' (SEQ ID NO: 15), or a sequence that is at least 85% similar to the sequence of 5'-TGCACTCCAGCCTG-3' (SEQ ID NO: 15); and ii) has a length of no more than 30 base pairs, wherein C i) comprises the sequence of 5'-GAGGCTGAGGCAGGA-3' (SEQ ID NO: 16), or a sequence that is at least 85% similar to the sequence of 5'-GAGGCTGAGGCAGGA-3'(SEQ ID NO: 16); and ii) has a length of no more than 30 base pairs. In some embodiments, A i) comprises a sequence that is at least 90%, or 95%, similar to the sequence of 5'-TGCACTCCAGCCTG-3' (SEQ ID NO: 15); and ii) has a length of no more than 30 base pairs. In some embodiments, C i) comprises a sequence that is at least 90%, or 95%, similar to the sequence of 5'-GAGGCTGAGGCAGGA-3'(SEQ ID NO: 16); and ii) has a length of no more than 30 base pairs. In some embodiments, B i) comprises the sequence of 5'-CTTCAGCTTCCCGATTACGGGCACGATCCGACGGTAGTGT-3'(SEQ ID NO: 3); or a sequence that is at least 85% (or 90% or 95%) similar to the sequence of 5'-CTTCAGCTTCCCGATTACGGGCACGATCCGACGGTAGTGT-3'(SEQ ID NO: 3). In some embodiments, A or C has a melting temperature between 45° C. and 80° C. In some embodiments, A or C has a GC content between 30% and 80%, or between 30% and 70%.

5'-TCCTGCCTCAGCCTC-3' (SEQ ID NO: 17); and ii) has a length of no more than 30 base pairs, and wherein C i) comprises the sequence of 5'-AGGCTGGAGTGC-3' (SEQ ID NO: 18), or a sequence that is at least 85% similar to the sequence of 5'-AGGCTGGAGTGC-3'(SEQ ID NO: 18); and ii) has a length of no more than 30 base pairs. In some embodiments, A i) comprises a sequence that is at least 90% or 95% similar to the sequence of 5'-TCCTGCCTCAGCCTC-3' (SEQ ID NO: 17), and ii) has a length of no more than 30 base pairs. In some embodiments, C i) comprises a sequence that is at least 9000 or 9500 similar to the sequence of 5'-AGGCTGGAGTGC-3' (SEQ ID NO: 18), and ii) has a length of no more than 30 base pairs. In some embodiments, B comprises the sequence of 5'-CTTCAGCTTCCCGATTACGGGCACGATCCGACGGTAGTGT-3'(SEQ ID NO: 3), or a sequence that is at least 85% (or 90% or 95%) similar to the sequence of 5'-CTTCAGCTTCCCGATTACGGGCACGATCCGACGGTAGTGT-3'(SEQ ID NO: 3). In some embodiments, or has melting temperature between 45° C. and 80° C. In some embodiments, A or C has a GC content between 30% and 80%, or between 30% and 70%.

In some embodiments, the MIPs used in the methods described in are as follows, where the corresponding values for A, B, C, D, E, F, G, and Hare as described in relation to Tables 1 and 2, and the corresponding values for the score are as described in relation to EQ. 9:

| | | | | | SEQUENCE | | | | | |
|---|---|---|---|---|---|---|---|---|---|---|
| ID | A | B | C | D | E | F | G | H | | SCORE |
| MIP 001 | /5Phos/CCACTGCACTCCAGCCTGNNNNNNNCTTCAGCTTCCCGATTACGGGCAC GATCCGACGGTAGTGTNNNNNNNGAGGCTGAGGCAGGAGAA (SEQ ID NO: 7) | | | | | | | | | |
| | 757 | 439 | 1329 | 576 | 63973 | 38697 | 120953 | 50631 | | 8.151 |
| MIP 002 | /5Phos/TCTCCTGCCTCAGCCTCCNNNNNNNCTTCAGCTTCCCGATTACGGGCAC GATCCGACGGTAGTGTNNNNNNNAGGCTGGAGTGCAGTGGC (SEQ ID NO: 8) | | | | | | | | | |
| | 539 | 341 | 1092 | 559 | 44384 | 30852 | 100409 | 48075 | | 5.868 |
| MIP 003 | /5Phos/CACTGCACTCCAGCCTGGNNNNNNNCTTCAGCTTCCCGATTACGGGCAC GATCCGACGGTAGTGTNNNNNNNGAGGCTGAGGCAGGAGAA (SEQ ID NO: 9) | | | | | | | | | |
| | 784 | 424 | 1326 | 556 | 65221 | 37461 | 122258 | 48707 | | 8.557 |
| MIP 004 | /5Phos/CCACTGCACTCCAGCCTGNNNNNNNCTTCAGCTTCCCGATTACGGGCAC GATCCGACGGTAGTGTNNNNNNNGGAGGCTGAGGCAGGAGA (SEQ ID NO: 10) | | | | | | | | | |
| | 755 | 420 | 1277 | 546 | 62323 | 36938 | 119507 | 48684 | | 8.167 |
| MIP 005 | /5Phos/CACTGCACTCCAGCCTGGNNNNNNNCTTCAGCTTCCCGATTACGGGCAC GATCCGACGGTAGTGTNNNNNNNCAGGAGGCTGAGGCAGGA (SEQ ID NO: 11) | | | | | | | | | |
| | 272 | 71 | 781 | 282 | 20949 | 6673 | 69142 | 23425 | | 4.301 |
| MIP 006 | /5Phos/ACTGCACTCCAGCCTGGNNNNNNNCTTCAGCTTCCCGATTACGGGCACG ATCCGACGGTAGTGTNNNNNNNGGAGGCTGAGGCAGGAG (SEQ ID NO: 12) | | | | | | | | | |
| | 865 | 407 | 1393 | 513 | 70197 | 36142 | 131805 | 46075 | | 9.761 |
| MIP 007 | /5Phos/TGCACTCCAGCCTGGGCANNNNNNNCTTCAGCTTCCCGATTACGGGCAC GATCCGACGGTAGTGTNNNNNNNGAGGCTGAGGCAGGAGAA (SEQ ID NO: 13) | | | | | | | | | |
| | 370 | 80 | 902 | 315 | 32498 | 8732 | 76997 | 26567 | | 5.283 |
| MIP 008 | /5Phos/CTGCACTCCAGCCTGGGCNNNNNNNCTTCAGCTTCCCGATTACGGGCAC GATCCGACGGTAGTGTNNNNNNNGAGGCTGAGGCAGGAGAA (SEQ ID NO: 14) | | | | | | | | | |
| | 475 | 261 | 1078 | 386 | 37864 | 22133 | 96980 | 34718 | | 5.965 |

In certain embodiments, the disclosure herein provides nucleic acid molecules comprising a nucleotide sequence of 5'-A-(N)x-B-(N)y-C-3', wherein (N)x represents a first unique molecular tag and (N)y represents a second unique molecular tag, and wherein X and Y are between 4 and 15 base pairs, wherein A i) comprises the sequence of 5'-TCCTGCCTCAGCCTC-3' (SEQ ID NO: 17), or a sequence that is at least 85% similar to the sequence of In some embodiments, the population of MIPs used in a method of the disclosure has a concentration between 10 fM and 100 nM, for example, 0.5 nM. In certain embodiments, the concentration of MIPs used in a method of the disclosure will vary with the number of sequences being targeted, e.g., as calculated by multiplying the number of target sequences of interest by the number of genomic equivalents in a reaction (the "total target number"). In particular embodiments, the approximate ratio of the number of MIP molecules to the total target number is 1:50, 1:100, 1:150, 1:200, 1:250, 1:300, 1:350, 1:400, 1:450, 1:500, 1:550, 1:600, 1:650, 1:700, 1:750, 1:800, 1:850, 1:900, 1:950, or 1:1,000. In certain embodiments, each of the MIPs replicons and/or amplicons is a single-stranded circular nucleic acid molecule.

In some embodiments, the MIPs replicons are produced by: i) the first and second targeting polynucleotide arms, respectively, hybridizing to the first and second regions in the nucleic acid sample, respectively, wherein the first and second regions flank a target sequence of interest; and ii) after the hybridization, using a ligation/extension mixture to extend and ligate the gap region between the two targeting polynucleotide arms to form single-stranded circular nucleic acid molecules. In certain embodiments, a MIP amplicon is produced by amplifying a MIP replicon, e.g., through PCR.

In some embodiments, the sequencing step comprises a next generation sequencing method, for example, a massive parallel sequencing method, or a short read sequencing method. In some embodiments, sequencing may be by any method known in the art, for example, targeted sequencing, single molecule real-time sequencing, electron microscopy-based sequencing, transistor-mediated sequencing, direct sequencing, random shotgun sequencing, Sanger dideoxy termination sequencing, targeted sequencing, exon sequencing, whole-genome sequencing, sequencing by hybridization, pyrosequencing, capillary electrophoresis, gel electrophoresis, duplex sequencing, cycle sequencing, single-base extension sequencing, solid-phase sequencing, high-throughput sequencing, massively parallel signature sequencing, emulsion PCR, co-amplification at lower denaturation temperature-PCR (COLD-PCR), multiplex PCR, sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, 454 sequencing, Solexa Genome Analyzer sequencing, SOLiD® sequencing, MS-PET sequencing, mass spectrometry, and a combination thereof. In some embodiments, sequencing comprises an detecting the sequencing product using an instrument, for example but not limited to an ABI PRISM® 377 DNA Sequencer, an ABI PRISM® 310, 3100, 3100-Avant, 3730, or 3730xl Genetic Analyzer, an ABI PRISM® 3700 DNA Analyzer, or an Applied Biosystems SOLiD™ System (all from Applied Biosystems), a Genome Sequencer 20 System (Roche Applied Science), or a mass spectrometer. In certain embodiments, sequencing comprises emulsion PCR. In certain embodiments, sequencing comprises a high throughput sequencing technique, for example but not limited to, massively parallel signature sequencing (MPSS).

A sequencing technique that can be used in the methods of the disclosure includes, for example, Illumina sequencing. Illumina sequencing is based on the amplification of DNA on a solid surface using fold-back PCR and anchored primers. Genomic DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated. Sequencing according to this technology is described in U.S. Pat. Nos. 7,960,120; 7,835,871; 7,232,656; 7,598,035; 6,911,345; 6,833,246; 6,828,100; 6,306,597; 6,210,891; U.S. Pub. 2011/0009278; U.S. Pub. 2007/0114362; U.S. Pub. 2006/0292611; and U.S. Pub. 2006/0024681, each of which are incorporated by reference in their entirety.

In some embodiments, a method of the disclosure comprises, before sequencing (e.g., the sequencing step of d) as described above), a PCR reaction to amplify the MIPs amplicons for sequencing. This PCR reaction may be an indexing PCR reaction. In certain embodiments, the indexing PCR reaction introduces into each of the MIPs amplicons the following components: a pair of indexing primers, a unique sample barcode and a pair of sequencing adaptors. In particular embodiments, the barcoded targeting MIPs amplicons comprise in sequence the following components:

a first sequencing adaptor-a first sequencing primer-the first unique targeting molecular tag-the first targeting polynucleotide arm-captured nucleic acid-the second targeting polynucleotide arm-the second unique targeting molecular tag-a unique sample barcode-a second sequencing primer-a second sequencing adaptor.

In some embodiments, the first plurality of target sequences of interest is on a single chromosome. In some embodiments, the second plurality of target sequences of interest are on multiple chromosomes. Because the a single MIP sequence can be used to target sequences of interest across an entire genome, in certain embodiments the methods of the disclosure provide the benefit of being able to detect aneuploidy of more than one chromosome at a time. For example, the first plurality of target sequences can be defined as sequences on chromosome 21, and the second plurality of target sequences can be defined as sequences on the remaining chromosomes. Using the same reaction, however, the first plurality of target sequences can be defined as sequences on chromosome 13, and the second plurality of target sequences can be defined as sequences on the remaining chromosomes. Thus, the sequencing data from the same reaction can be used to detect both Down syndrome (trisomy 21) and Patau syndrome (trisomy 13). Likewise, MIPs can be designed, and data can be analyzed, to detect 1, 2, 3, 4, 5, 6, 7, 8, 9, 10, or more conditions associated with aneuploidy, or other types of chromosomal or subchromosomal abnormalities.

In some embodiments, the disclosure provides a method of detecting aneuploidy in a fetus comprising:

a) obtaining a genomic DNA sample from a maternal blood sample;

b) adding the genomic DNA sample into each well of a multi-well plate, wherein each well of the multi-well plate comprises a probe mixture, wherein the probe mixture comprises a population of molecular inversion probes (MIPs) and a buffer;

wherein each MIP in the population of MIPs comprises in sequence the following components:

first targeting polynucleotide arm-first unique molecular tag-polynucleotide linker-second unique molecular tag-second targeting polynucleotide arm;

wherein the pair of first and second targeting polynucleotide arms in each of the MIPs are identical, and are substantially complementary to first and second regions in the nucleic acid that, respectively, flank each sequence in a plurality of target sequences of interest;

wherein the first and second unique targeting molecular tags in each of the MIPs in combination are distinct in each of the MIPs;

c) incubating the genomic DNA sample with the probe mixture for the MIPs to capture the plurality of target sequences of interest;

d) adding an extension/ligation mixture to the sample of c) for the MIPs and the plurality of target sequences of interest to form a plurality of MIPs amplicons, wherein the extension/ligation mixture comprises a polymerase, a plurality of dNTPs, a ligase, and buffer;

e) adding an exonuclease mixture to the targeting and control MIPs amplicons to remove excess probes or excess genomic DNA;

f) adding an indexing PCR mixture to the sample of e) to add a pair of indexing primers, a unique sample barcode and a pair of sequencing adaptors to the plurality of amplicons;

g) using a massively parallel sequencing method to determine the number of sequencing reads of a first population of barcoded amplicons provided in step f) based on the number of the unique targeting molecular tags, wherein the first population of barcoded amplicons is identified by the sequence of the target sequence of interest;

h) using a massively parallel sequencing method to determine the number of sequencing reads of a second population of barcoded amplicons provided in step f) based on the number of the unique targeting molecular tags, wherein the second population of barcoded amplicons is identified by the sequence of the target sequence of interest;

i) computing a site capture metric based at least in part on the number of first sequencing reads determined in step g) and a plurality of control probe capture metrics based at least in part on the numbers of second sequencing reads determined in step h);

j) identifying a subset of site capture metrics of the population of the MIPs amplicons that have control probe capture metrics satisfying at least one criterion;

k) normalizing the site capture metric by a factor computed from the subset of control probe capture metrics satisfying the at least one criterion, to obtain a test normalized site capture metric;

l) comparing the test normalized site capture metric to a plurality of reference normalized site capture metrics that are computed based on reference genomic DNA samples obtained from reference subjects exhibiting known genotypes using the same target and control sites, target population, subset of control populations in steps b)-h); and m) determining, based on the comparing in step l) and the known genotypes of reference subjects, whether aneuploidy is detected in the fetus.

In some embodiments, the disclosure provides a method of selecting a molecular inversion probe (MIP) from a plurality of candidate MIPs for using to detect aneuploidy in a subject, the method comprising:

a) receiving nucleic acid sequences of the plurality of candidate MIPs;

b) for each respective MIP in the plurality of candidate MIPs, i) computing a first number (A) of unique sites predicted, with no mismatch, to be captured by the respective MIP on a chromosome of interest;

ii) computing a second number (C) of unique sites predicted, with one mismatch, to be captured by the respective MIP on the chromosome of interest;

iii) computing a third number (E) of unique sites predicted, with no mismatch, to be captured by the respective MIP across a genome;

iv) computing a fourth number (G) of unique sites predicted, with one mismatch, to be captured by the respective MIP across the genome;

v) computing a fifth number (F) of non-unique sites predicted, with no mismatch, to be captured by the respective MIP across the genome;

vi) computing a sixth number (H) of non-unique sites predicted, with one mismatch, to be captured by the respective MIP across the genome;

vii) computing a performance metric for the respective MIP based at least in part on the first, second, third, fourth, fifth, and sixth numbers;

c) selecting a MIP, based at least in part on the performance metric computed in step b) vii) for each MIP in the plurality of candidate MIPs.

In certain embodiments, the MIP at step c) is selected such that a first ratio between the first number (A) and the fifth number (F) is larger than an equivalent ratio for a remaining set of the candidate MIPs. In certain embodiments, the MIP at step c) is selected such that a second ratio between the first number (A) and the third number (E) is larger than an equivalent ratio for a remaining set of the candidate MIPs. In certain embodiments, the MIP at step c) is selected such that a third ratio between the first number (A) and the second number (C) is larger than an equivalent ratio for a remaining set of the candidate MIPs. In certain embodiments, the MIP at step c) is selected such that a fourth ratio between a first sum of the first number (A) and the second number (C) and a second sum of the third, fourth, fifth, and six numbers (E, F, G, H) is larger than an equivalent ratio for a remaining set of the candidate MIPs. In certain embodiments, the MIP at step c) is selected such that a fifth ratio between a first weighted sum of the first number (A) and the second number (C) and a second weighted sum of the third, fourth, fifth, and six numbers (E, F, G, H) is larger than an equivalent ratio for a remaining set of the candidate MIPs. In certain embodiments, the fifth ratio (P1) between the first weighted sum and the second weighted sum is:

$$P1 = \frac{A + K_e C}{(E + F) + K_e (G + H)}.$$

In certain embodiments, the MIP at step c) is selected such that a third weighted sum between the first number (A) and the second number (C) is larger than an equivalently weighted sum for a remaining set of the candidate MIPs. In certain embodiments, the third weighted sum is:

$P2 = A + K_e C$. In certain embodiments, the MIP at step c) is selected such that a product between the fifth ratio (P1) and the third weighted sum (P2) is larger than an equivalent product for a remaining set of the candidate MIPs. In certain embodiments, the performance metric is calculated based on a total number of useful reads from the chromosome of interest. In certain embodiments, the MIP at step c) is selected based on a ratio ($K_e$) of an average capture coefficient of one mismatch sites ($K_1$) and an average capture coefficient of zero mismatch sites ($K_0$):

$$K_e = \frac{K_1}{K_0}.$$

In certain embodiments, the ratio ($K_e$) is experimentally estimated. In certain embodiments, the MIP at step c) is selected based on a total molecular tag count (TMTC) defined as:

$$TMTC = K_0(E+F) + K_1(G+H).$$

In some embodiments, the disclosure also provides a nucleic acid molecule comprising a nucleotide sequence of 5'-CACTGCACTCCAGCCTGG($N_{1-6}$)CTTCAGCTTCCC-GATTACGGGCACGATCCGACGGTAGTGT($N_{7-12}$) GAGGCTGAGGCAGGAGAA-3' (SEQ ID NO: 6), wherein ($N_{1-6}$) represents a first unique molecular tag and ($N_{7-12}$) represents a second unique molecular tag. In certain embodiments, the length of the first unique molecular tag is between 4 and 15 base pairs. In certain embodiments, the length of the second unique molecular tag is between 4 and 15 base pairs. In certain embodiments, each of the unique targeting molecular tags has a melting temperature between 45° C. and 80° C. In certain embodiments, each of the unique targeting molecular tags have a GC content between 30% and 80% or between 30% and 70%. The disclosure further provides a composition comprising any of the nucleic acid molecules described herein.

Methods for Identifying MIPs

FIG. 1 is a block diagram of a computing device 100 for performing any of the processes described herein, including processes 200, 300, and 500. As used herein, the term "processor" or "computing device" refers to one or more computers, microprocessors, logic devices, servers, or other devices configured with hardware, firmware, and software to carry out one or more of the computerized techniques described herein. Processors and processing devices may also include one or more memory devices for storing inputs, outputs, and data which is currently being processed. The computing device 100 may include a "user interface," which may include, without limitation, any suitable combination of one or more input devices (e.g., keypads, touch screens, trackballs, voice recognition systems, etc.) and/or one or more output devices (e.g., visual displays, speakers, tactile displays, printing devices, etc.). The computing device 100 may include, without limitation, any suitable combination of one or more devices configured with hardware, firmware, and software to carry out one or more of the computerized techniques described herein. Each of the components described herein may be implemented on one or more computing devices 100. In certain aspects, a plurality of the components of these systems may be included within one computing device 100. In certain embodiments, a component and a storage device may be implemented across several computing devices 100.

The computing device 100 comprises at least one communications interface unit 108, an input/output controller 110, system memory, and one or more data storage devices. The system memory includes at least one random access memory (RAM 102) and at least one read-only memory (ROM 104). All of these elements are in communication with a central processing unit (CPU 106) to facilitate the operation of the computing device 100. The computing device 100 may be configured in many different ways. For example, the computing device 100 may be a conventional standalone computer or alternatively, the functions of computing device 100 may be distributed across multiple computer systems and architectures. In FIG. 1, the computing device 100 is linked, via network or local network, to other servers or systems.

The computing device 100 may be configured in a distributed architecture, wherein databases and processors are housed in separate units or locations. Some units perform primary processing functions and contain at a minimum a general controller or a processor and a system memory. In distributed architecture embodiments, each of these units may be attached via the communications interface unit 108 to a communications hub or port (not shown) that serves as a primary communication link with other servers, client or user computers and other related devices. The communications hub or port may have minimal processing capability itself, serving primarily as a communications router. A variety of communications protocols may be part of the system, including, but not limited to: Ethernet, SAP, SAS™, ATP, BLUETOOTH™, GSM and TCP/IP.

The CPU 106 comprises a processor, such as one or more conventional microprocessors and one or more supplementary co-processors such as math co-processors for offloading workload from the CPU 106. The CPU 106 is in communication with the communications interface unit 108 and the input/output controller 110, through which the CPU 106 communicates with other devices such as other servers, user terminals, or devices. The communications interface unit 108 and the input/output controller 110 may include multiple communication channels for simultaneous communication with, for example, other processors, servers or client terminals.

The CPU 106 is also in communication with the data storage device. The data storage device may comprise an appropriate combination of magnetic, optical or semiconductor memory, and may include, for example, RAM 102, ROM 104, flash drive, an optical disc such as a compact disc or a hard disk or drive. The CPU 106 and the data storage device each may be, for example, located entirely within a single computer or other computing device; or connected to each other by a communication medium, such as a USB port, serial port cable, a coaxial cable, an Ethernet cable, a telephone line, a radio frequency transceiver or other similar wireless or wired medium or combination of the foregoing. For example, the CPU 106 may be connected to the data storage device via the communications interface unit 108. The CPU 106 may be configured to perform one or more particular processing functions.

The data storage device may store, for example, (i) an operating system 112 for the computing device 100; (ii) one or more applications 114 (e.g., computer program code or a computer program product) adapted to direct the CPU 106 in accordance with the systems and methods described here, and particularly in accordance with the processes described in detail with regard to the CPU 106; or (iii) database(s) 116 adapted to store information that may be utilized to store information required by the program.

The operating system 112 and applications 114 may be stored, for example, in a compressed, an uncompiled and an encrypted format, and may include computer program code. The instructions of the program may be read into a main memory of the processor from a computer-readable medium other than the data storage device, such as from the ROM 104 or from the RAM 102. While execution of sequences of instructions in the program causes the CPU 106 to perform the process steps described herein, hard-wired circuitry may be used in place of, or in combination with, software instructions for embodiment of the processes of the present disclosure. Thus, the systems and methods described are not limited to any specific combination of hardware and software.

Suitable computer program code may be provided for performing one or more functions as described herein. The program also may include program elements such as an operating system 112, a database management system and "device drivers" that allow the processor to interface with computer peripheral devices (e.g., a video display, a keyboard, a computer mouse, etc.) via the input/output controller 110.

The term "computer-readable medium" as used herein refers to any non-transitory medium that provides or participates in providing instructions to the processor of the computing device 100 (or any other processor of a device described herein) for execution. Such a medium may take many forms, including but not limited to, non-volatile media and volatile media. Non-volatile media include, for example, optical, magnetic, or opto-magnetic disks, or integrated circuit memory, such as flash memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM or EEPROM (electronically erasable programmable read-only memory), a FLASH-EEPROM, any other memory chip or cartridge, or any other non-transitory medium from which a computer can read.

Various forms of computer readable media may be involved in carrying one or more sequences of one or more instructions to the CPU 106 (or any other processor of a device described herein) for execution. For example, the instructions may initially be borne on a magnetic disk of a remote computer (not shown). The remote computer can load the instructions into its dynamic memory and send the instructions over an Ethernet connection, cable line, or even telephone line using a modem. A communications device local to a computing device 100 (e.g., a server) can receive the data on the respective communications line and place the data on a system bus for the processor. The system bus carries the data to main memory, from which the processor retrieves and executes the instructions. The instructions received by main memory may optionally be stored in memory either before or after execution by the processor. In addition, instructions may be received via a communication port as electrical, electromagnetic or optical signals, which are exemplary forms of wireless communications or data streams that carry various types of information.

Figure 2:
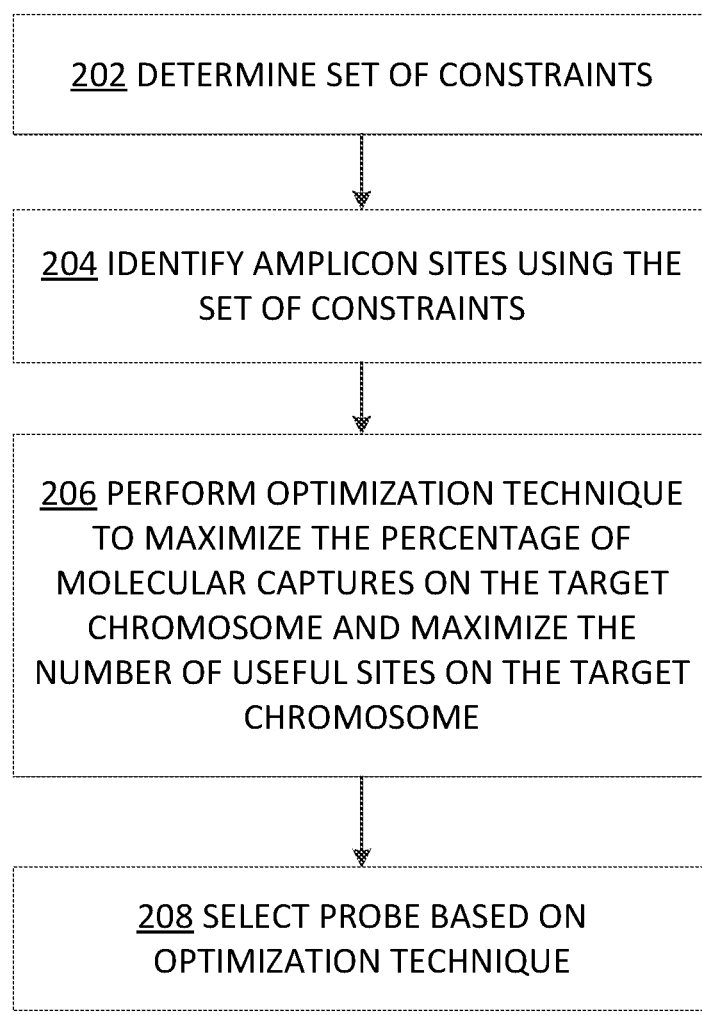
FIG. 2 is a representative process flow diagram for designing and selecting a probe according to some methods of the disclosure.

FIG. 2 is a flowchart of a process 200 for designing and selecting a probe (e.g., a MIP), according to an illustrative embodiment. The process 200 includes the steps of determining a set of constraints (step 202), identifying primers using the set of constraints (step 204), performing an optimization technique to maximize the percentage of molecular captures on the target chromosome and to maximize the number of useful sites on the target chromosome (step 206), and selecting a probe based on the optimization technique (step 208).

At step 202, a set of constraints is determined. The set of constraints may be determined, for example, by CPU 106 using software or application(s) implemented thereon. In some embodiments, the software or application(s) may also be used by CPU 106 to perform any one or more of the subsequent steps in process 200. For example, the software and application(s) may be used by CPU 106 to find abundant primer pairs in a given reference genome (e.g., HG19) based on the determined constraints, and to automatically create suffix-array-based index for the genome file.

In some embodiments, the set of constraints may alternatively be referred to as algorithm flags. For example, the constraints (or algorithm flags) may include a length of the left primer, a minimum frequency of the primer-pair, a maximum distance between primers (e.g., amplicon length), a minimum and/or maximum total frequency of the primer, a minimum GC-content per primer in percent, a minimum amount of non-identical amplicons in percent, a distribution of primers in genome, or any suitable combination thereof. In an illustrative embodiment, the following constraints may be used in designing primer pairs:

Length of the left primer: 18, 19, 20, 21 base pairs (bp)
Frequency of primer-pair: 100, 250, 500, 2500, 5000, 10000
Amplicon Length: 50-150 bp, e.g., less than 85 bp
Minimum GC content per primer: 40%
Amplicon uniqueness (percent of target sequences of interest that are unique): greater than 80%
Distribution of primers in genome: iteratively ran, with each bucket size (bs) ranging from 1 to 50%, and bucket-fill (bf) ranging from 1 to bs-1, wherein bucket size (bs) refers to bs % of genome long, and each bucket must contain bf % of all hits.

At step 204, a set of primers are identified using the set of constraints determined at step 202. In particular, for each primer design, any combination of the following parameters may be provided: the left primer sequences (e.g., as well as the number of their occurrences on the positive and negative strands of the genome), the right primer sequences (e.g., as well as the number of their occurrences on the positive and negative strands of the genome), the frequency of the pair (e.g., the left primer sequence and the right primer sequence paired together with the amplicon length limited by a constraint) including both unique and non-unique pairs, the frequency and percentage of the uniquely occurring amplicons, and the amplicon sequences from unique and non-unique pairs. In some embodiments, each primer pair may be able to amplify multiple regions on the genome (e.g., more than hundreds, more than thousands, more than tens of thousands, more than hundreds of thousands, or more than millions).

In some embodiments, the generated primer pairs may identify or predict amplicon sites without allowing for any mismatches to occur in either the left primer sequence or in the right primer sequence (i.e., the left or right arms). Alternatively, in order for additional amplicon sites to be identified or predicted, a small number of mismatches may be allowed, such as allowing for:

1 mismatch in the left arm and 0 mismatches in the right arm
0 mismatches in the left arm and 1 mismatch in the right arm
1 mismatch in the left arm and 1 mismatch in the right arm
2 mismatches in the left arm and 0 mismatches in the right arm, or
0 mismatches in the left arm and 2 mismatch in the right arm.

In some embodiments, the amplicon prediction scheme described above provides the genomic coordinates of the predicted amplicons. However, in some embodiments, it may be computationally intensive for the scheme that identifies the amplicon sites without allowing for any mismatches to occur to also provide the genomic coordinates of the predicted amplicons. In this case, the scheme may be divided into two parts. In a first part, the amplicon sites are identified without allowing for any mismatches to occur, and the genomic coordinates of the identified amplicon sites are not provided. In a second part, the amplicon sites that include a small number of mismatches (e.g., the set of mismatches enumerated above) are identified, and the genomic coordinates of these amplicon sites are provided, as well as the genomic coordinate of the no-mismatch amplicon sites. Splitting up the scheme into these two modular parts may save computational complexity. However, in general, it will be understood that the two parts may be combined to provide the set of no-mismatch amplicon sites, mismatch amplicon sites, and their genomic coordinates in a single function.

In some embodiments, one or more of the amplicon sites identified at step 204 may be removed (e.g., by a filtering operation). For example, amplicon sites may be removed if the sites have mismatches that do not occur at least 3 base pairs (bp) from 5' end of the left primers and 3' end of the right primers. The amplicon sites of those primers that passed the filtering operation (hereinafter referred to as "candidate primers") should enrich the chromosome of interest while targeting multiple regions of the reference genome (e.g., typically 2500 or more). Additionally, in some embodiments, both the left and right arm sequences of the candidate primers should have melting temperatures ($T_M$) ranging from low 60 to high 60s as computed by the nearest neighbor model of DNA binding stability, wherein empirical stability parameters are summed according to the nucleic acid sequence. See, e.g., Santa Lucia and Hicks 2004. Lastly, the candidate primers should have high tolerance to mismatches occurring at 3 bps on the 5' of the left arm and the 3' of the right arm.

After the removal (or filtering) operation, the remaining amplicon sites will be further processed in order to generate a set of parameter values for each candidate primer. In some embodiments, the proportion of the number of amplicon sites coming from the chromosome of interest and the total number of amplicon sites that have passed the filtering operation will be calculated. For each candidate primer, the enrichment information (e.g., the calculated proportion), the associated amplicon sites information, and any other parameter values may be saved in a database, such as database 116.

At step 206, an optimization technique is performed to identify a primer with an optimal predicted performance. The optimization technique involves evaluating an objective function for each candidate primer. In particular, it may be desirable to use an objective function that maximizes a proportion of the captured sites that are on the chromosome of interest, compared to the number of captured sites that are on other chromosomes. Moreover, the objective function may further maximize a number of sites from the chromosome of interest. In some embodiments, the candidate primers may optionally include primers that have a high frequency of single nucleotide polymorphisms (SNP) in their predicted amplicon sites. Due to the presence of high-ranking primers targeting similar repeat sequences, in some embodiments, only a subset of the candidate primers with the highest proportion of sites coming from the chromosome of interest may be identified from among the primers with high overlaps and the remaining candidate primers may be spared for future use.

The objective function for each candidate MIP may, in some embodiments, be established based on the following matrices:

TABLE 1

Predicted site count on chromosome of interest

| | Site Counts | |
|---|---|---|
| | Unique | Non-unique |
| 0 mismatch | A | B |
| 1 mismatch | C | D |

TABLE 2

Predicted site count across the genome

| | Site Counts | |
|---|---|---|
| | Unique | Non-unique |
| 0 mismatch | E | F |
| 1 mismatch | G | H |

In the probe matrices above, rows labeled as "0 mismatch" indicates MIPs with perfect matches in both arms, and rows labeled as "1 mismatch" indicates primers that tolerates at most 1 mismatch in one of its arms. In Table 1, the column labeled as "unique" corresponds to the number of sites on the chromosome of interest that aligned only once to a respective MIP, where the alignment occurred on the chromosome of interest and on no other chromosome. In Table 1, the column labeled as "non-unique" corresponds to the number of sites on the chromosome of interest that aligned more than once to a respective MIP, where the alignment occurred multiple times on the chromosome of interest, on multiple chromosomes, or both. In Table 2, the column labeled as "unique" corresponds to the number of sites across all chromosomes (including all of chromosomes 1-22, X, and Y, for example) that aligned only once to a respective MIP. In other words, the value E includes a sum across multiple $A_i$, which represents the number of unique sites with zero mismatches on the i-th chromosome. Similarly, the column labeled as "non-unique" in Table 2 corresponds to the number of sites across all chromosomes that aligned more than once to a respective MIP, including instances where the alignment occurred multiple times on the same chromosome, on multiple chromosomes, or both.

Several intuitive objective functions can be readily deduced from these probe matrices. It may be generally desirable to select a MIP that has a high percentage of sites that match the arm sequences (or at most have a small number of mismatches, such as one mismatch). It may further be desirable to select a MIP associated with a high percentage of unique sites. This may be represented by selecting MIPs that have values for A, C, E, or G (or any suitable combination thereof) to be relatively high compared to B, D, F, or H (or any suitable combination thereof). It may further be desirable to select a MIP associated with a high percentage of sites that are on the chromosome of interest. This may be represented by selecting MIPs that have values for A, B, C, or D (or any suitable combination thereof) to be relatively high compared to E, F, G, or H (or any suitable combination thereof).

For example, an objective function that maximizes or increases A/F may produce fewer ambiguous reads for candidate primers that tolerate 0 mismatches. In a second example, an objective function that maximizes or increases A/E may produce target chromosome (e.g., chromosome 21) specific reads. As a third example, an objective function that maximizes or increases A/C selects primers that have significantly more perfect matching sites than those that have 1 mismatch, and as a result, represents an efficient capture. As a fourth example, an objective function that maximizes or increases A means that a large number of sites uniquely aligned to the chromosome of interest. As a fifth example, an optimal primer can be selected to maximize an objective function of (A+C)/(E+F+G+H). To further illustrate this concept, three exemplary objective functions are explained in detail below.

A. Total Number of Useful Reads from the Chromosome of Interest (P1)

An exemplary objective function for each candidate primer or probe may be defined as the total number of useful reads from the chromosome of interest (e.g., Chromosome 21):

$$P1 = f4(A, B, C, \ldots, H; K_0, K_1) \quad (1)$$

where $K_0$ is the average capture coefficient of 0 mismatch sites and $K_1$ is the average capture coefficient of 1 mismatch sites. More specifically:

$$P1 = K_0 A + K_1 C \quad (2)$$

$$TMTC = K_0(E+F) + K_1(G+H) \quad (3)$$

where TMTC is the total molecular tag count.

Given that:

$$K_e = \frac{K_1}{K_0}, \text{ where } 0 < K_e < 1 \quad (4)$$

and that the value of $K_e$ can be estimated from experimental data, Equation (2) can be rewritten as:

$$P1 = \frac{A + K_e C}{(E + F) + K_e(G + H)} \quad (5)$$

using values extracted from the probe matrices in Tables 1 and 2. The numerator of EQ. 5 may be referred to herein as an adjusted number of usable sites (on the chromosome of interest). The denominator of EQ. 5 may be referred to herein as a number of sites on the genome. The value of P1 as defined in EQ. 5 may be referred to herein as an efficiency fraction or a useful fraction.

B. Total Number of Effective Sites on the Chromosome of Interest (P2)

Another exemplary objective function for each candidate primer or probe may be defined as the total number of effective sites on the chromosome of interest (e.g., Chromosome 21):

$$P2 = g(A, B, C, \ldots H; K_0, K_1) \quad (6)$$

where $K_0$ and $K_1$ are defined in Equation (1). More specifically, P2 may be defined as:

$$P2 = A + K_e C \quad (7)$$

where $K_e$ is defined in Equation (4). Similar to $P_1$, the value of $P_2$ can also be calculated using values extracted from the probe matrices in Tables 1 and 2. The value of $P_2$ may be referred to as an adjusted number of usable sites.

C. Comprehensive Probe Performance Function

A comprehensive way to evaluate an objective function for each candidate primer or probe is to have:

$$P = P_1 * P_2 \quad (8)$$

Incorporating Equations (5) and (7), Equation (8) can be rewritten as:

$$P = \frac{(A + K_e C)^2}{(E + F) + K_e(G + H)} \quad (9)$$

Note that, as described above in relation to Equation (4), the value of $K_e$ can be estimated using experimental data. More particularly:

$$K_e = \frac{K_1}{K_0} = \frac{\frac{\text{molecular tag counts}}{\text{on 1 mismatch sites}}}{\frac{\text{1 mismatch site count}}{\text{on 0 mismatch sites}}} \quad (10)$$

The value for P defined in EQ. 9 may be used as a composite score to represent an overall predicted performance of a candidate primer or probe, and may be referred to as a product between an adjusted number of usable sites and an efficiency fraction (or useful fraction). In an example, the value for P defined in EQ. 9 may be compared to a predetermined threshold to assess whether to select an associated candidate primer or probe for further testing or for diagnosis. For example, the predetermined threshold may be a value such as 1, 2, 3, 4, 5, 6, 7, 8, 9, 10, or any other suitable number.

Any of the above-described examples, and any combination of the examples, may be used as an objective function without departing from the scope of the present disclosure. Selecting a primer by optimizing an objective function in this manner has an advantage of reducing a necessary read depth to achieve a sufficient number of useful reads. In principle, the improvement in read depth scales linearly with an improvement in reduction of ambiguity.

At step 208, a primer is selected from the set of candidate primers based on the optimization technique performed at step 206. For example, the selected primer may correspond to the primer with the optimal predicted performance, i.e., the primer that maximized the objective function as described in relation to step 206.

In an illustrative embodiment, a number of primers (e.g., MIPs) are designed, synthesized, and tested. To test a primer, a value is generated for each of one or more of the numbers of predicted site counts in Tables 1 and 2, based on a searching and counting process for unique and non-unique sites (with no mismatches or one mismatch) on each chromosome of interest and across the genome (including autosomes and sex chromosomes, for example). Any of the above-described examples or combinations of the above examples may be used as an objective function, to represent a score that is assigned to each primer and represents that primer's performance. The primers may be compared to one another based on their performance, and the best performing primers may be selected. As one example, a primer's score is compared to a predetermined threshold, to determine whether the primer is selected or not. In particular, when the objective function represented by EQ. 9 is used to represent each primer's score, the threshold may be set to a number, such as 2, 3, 4, 5, 6, 7, 8, 9, or 10.

In an illustrative embodiment, a primer with a high score (e.g., MIP 003 in the above table) was selected for further analysis. The results of the further analysis are described below in relation to Example 3. MIP 003 was selected because it was associated with a high value for the score as assessed according to EQ. 9. In particular, MIP 003 had a score of 8.557. Table 3 below summarizes the predicted numbers of unique sites that aligned to MIP 003 by different chromosomes with no mismatch (A) and with one mismatch (C).

TABLE 3

| Chromosome | Total number of unique sites (A + C) | Unique sites with no mismatch (A) | Unique sites with one mismatch (C) |
| --- | --- | --- | --- |
| chr1 | 15986 | 5499 | 10487 |
| chr2 | 13621 | 4773 | 8848 |
| chr3 | 11126 | 3926 | 7200 |
| chr4 | 9154 | 3227 | 5927 |
| chr5 | 9474 | 3279 | 6195 |
| chr6 | 9681 | 3326 | 6355 |
| chr7 | 10826 | 3812 | 7014 |
| chr8 | 7735 | 2652 | 5083 |
| chr9 | 7733 | 2668 | 5065 |
| chr10 | 8786 | 3031 | 5755 |
| chr11 | 7857 | 2714 | 5143 |
| chr12 | 9506 | 3330 | 6176 |
| chr13 | 4827 | 1725 | 3102 |
| chr14 | 5898 | 2019 | 3789 |
| chr15 | 6150 | 2146 | 4004 |
| chr16 | 7364 | 2439 | 4925 |
| chr17 | 9378 | 3315 | 6063 |
| chr18 | 3899 | 1399 | 2500 |
| chr19 | 9360 | 3203 | 6157 |
| chr20 | 4684 | 1618 | 3066 |
| chr21 | 2100 | 783 | 1317 |
| chr22 | 4092 | 1442 | 2650 |
| chroX | 7363 | 2547 | 4816 |
| chroY | 508 | 152 | 356 |

It is contemplated that the steps or descriptions of process 200 may be used with any other embodiment of this disclosure. In addition, the steps and descriptions described in relation to FIG. 2 may be done in alternative orders or in parallel to further the purpose of this disclosure. For example, each of these steps may be performed in any order or in parallel or substantially simultaneously to reduce lag or increase the speed of the system or method. Furthermore, it should be noted that process 200 may be carried out using computing device 100, and more particularly, CPU 106 of computing device 100.

Figure 3:
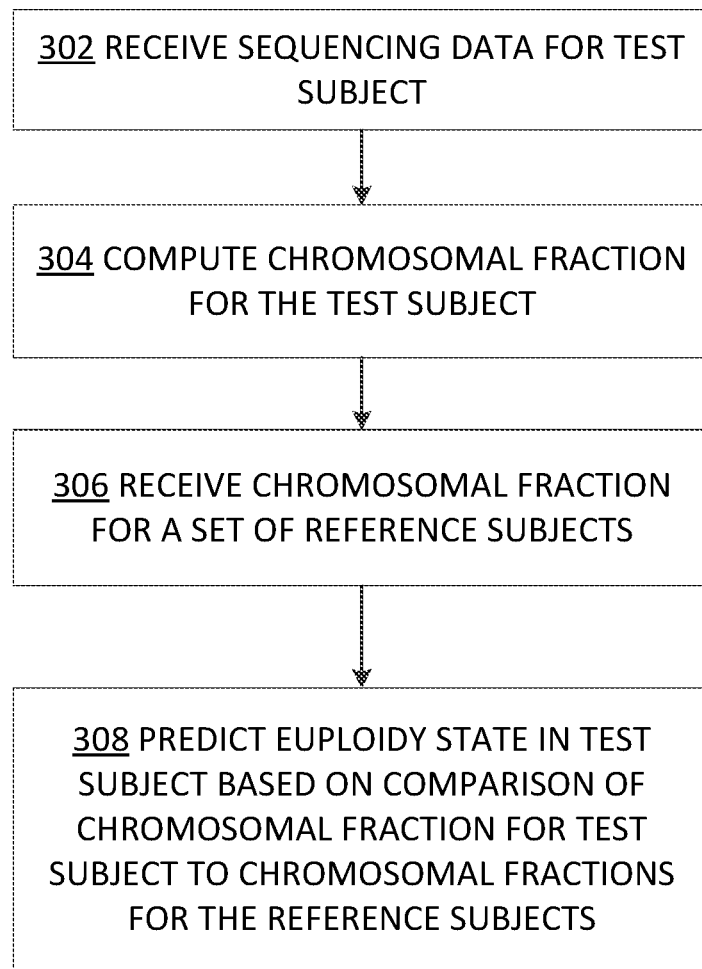
FIG. 3 is a representative process flow diagram for predicting aneuploidy state in a test subject according to some methods of the disclosure.

FIG. 3 is a flowchart of a process 300 for predicting aneuploidy state in a test subject, according to an illustrative embodiment. The process 300 includes the steps of receiving sequencing data for a test subject (step 302), computing site capture metric for the test subject (step 304), receiving site capture metrics for a set of reference subjects (step 306), and predicting aneuploidy state in the test subject based on comparison of site capture metric for the test subject to site capture metrics for the reference subjects (step 308). In some embodiments, the site capture metric is a site capture efficiency index (SCE), which is the ratio between the number of unique molecular identifier tags and the number of reads for each individual site. In some embodiments, the site capture metric is a site capture consistency measure (SCC), which is calculated as the coefficient of variability of SCE for each individual site. For example, in chromosome 1: 1-100, we have 100 aligned reads and 99 unique molecular identifier tags. Accordingly, the SCE will be 99%. In another example, out of 100 samples for chromosome 1: 1-100, all 100 samples have over 90% SCE, whereas out of the 100 samples for chromosome 3: 500-600, only 50 samples have over 90% SCE and the remaining 50 samples have less than 90% SCE. Accordingly, the SCC will indicate that chromosome 1: 1-100 is a more consistent site compared to chromosome 3: 500-600.

At step 302, sequencing data for a test subject is received. In particular, the test subject has an aneuploidy state that is unknown, and the received sequencing data is obtained by obtaining a nucleic acid sample from the test subject and using a population of primers, such as repeat offender molecular inversion probes (RO-MIPs), to capture a set of sites in the nucleic acid sample. As is described in detail in relation to FIG. 5, each RO-MIP includes in sequence a first targeting polynucleotide arm, a first unique targeting molecular tag, a polynucleotide linker, a second unique targeting molecular tag, and a second targeting polynucleotide arm. The first and second targeting polynucleotide arms are the same across the MIPs in the population, while the first and second unique targeting molecular tags are distinct across the MIPs in the population. RO-MIPs amplicons result from the capture of the sites, and the amplicons are sequenced to obtain the sequencing data.

At step 304, a chromosomal fraction is computed for the test subject by evaluating a ratio between a sum of all unique capture events from the chromosome of interest (S1) and a sum of all unique capture events from all chromosomes (S1+S2). The chromosomal fraction provides a proportional measure of the chromosome of interest in a given sample (i.e., the proportion of reads that comes from the chromosome of interest). One example method of computing the chromosomal fraction is described in relation to steps 426, 428, and 430 in FIG. 4.

At step 306, a set of chromosomal fractions for a set of reference subjects is received. In particular, the reference subjects may correspond to a group of people that exhibit a known euploidy state. For example, the subjects may exhibit monosomy, disomy, or trisomy for a particular chromosome of interest. The chromosomal fractions for the reference subjects are computed in the same manner as was described in relation to step 304, but for each reference subject. As is described in more detail in relation to FIG. 4, the chromosomal fractions are representative of the ability of the selected RO-MIP to capture sequences on the chromosome of interest, as compared to other chromosomes.

At step 308, the chromosomal fraction for the test subject (computed at step 304) is compared to the chromosomal fractions for the reference subjects (obtained at step 306), and the euploidy state of the test subject is predicted based on this comparison. In particular, a statistical test may be used to compare the test chromosomal fraction to the population of reference chromosomal fractions, and determine whether the test chromosomal fraction belongs in any cluster of reference chromosomal fractions associated with the same euploidy state. As used herein, "test ratio" may include the chromosomal fraction.

Figure 4:
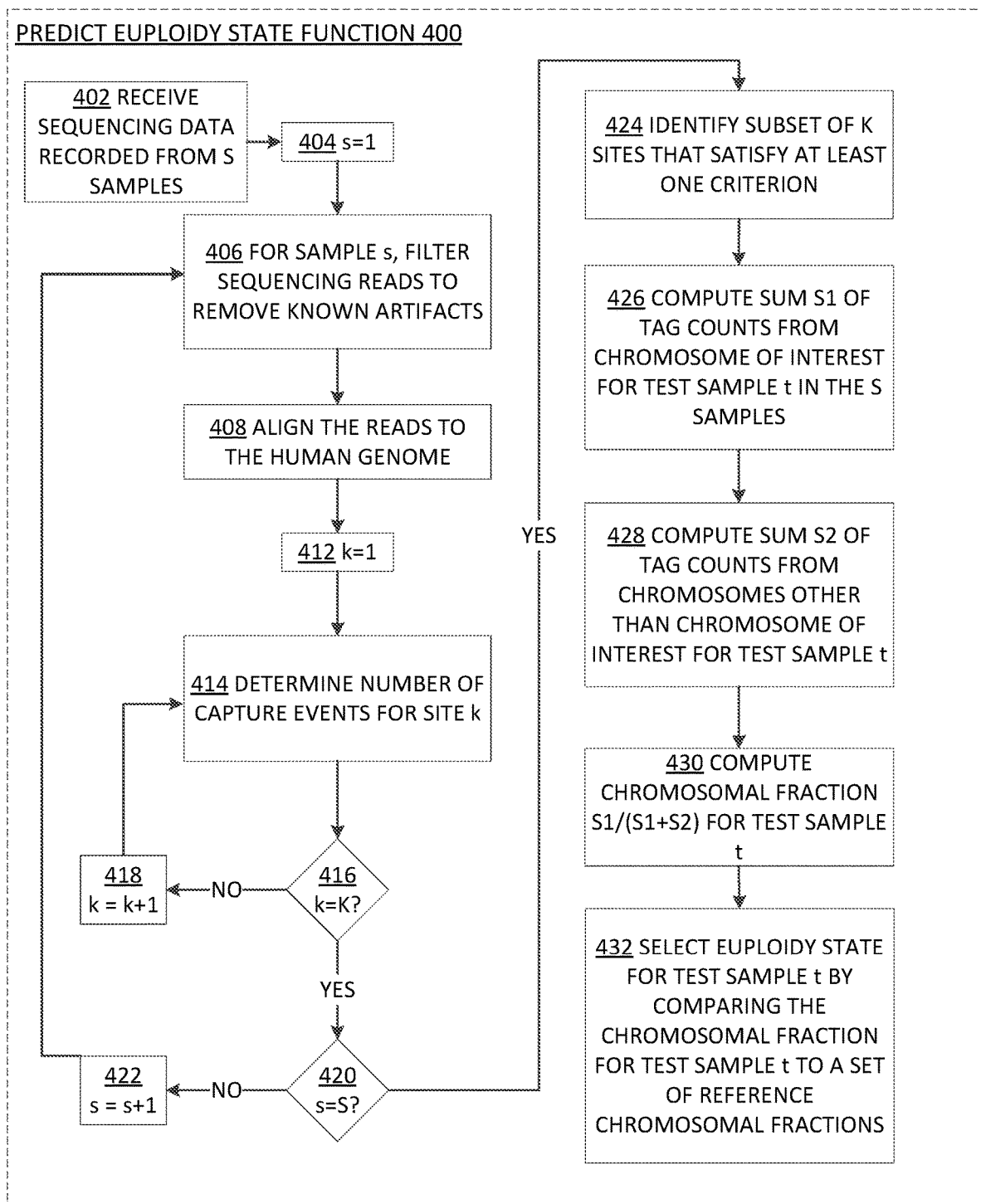
FIG. 4 is another representative and more detailed process flow diagram for predicting aneuploidy state of a test subject according to some methods of the disclosure.

FIG. 4 is a flowchart of a process 400 for predicting a euploidy state of a test subject, according to an illustrative embodiment. In an example, the process 400 may be used to implement the step 308 of the process 300 shown and described in relation to FIG. 3. As was described in relation to FIG. 3, a chromosomal fraction may be used to predict a euploidy state in a test subject that has an unknown euploidy state.

The process 400 includes the steps of receiving data recorded from S samples with known genotypes (step 402) and initializing a sample iteration parameter s to 1 (step 404). For each sample s, the process 400 includes filtering the sequencing reads to remove known artifacts (step 406), aligning the reads to the human genome (step 408), setting a site iteration parameter k to 1 (step 412), and determining a number of capture events for the k-th site (step 414). When all K sites and all S samples have been considered, the process 400 further includes the steps of identifying a subset of the K sites that satisfy at least one criterion (step 424), computing a first sum S1 of tag counts from a chromosome of interest for a test sample t in the S samples (step 426), computing a second sum S2 of tag counts from chromosomes other than the chromosome of interest for the test sample t (step 428), computing a chromosomal fraction as S1/(S1+S2) for the test sample t (step 430), and selecting a euploidy state for the test sample t by comparing the chromosomal fraction for the test sample t to a set of reference chromosomal fractions (step 432).

At step 402, data recorded from a set of S samples is received, where the S samples are each obtained from a different subject. At least one of the S samples is obtained from a test subject, whose euploidy state may be unknown. The samples may be nucleic acid samples isolated from the subjects, and the data may include sequencing data obtained from the nucleic acid samples. In an example, the sequencing data is obtained by using a population of RO-MIPs to amplify a set of sites in the nucleic acid sample to produce a set of RO-MIPs amplicons. The RO-MIPs amplicons may then be sequenced to obtain the sequencing data received at step 402.

At step 404, a sample iteration parameter s is initialized to 1. As the S samples are processed, the sample iteration parameter s is incremented until each of the S samples is processed to determine the number of capture events for each site.

At step 406, the sequencing reads for samples are filtered to remove known artifacts. In one example, the data received at step 402 may be processed to remove an effect of probe-to-probe interaction. In some embodiments, the ligation and extension targeting arms of all RO-MIPs are matched to the paired-end sequence reads. Reads that failed to match both arms of the RO-MIPs are determined to be invalid and discarded. The arm sequences for the remaining valid reads are removed, and the molecular tags from both ligation and extension ends may be also removed from the reads. The removed molecular tags may be kept separately for further processing at step 414.

At step 408, the resulting trimmed reads are aligned to the human genome. In some embodiments, an alignment tool may be used to align the reads to a reference human genome. In particular, an alignment score may be assessed for representing how well does a specific read align to the reference. Reads with alignment scores above a threshold may be referred to herein as primary alignments, and are retained. In contrast, reads with alignment scores below the threshold may be referred to herein as secondary alignments, and are discarded. Any reads that aligned to multiple locations along the reference genome may be referred to herein as multi-alignments, and are discarded.

At step 412, a site iteration parameter k is initialized to one. At step 414, the number of capture events for the k-th site is determined, and the site iteration parameter k is incremented at step 418 until all K sites have been considered.

When all K sites have been considered, the process 400 proceeds to step 424 to identify a subset of the K sites that satisfies at least one criterion. For example, a site capture consistency measure may be evaluated as a coefficient of variation of the number of capture events across the S samples, and those sites having high coefficients of variation may be discarded.

At step 426, a sum S1 of the tag counts from the chromosome of interest for a test sample is computed, and at step 428, a sum S2 of the tag counts from chromosomes other than the chromosome of interest for the test sample is computed. At step 430, a chromosomal fraction is computed as S1/(S1+S2). The chromosomal fraction for the test sample is then compared to a set of reference chromosomal fractions (that have been computed from reference subjects that have known euploidy states), and a statistical test is performed to select a predicted euploidy state for the test subject at step 432.

The order of the steps in FIG. 4 is shown for illustrative purposes only, and are not limiting.

It will be understood by one of ordinary skill in the art that the compositions and methods described herein may be adapted and modified as is appropriate for the application being addressed and that the compositions and methods described herein may be employed in other suitable applications, and that such other additions and modifications will not depart from the scope hereof.

This disclosure will be better understood from the Experimental Details which follow. However, one skilled in the art will readily appreciate that the specific methods and results discussed are merely illustrative of the disclosure as described more fully in the embodiments which follow thereafter.

EXAMPLES

Example 1: MIP Design and Method for Capturing Target Sequences of Interest

Probe Construction

Figure 5:
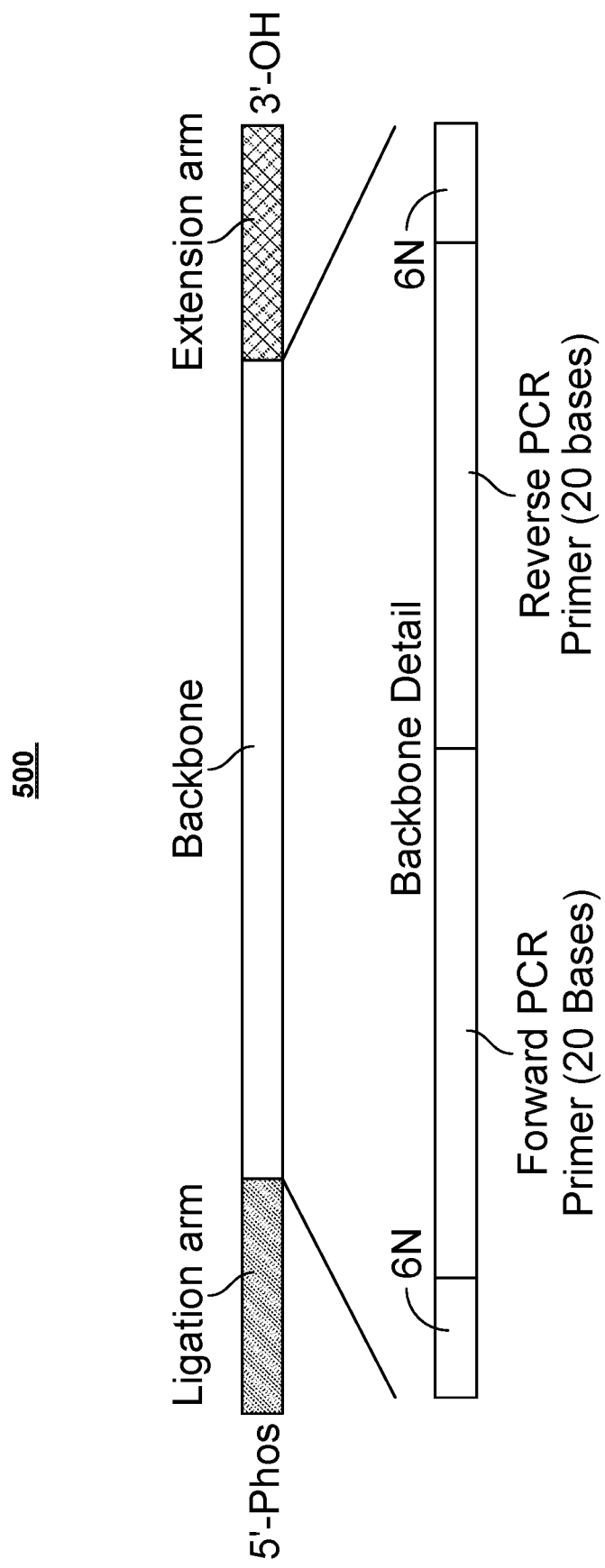
FIG. 5 shows the sequence of an exemplary molecular inversion probe (MIP) used in some methods of this disclosure. The MIP comprises in sequence the following components: a first targeting polynucleotide arm (labeled "Ligation arm"), a polynucleotide linker (labeled "Backbone," and comprising a first unique targeting molecular tag (labeled "6N"), a Forward PCR Primer, a Reverse PCR Primer, a second unique targeting molecular tag (also labeled "6N"), and a second targeting polynucleotide arm (labeled "Extension arm"). The first and second targeting polynucleotide arms in each of the MIP are substantially complementary to first and second regions in the nucleic acid that, respectively, flank a site of interest. The unique molecular tags are random polynucleotide sequences. In some embodiments, "substantially complementary" refers to 0 mismatches in both arms, or at most 1 mismatch in only one arm (e.g., when the targeting polynucleotide arms hybridize to the first and second regions in the nucleic acid that, respectively, flank a site of interest). In some embodiments, "substantially complementary" refers to at most a small number of mismatches in both arms, such as 1, 2, 3, 3, 5, 6, 7, or 8.

A single oligonucleotide ranging in size between 80 and 105 bp (depending on the length of the first and second targeting polynucleotide arms) is synthesized as shown in FIG. 5. The 6N boxes refer to molecular tag sequences that are used to quantitate capture events for each target sequence of interest. In this particular embodiment, instead of counting reads, the number of unique sequences per captured site are counted.

Site Capture Reaction

Figure 6:
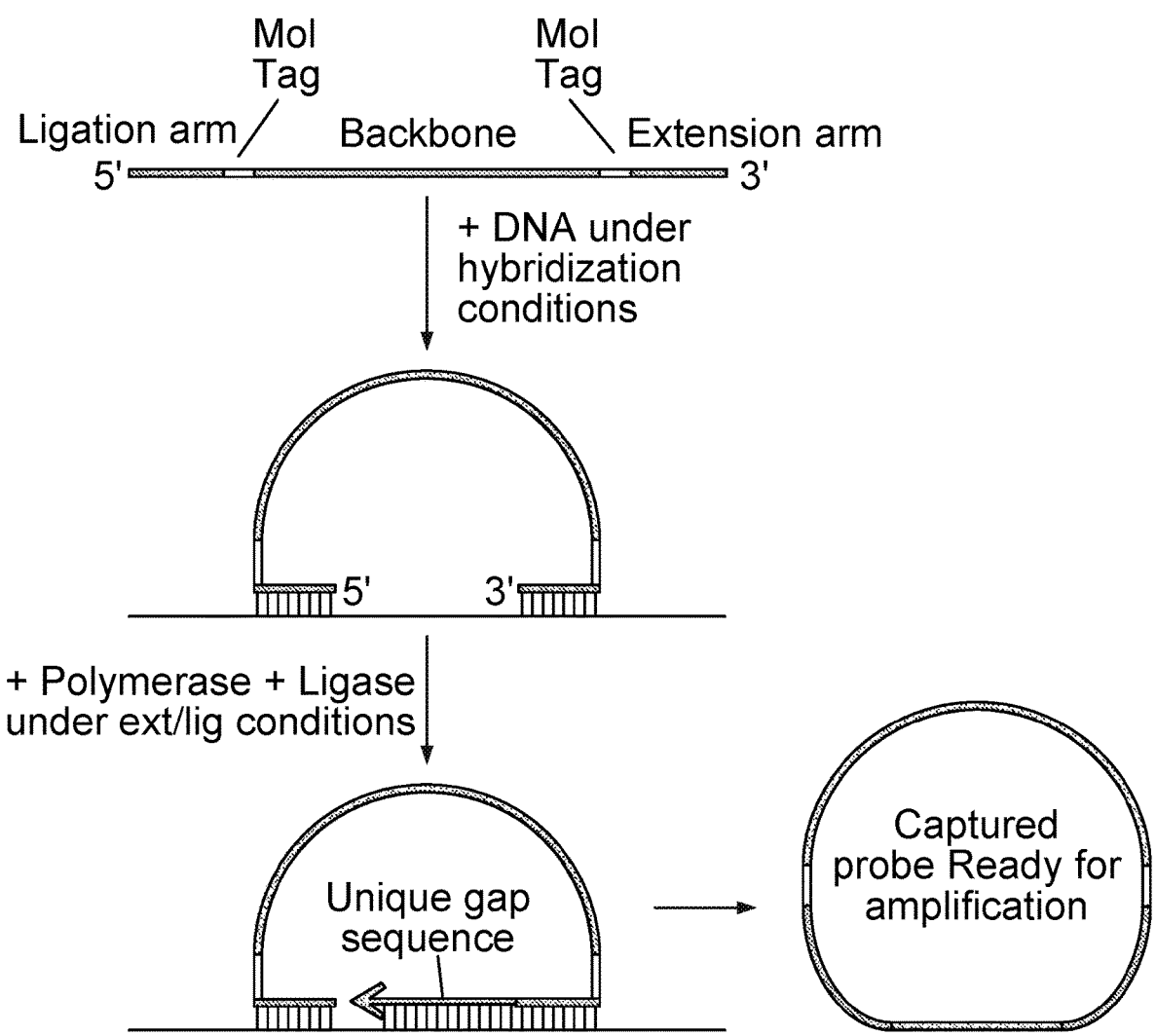
FIG. 6 depicts probe hybridization and extension/ligation in a method of the disclosure. The MIP is added to DNA under conditions suitable for hybridization of the first targeting polynucleotide arm (labeled "Ligation arm") and the second targeting polynucleotide arm (labeled "Extension arm") to the DNA template. After hybridization, a polymerase and a ligase are added under extension/ligation conditions, and a circular oligonucleotide (the "captured probe") is produced by DNA synthesis across the target sequence of interest containing the unique gap sequence between the ligation and extension arms. Upon melting of the amplicon and the csDNA, the captured probe is ready for amplification.
Figure 7:
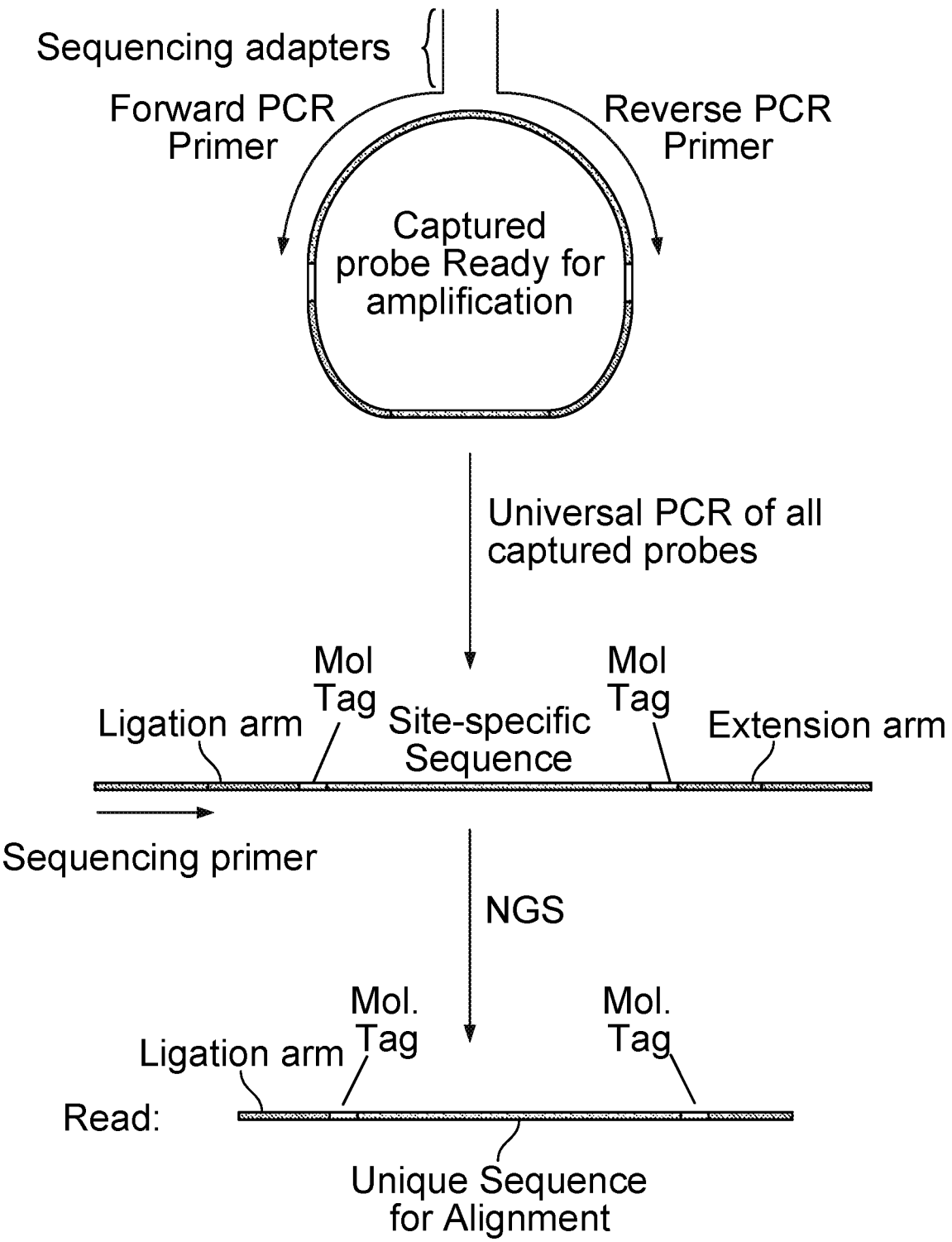
FIG. 7 depicts the amplification and sequencing of captured probes. Nucleic acid molecules comprising a sequencing adapter and a forward or a reverse PCR primer bind to the backbone of the circular amplicon, and all circular oligonucleotides that have been created by the MIPs are amplified using PCR. The amplicons are then sequenced using, for example, next generation sequencing (NGS), and the read count for the resulting amplicons is determined by counting the number of occurrences of the unique molecular tags in each amplicon.

The first and second targeting polynucleotide arms (at an empirically determined concentration) is mixed with csDNA extracted from 1-2 mL plasma in a 20 uL buffered reaction. The mixture is incubated in a thermocycler at temperatures that have been optimized for annealing of probes to the template (98° C. for 3 min→85° C. for 30 min→66° C. for 15 min). During this incubation, the probe molecules anneal to the csDNA template at specific chromosomal locations that are complementary to the probe sequence (FIG. 6, middle). The most easily predicted sites are those with sequences that are exactly complementary to the first and second targeting polynucleotide arms (invariant sites), but sites that have one or more variants in either arm are also targeted at somewhat lower efficiency. The optimal amount of MIP for each reaction is dependent on three main variables: 1) the number of genomes used as template, which can vary widely among individuals, 2) the overall number of sites targeted by the specific probe, and 3) the ratio of invariant sites to variant sites.

After the hybridization program is complete, a 5 uL mixture of enzymes and reagents is added and the mixture is incubated at 66° C. for 1 hr, then 72° C. for 30 min, then cooled to 4° C. We see a dramatic increase in specificity by raising both the hybridization and extension temperatures to 66° C. During this step, the gap is filled in by DNA polymerase and the MIP is covalently circularized by a DNA ligase (Figure E, bottom). Only probes that were annealed to the template are circularized during this step, and linear probes are not amplifiable because of the gap between the primer binding sites.

Captured Site Amplification 20 uL of the captured MIP mixture is added to a 50 uL reaction mixture containing thermostable polymerase, dNTPS, PCR buffer, and universal primers that are complementary to the probe backbone (Figure F, top). Each sample is amplified using a primer with a distinct "barcode" sequence allowing multiplex sequencing of a pooled sample library. The reaction is subjected to an empirically determined number of PCR cycles until a clean amplicon band is observable by electrophoresis. The PCR product is purified using Ampure beads and quantitated using a Qubit fluorometer.

Sequencing the Captured Sites

The purified PCR products are pooled into a library such that all samples are at equal concentration, ensuring that the read budget is divided evenly across the samples. The library is sequenced using either single-end or paired-end sequencing, using 75-100 cycles in order to determine the full sequence of the site-specific gap. If single-end sequencing is used, the read will consist of the ligation arm followed by the molecular tag and the unique gap sequence that was filled in during the ext/lig step. Sequencing into the extension arm is unnecessary because the sequence is known from the probe.

Example 2: Sequence Data Analysis and Detection of Aneuploidy in a Subject

Raw sequencing data must be processed in order for it to be useful in detecting aneuploidy. To start, sequencing reads are filtered to remove known artifacts such as probe-to-probe interaction, backbone sequences or adapter sequences. The ligation and extension arms of the MIP (i.e., the first and second targeting polynucleotide arms) are then matched to the sequence reads, allowing a maximum of one base pair mismatch in each arm. Reads that fail to meet this criterion are treated as invalid and discarded. The arm sequences for the valid reads are trimmed to remove the non-genomic portions from the sequence data by deleting the sequence from the read files used in subsequent processing steps. At the same time, the molecular tags from both the ligation and the extension ends are kept separately for counting of the capture events in a later step. The trimmed reads are aligned to the human genome (hg19) with the bowtie2 software program. The aligned reads are then filtered with the samtools software program to remove reads that do not align as a valid pair, or that align non-uniquely. The alignment and filtering parameters are carefully chosen to keep uniquely aligned reads only. The aligned and filtered reads (in bam format files) are examined to count the unique molecular tags for each targeted site with a unique MIP gap sequence (i.e., a unique target sequence of interest). These counts are the initial number of MIP-to-target hybridization events that are sequenced in a next generation sequencing platform (e.g., an Illumina HiSeq 2500 flowcell). A site capture efficiency index (SCE) is calculated for each individual site. A site capture consistency measure (SCC) is calculated as the coefficient of variability of SCE for each individual site. A portion of these sites are discarded based on site capture efficiency variability measures from experimental data. This step helps to reduce sample-to-sample variability in the chromosomal proportion and increase the Z-score of positive samples calculated in a later step. For a given sample, the sum (S1) of unique molecular tags counts from the remaining sites on the chromosome of interest (e.g., chromosome 21) is calculated and stored. The sum (S2) of the remaining reference sites is calculated and stored. The ratio between the two sums (chromosomal fraction=S1/(S1+S2)) is calculated as the proportional measure of the chromosome of interest in a given sample. Using the chromosomal fraction measures, the Z-score of the chromosome of interest (e.g., chromosome 21) is calculated for each test sample against a collection of reference samples with normal fetal chromosome count (i.e. normal karyotope fetus). The determination of aneuploidy (e.g., trisomy and monosomy) or euploidy is made when the absolute value of the Z-score of a given sample is above a certain threshold.

Figure 8:
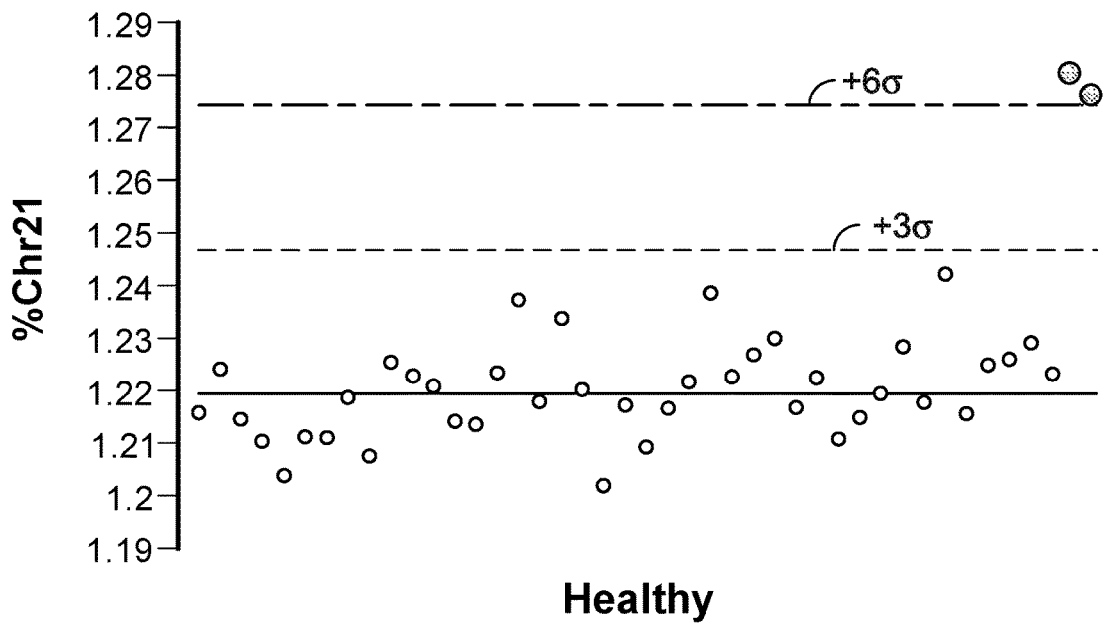
FIG. 8 depicts the results from a test for trisomy of chromosome 21 (Down syndrome). Of the 48 samples tested, 46 were negative for Down syndrome, while 2 samples were positive for Down syndrome. The two positive samples are shown in the upper right, with a Z-score greater than 6.

Using the above method, 48 samples from pregnant women were tested for Down syndrome (trisomy of chromosome 21). The assay confirmed that two samples were positive for Down syndrome, while 46 samples were negative. The separation between the positive and negative samples was particularly clear, with a Z-score greater than 6 in both positive samples. See FIG. 8.

Example 3: Detection of Trisomy 13, 18, and 21 in Pregnant Subjects

This example describes using the method described herein to discriminate (or distinguish) between pregnant women carrying trisomy 13, 18, and 21 and healthy pregnant women.

Determination of Z-Score Cutoffs for Detecting Trisomy 13, 18, and 21

A training set of 48 plasma samples from pregnant women (study approved by institutional review board) is used to determine Z-score cutoffs for detecting trisomy 13, 18, and 21. Each of the plasma samples is taken from a different pregnant woman. The 48 plasma samples contain 40 healthy samples, four Trisomy 21 samples, three Trisomy 18 samples, and one Trisomy 13 sample. Trisomy cases are confirmed by karyotype analysis of placental or fetal cells collected by CVS (Chorionic villus sampling) or amniocentesis.

Site capture reaction: Plasma DNA extracted from each of the 48 pregnant women is subjected to a site capture reaction as follows: the extracted plasma DNA is mixed with water, Ampligase buffer (1×), and the RO-MIP at the empirically determined probe concentration. The site capture reaction mixture is incubated in a thermal cycler at 98° C. for 3 min, then 85° C. for 30 min, then 66° C. for 15 min. After the incubation, a master mixture containing dNTP (0.6 mM), NAD (0.4×), betaine (0.3M), Ampligase buffer (1×), water, Ampligase (5 units), and Phusion HF polymerase (0.4 units) is added to the site capture reaction mixture. The combined mixture is then incubated in a thermal cycler at 66° C. for 60 min, 72° C. for 30 min, and held at 4° C.

Captured site amplification: After the incubation, 20 µL of the combined mixture is added to a PCR master mixture containing forward (500 nM) and reverse index primers (500 nM), Phusion HF buffer (1×), dNTPs (0.2 mM), water, and Phusion HS polymerase (0.4 units). Each sample is barcoded with a unique reverse primer index. The PCR reaction mixture is incubated in a thermal cycler at 98° C. for 3 min, then 20 cycles at 98° C. for 10 sec, 65° C. for 20 sec, and 72° C. for 30 sec. The PCR reaction mixture is then held at 72° C. for 5 min and then 4° C.

Single-end sequencing: The PCR amplified libraries are purified using AmpureXP beads and samples are pooled together at equal concentration (48 samples per pool). The multiplexed libraries are each loaded on a single SR flowcell and sequenced in Rapid Run mode on an HiSeq 2500 for 106 cycles.

Data analysis: Sequencing data are filtered and aligned. A chromosome proportion ($P_i$) is calculated for chromosomes 13, 18, and 21 by dividing the number of unique molecular tags/identifiers from reads that are uniquely aligned to each chromosome (i.e., chromosome 13, 18, or 21) (this numerator is analogous to the sum of "A" and "C") by the total number of unique molecular tags/identifiers from reads that are uniquely aligned to chromosomes 1 to 22 (this denominator is analogous to the sum of "A", "C", "E", and "G"). However, while the values in Table 2 (E-H) include all chromosomes across the genome (including chromosomes 1 to 22, X, and Y), the denominator here may not include reads that align to the X or Y chromosomes. In particular, the number of reads that align to the X or Y chromosomes may be significantly larger than the number of reads that align to other chromosomes, including the chromosome of interest. In this case, including the reads that align to the X or Y chromosomes in the denominator may significantly reduce the resulting ratio, and may introduce noise and distortion to the calculation of the z-statistic. Accordingly, when the chromosome of interest is neither the X nor the Y chromosome (e.g., when detecting an autosomal aneuploidy), the reads that align to the X or Y chromosomes may be excluded from both the numerator and the denominator. Alternatively, when the chromosome of interest is a sex chromosome (e.g., when detecting a sex chromosome aneuploidy), the reads that align to the X and/or Y chromosomes may be included in the numerator and the denominator.

For the resulting ratios, the mean ($x_i$) and standard deviation ($s_i$) is calculated for the unaffected samples and used to calculate a Z-score ($[P_i - x_i]/s_i$) for each sample. Analysis of the Z-scores reveals that all healthy samples have Z-scores <3.0 for chromosomes 13, 18, and 21, while positive samples have Z-scores >3.0 for chromosomes 13, 18, and 21. Therefore, it is determined that samples with a Z-score >3.0 will be called positive for trisomy 13, 18, and 21. Samples with a Z-score <3.0 will be called negative for trisomy 13, 18, and 21.

Determination of Sensitivity and Specificity for Detecting Trisomy 13, 18, and 21

A test set of 422 samples from pregnant women (study approved by institutional review board) is used to determine sensitivity and specificity of the test. Each sample is from a different pregnant woman. These 422 samples contain 387 healthy samples, 21 T21 samples, 9 T18 samples, and 5 T13 samples. Trisomy cases are confirmed by karyotype analysis of placental or fetal cells collected by CVS or amniocentesis.

Site capture reaction: Plasma DNA extracted from each of the 422 pregnant women is subjected to a site capture reaction as follows: the extracted plasma DNA is mixed with water, Ampligase buffer (1×), and the RO-MIP at the empirically determined probe concentration. The capture reaction mixture is incubated in a thermal cycler at 98° C. for 3 min, then 85° C. for 30 min, then 66° C. for 15 min. After the incubation, a master mixture containing dNTP (0.6 mM), NAD (0.4×), betaine (0.3M), Ampligase buffer (1×), water, Ampligase (5 units), and Phusion HF polymerase (0.4 units) is added to the site capture reaction mixture. The combined reaction mixture is incubated in a thermal cycler at 66° C. for 60 min, 72° C. for 30 min, and held at 4° C.

Captured site amplification: After the incubation, 20 µL of the combined mixture is added to a PCR master mixture containing forward (500 nM) and reverse index primers (500 nM), Phusion HF buffer (1×), dNTPs (0.2 mM), water, and Phusion HS polymerase (0.4 units). Each sample is barcoded with a unique reverse primer index. The PCR reaction mixture is incubated in a thermal cycler at 98° C. for 3 min, then 20 cycles at 98° C. for 10 sec, 65° C. for 20 sec, and 72° C. for 30 sec. The PCR reaction mixture is held at 72° C. for 5 min and then 4° C.

Single-end sequencing: The amplified libraries are purified using AmpureXP beads and samples are pooled together at equal concentration (48 samples per pool). There are 9 pools total: the first eight pools having 47 test samples and 1 control sample per pool and the ninth pool has 46 test samples and 1 control sample. The multiplexed libraries are each loaded on a single SR flowcell and sequenced in Rapid Run mode on an HiSeq 2500 for 106 cycles.

Figure 10:
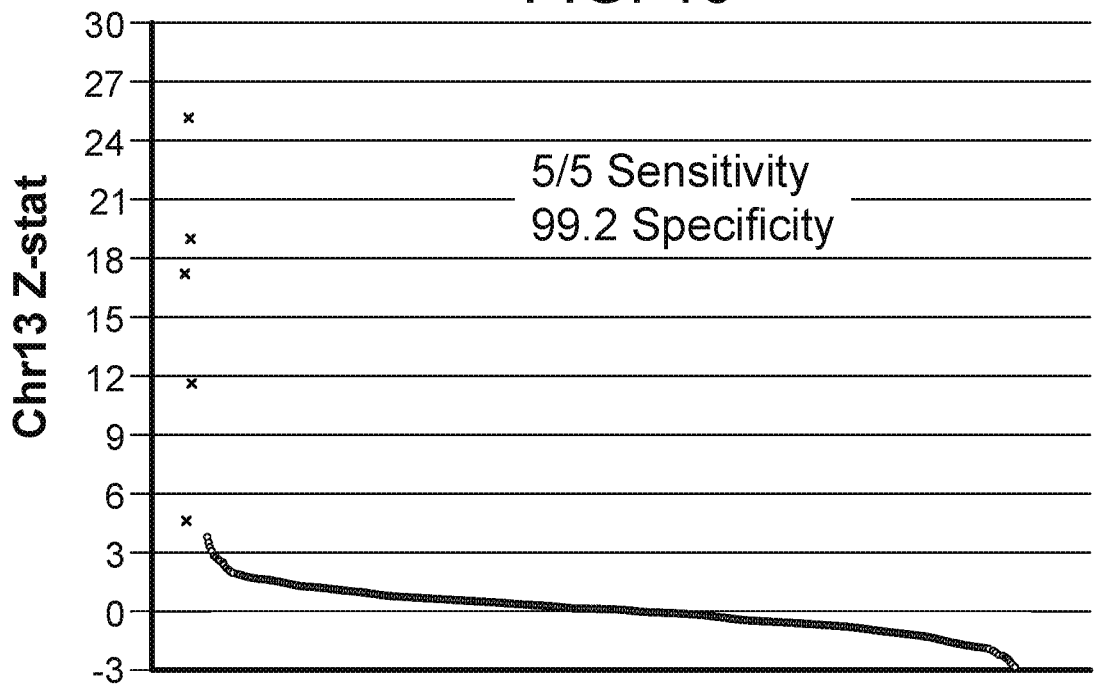
FIGS. 10-12 depict the test performance as evaluated by an example MIP in detecting Trisomy 13, 18, and 21, respectively.
Figure 11:
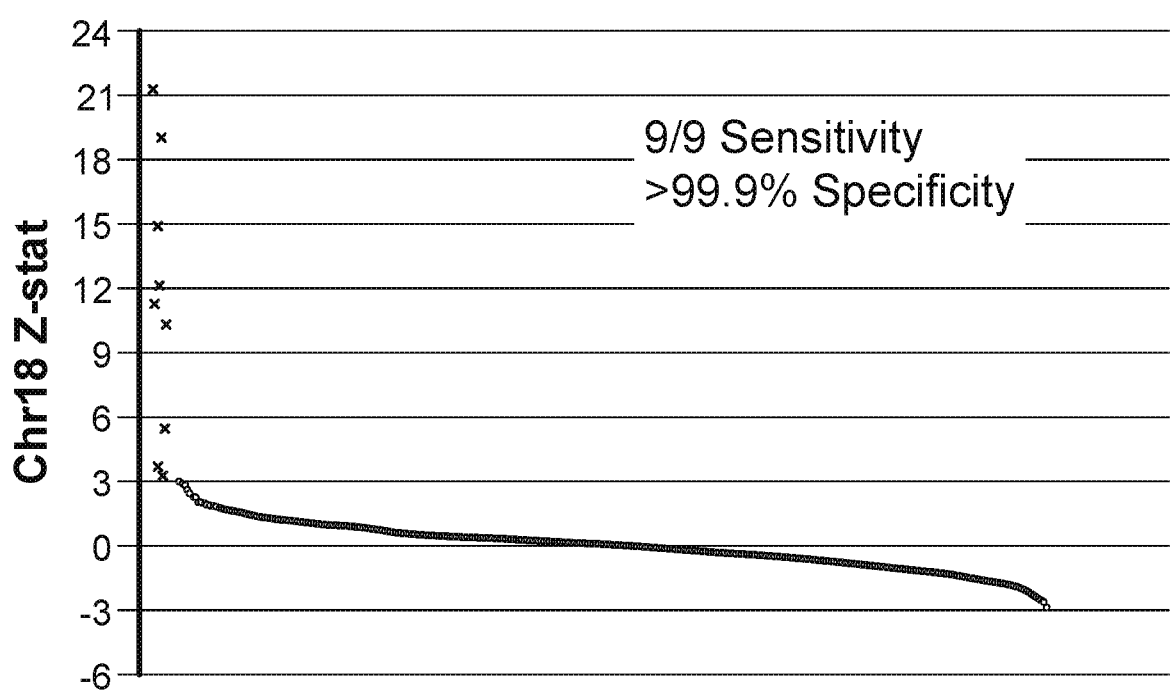
Figure 12:
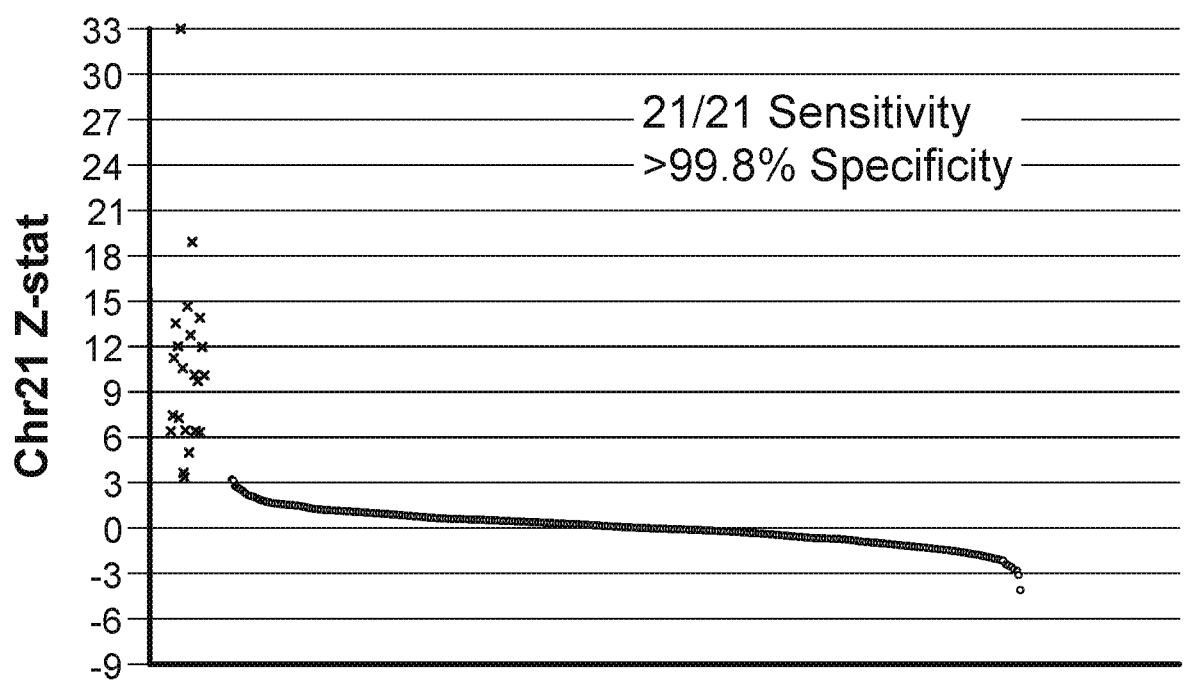

Data analysis: The DNA from each of the 422 pregnant women are subjected to the site capture reaction, captured site amplification, and single-end sequencing using 106 cycles, as with the training set. Sequence data from each sample are used to calculate a Z-score for chromosomes 13, 18, and 21 (FIGS. 10-12). Using the cutoffs determined by the training set, specificity (e.g., the true negative rate, or the number of true negatives divided by the sum of true negatives and false positives) is >99.9% for trisomy 13 (5/5), 18 (9/9), and 21 (21/21). Sensitivity (e.g., the true positive rate, or the number of true positives divided by the sum of true positives and false negatives) is >99.2% for chromosome 13, >99.9% for chromosome 18, and >99.5% for chromosome 21.

The graph in FIG. 10 shows the primer's test performance in detecting Trisomy 13. The y-axis in FIG. 10 represents the z-statistic, and the x-axis represents the five Trisomy 13 samples on the left (in no particular order) and the remaining 545 samples on the right (in order of decreasing z-statistic). As is shown in FIG. 10, all five Trisomy 13 samples had z-statistics higher than 3.0 and were correctly identified as positive samples using the primer, leading to a 5/5 sensitivity. A small number of healthy samples had z-statistics greater than 3.0, leading to a 99.2% specificity.

FIG. 11 is similar to FIG. 10, except that FIG. 11 shows the primer's test performance in detecting Trisomy 18. All nine Trisomy 18 samples had z-statistics higher than 3.0 and were correctly identified as positive samples using the primer, leading to a 9/9 sensitivity. Moreover, nearly all of the healthy samples were correctly identified as negative samples, leading to a specificity rate greater than 99.9%. FIG. 12 is also similar to FIG. 10, except that FIG. 12 shows the primer's test performance in detecting Trisomy 21. All 21 Trisomy 21 samples were correctly identified as positive samples using the primer, leading to a 21/21 sensitivity. Moreover, nearly all of the healthy samples were correctly identified as negative samples, leading to a specificity rate greater than 99.8%.

The results shown in FIGS. 10-12 indicate that the systems and methods of the present disclosure provide a useful tool for selecting a primer with high sensitivity and specificity in detecting aneuploidy. Other methods may also have similar levels of performance (as measured by sensitivity and/or specificity, for example). For example, similar performance may be achieved using shotgun sequencing. However, the present disclosure has several advantages over other approaches because the present disclosure uses only a single primer, and may therefore be cheaper, simpler, and more efficient than those other approaches.

For illustrative purposes, the examples provided by this disclosure focus primarily on a number of different example embodiments of systems and methods to determine copy number variations, chromosomal abnormalities, or microdeletions. However, it is understood that variations in the general shape and design of one or more embodiments may be made without significantly changing the functions and operations of the present disclosure. Furthermore, it should be noted that the features and limitations described in any one embodiment may be applied to any other embodiment herein, and the descriptions and examples relating to one embodiment may be combined with any other embodiment in a suitable manner. Moreover, the figures and examples provided in disclosure are intended to be only exemplary, and not limiting. It should also be noted that the systems and/or methods described above may be applied to, or used in accordance with, other systems and/or methods, including systems and/or methods which may or may not be directly related to determining copy number variations.

We claim:

1. A method of characterizing fetal DNA in a maternal blood sample, comprising:
   a) obtaining a DNA sample isolated from a maternal blood sample;
   b) capturing a plurality of target sequences from target sites in the DNA sample using a population of molecular inversion probes (MIPs), wherein each MIP in the population of MIPs comprises:
      i) a pair of targeting polynucleotide arms comprising a first targeting polynucleotide arm and a second targeting polynucleotide arm, wherein the first targeting polynucleotide arm has a different nucleotide sequence than the second targeting polynucleotide arm;
      ii) a unique molecular tag; and
      iii) a polynucleotide linker
   in a sequence:
      the first targeting polynucleotide arm-the unique molecular tag-the polynucleotide linker-the second targeting polynucleotide arm;
      wherein the pairs of targeting polynucleotide arms in the population of MIPs are identical, and wherein the first targeting polynucleotide arm and the second targeting polynucleotide arm are substantially complementary to pairs of first and second regions that flank each target sequence in the plurality of target sequences in the DNA sample, and wherein the capturing comprises hybridizing the population of MIPs to the DNA sample to produce hybridized MIPs comprising MIPs, from the population of MIPs, hybridized at first target sites and MIPs, from the population of MIPs, hybridized at second target sites, wherein the first target sites comprise target sequences found on a single chromosome and wherein the second target sites comprise target sequences found on multiple chromosomes;
   c) circularizing hybridized MIPs to produce MIP replicons;
   d) amplifying MIP replicons obtained in step c) to form MIP amplicons;
   e) sequencing MIP amplicons obtained in step d) to produce sequence reads;
   f) using the sequence reads to determine a number of first capture events based on the unique molecular tags from the MIPs hybridized at first target sites in step b);
   g) using the sequence reads to determine a number of second capture events based on the unique molecular tags from the MIPs hybridized at second target sites in step b);

h) providing first site capture metrics by determining, for each target site of the first target sites, a first site capture metric based at least in part on the number of first capture events determined in step f);

i) identifying a first subset of the first site capture metrics determined in step h) that satisfy at least one criterion;

j) providing second site capture metrics by determining, for each target site of the second target sites, a second site capture metric based at least in part on the number of second capture events determined in step g);

k) identifying a second subset of the second site capture metrics determined in step j) that satisfy the at least one criterion;

l) normalizing a first measure determined from the first subset of first site capture metrics identified in step i) by a second measure determined from the second subset of second site capture metrics identified in step k) to obtain a test ratio; and m) detecting a difference between the test ratio and a plurality of reference ratios that are computed based on reference DNA samples isolated from reference subjects known to exhibit euploidy or aneuploidy, to characterize the fetal DNA in the maternal blood sample.

2. The method of claim 1, wherein at least one of the following is satisfied:
(1) the length of the first targeting polynucleotide arm is between 14 and 30 nucleotides,
(2) the length of the second targeting polynucleotide arm is between 14 and 30 nucleotides,
(3) each of the targeting polynucleotide arms has a melting temperature between 45° C. and 80° C., or
(4) each of the targeting polynucleotide arms has a GC content between 30% and 80%, or between 30% and 70%.

3. The method of claim 2, wherein the first targeting polynucleotide arm comprises the nucleotide sequence of (SEQ ID NO: 4)
5'-CACTGCACTCCAGCCTGG-3'.

4. The method of claim 2, wherein the second targeting polynucleotide arm comprises the nucleotide sequence of (SEQ ID NO: 5)
5'-GAGGCTGAGGCAGGAGAA-3'.

5. The method of claim 1, wherein the polynucleotide linker is not substantially complementary to any genomic region of the subject, and at least one of the following is satisfied:
(1) the polynucleotide linker has a length of between 20 and 1,000 nucleotides,
(2) the polynucleotide linker has a melting temperature of between 45° C. and 80° C.,
(3) the polynucleotide linker has a GC content between 30% and 80%, or between 30% and 70%, or
(4) the polynucleotide linker comprises at least one of a forward amplification primer and a reverse amplification primer.

6. The method of claim 5, wherein the polynucleotide linker comprises the nucleotide sequence of (SEQ ID NO: 3)
5'-CTTCAGCTTCCCGATTACGGGCACGATCCGACGGTAGTGT-3'.

7. The method of claim 1, wherein the MIPs in the population of MIPs comprise the nucleotide sequence of (SEQ ID NO: 6)
5'-CACTGCACTCCAGCCTGG($N_{1-6}$)

CTTCAGCTTCCCGATTACGGGCACGATCCGACGGTAGTGT($N_{7-12}$)

GAGGCTGAGGCAGGAGAA-3', wherein ($N_{1-6}$) represents the unique molecular tag and ($N_{7-12}$) is present or absent, and represents another unique molecular tag.

8. The method of claim 1, wherein the population of MIPs has a concentration between 10 fM and 100 nM.

9. The method of claim 1, wherein the size of the MIP replicons is between 80-90 nucleotides.

10. The method of claim 1, wherein the sequencing of step e) has a read depth of between 6-8 million reads.

11. The method of claim 1, wherein each of the MIPs replicons provided in step c) is produced by:
i) the first and second targeting polynucleotide arms, respectively, hybridizing to the first and second regions of a DNA in the DNA sample, respectively, wherein the first and second regions flank a target sequence; and
ii) after the hybridization, using a ligation/extension mixture to extend and ligate a gap region between the two targeting polynucleotide arms of a MIP in the population of MIPs to form a single-stranded circular MIP replicon.

12. The method of claim 1, further comprising computing a variability coefficient for a plurality of site capture metrics for a particular site, wherein each site capture metric in the plurality of site capture metrics is evaluated from a DNA sample from a different subject, and wherein the at least one criterion used at steps i) and k) includes a requirement that the variability coefficient for the particular site is below a threshold value.

13. The method of claim 1, wherein the first measure determined at step l) is a sum of the first subset of site capture metrics and corresponds to a chromosome of interest, and the second measure determined at step l) is a sum of the second subset of site capture metrics and corresponds to chromosomes other than the chromosome of interest.

14. The method of claim 1, wherein the detecting at step m) comprises performing a statistical test to evaluate whether the test ratio obtained at step l) is statistically different from the plurality of reference ratios.

15. The method of claim 1, wherein the test ratio and the reference ratios are chromosomal fractions.

* * * * *